(12) United States Patent
Andersen et al.

(10) Patent No.: US 6,610,721 B2
(45) Date of Patent: Aug. 26, 2003

(54) IMIDAZO HETEROCYCLIC COMPOUNDS

(75) Inventors: Knud Erik Andersen, Brondby (DK); Florencio Zaragoza Dorwald, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/810,311

(22) Filed: Mar. 16, 2001

(65) Prior Publication Data

US 2001/0049385 A1 Dec. 6, 2001

Related U.S. Application Data

(60) Provisional application No. 60/194,920, filed on Apr. 4, 2000.

(30) Foreign Application Priority Data

Mar. 17, 2000 (DK) .......................... 2000 00442

(51) Int. Cl.[7] .................. C07D 235/02; A61K 31/4184; A61P 3/10
(52) U.S. Cl. ...................... 514/393; 514/399; 548/302.7
(58) Field of Search ........................ 548/302.7; 514/399, 514/393

(56) References Cited

U.S. PATENT DOCUMENTS

| 4,767,778 A | 8/1988 | Arrang et al. ............... 514/397 |
| 5,578,616 A | 11/1996 | Aslanian et al. ............ 514/341 |

FOREIGN PATENT DOCUMENTS

| EP | 0 197 840 B1 | 10/1986 |
| EP | 0 214 058 A2 | 3/1987 |
| EP | 0 338 939 A1 | 10/1989 |
| EP | 0 458 661 A1 | 11/1991 |
| EP | 0 494 010 A1 | 7/1992 |
| EP | 0 531 219 A1 | 3/1993 |
| JP | 08-325234 | 12/1996 |
| WO | WO 91/17146 | 11/1991 |
| WO | WO 92/15567 | 9/1992 |
| WO | WO 93/12093 | 6/1993 |
| WO | WO 93/12107 | 6/1993 |
| WO | WO 93/12108 | 6/1993 |
| WO | WO 93/14070 | 7/1993 |
| WO | WO 93/20061 | 10/1993 |
| WO | WO 94/17058 | 8/1994 |
| WO | WO 95/06037 | 3/1995 |
| WO | WO 95/11894 | 5/1995 |
| WO | WO 95/14007 | 5/1995 |
| WO | WO 96/38141 | 12/1996 |
| WO | WO 96/38142 | 12/1996 |
| WO | WO 96/40126 | 12/1996 |
| WO | WO 99/42458 | 8/1999 |
| WO | WO 00/63208 | 10/2000 |

OTHER PUBLICATIONS

Morisset et al., Nature, vol. 408, pp. 860–864 (2000).
Leurs et al., Progress in Drug Research, vol. 45, pp. 107–165 (1995).
Stark et al., Drugs of the Future, vol. 21, pp. 507–520 (1996).
Krebs et al., Helvetica Chimica Acta, vol. 62, pp. 497–506 (1979).
von Ernst–Peter Krebs, Helvetica Chimica Acta, vol. 62, pp. 507–510.
Carlstrom et al., Acta Chemica Scandinavica B, vol. 35, pp. 107–116 (1981).

*Primary Examiner*—Joseph K. McKane
*Assistant Examiner*—Kamal Saeed
(74) *Attorney, Agent, or Firm*—Rosemarie R. Wilk-Orescan; Reza Green

(57) ABSTRACT

A novel class of imidazo heterocyclic compounds, pharmaceutical compositions comprising them and use thereof in the treatment and/or prevention of diseases and disorders related to the histamine H3 receptor. More particularly, the compounds are useful for the treatment and/or prevention of diseases and disorders in which an interaction with the histamine H3 receptor is beneficial.

29 Claims, No Drawings

IMIDAZO HETEROCYCLIC COMPOUNDS

CROSS REFERENCE TO RELATED APPLICATIONS

This application claims priority under 35 U.S.C. 119 of Danish application no. PA 2000 00442 filed on Mar. 17, 2000, and U.S. provisional application No. 60/194,920 filed on Apr. 4, 2000, the contents of which are fully incorporated herein by reference.

FIELD OF THE INVENTION

The present invention relates to novel imidazo heterocyclic compounds, to the use of these compounds as pharmaceutical compositions, to pharmaceutical compositions comprising the compounds, and to a method of treatment employing these compounds and compositions. The present compounds show a high and selective binding affinity to the histamine H3 receptor indicating histamine H3 receptor antagonistic, inverse agonistic or agonistic activity. As a result, the compounds are useful for the treatment and/or prevention of diseases and disorders related to the histamine H3 receptor.

BACKGROUND OF THE INVENTION

The existence of the histamine H3 receptor has been known for several years and the receptor is of current interest for the development of new medicaments (see eg Stark, H.; Schlicker, E.; Schunack, W., *Drugs Fut.* 1996, 21, 507–520; Leurs, R.; Timmerman, H.; Vollinga, R. C., *Progress in Drug Research* 1995, 45, 107–165). Recently, the human histamine H3 receptor has been cloned, cf Lovenberg, T. W. et al, *Molecular Pharmacology*, June 1999, 55, 1101–1107. The histamine H3 receptor is a presynaptic autoreceptor located both in the central and the peripheral nervous system, the skin and in organs such as the lung, the intestine, probably the spleen and the gastrointestinal tract. Recent evidence suggests that the H3 receptor show intrinsic, constitutive activity, in vitro as well as in vivo (i.e. it is active in the absence of an agonist; see eg Morisset et al., *Nature* 2000, 408, 860–864). This activity can be inhibited by compounds acting as inverse agonists.

The histamine H3 receptor has been demonstrated to regulate the release of histamine and also of other neurotransmitters such as serotonin and acetylcholine. A histamine H3 receptor antagonist or inverse agonist would be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

Several publications disclose the preparation and use of histamine H3 agonists and antagonists see eg U.S. Pat. No. 4,767,778 (corresponding to EP 214 058), EP 338 939, WO 93/14070, EP 531 219, EP 458 661, EP 197 840, EP 494 010, WO 91/17146, WO 93/12108, WO 93/12107, WO 93/12093, U.S. Pat. No. 5,578,616 (corresponding to WO 95/14007), WO 96/38142, WO 96/38141, WO 95/11894, WO 93/20061, WO 96/40126, WO 95/06037, WO 92/15567 and WO 94/17058. These imidazole derivatives differ structurally from the present compounds.

Furthermore, Helv. Chim. Acta 1979, 62(2), 507–10 discloses imidazole derivatives. However, they are neither disclosed nor suggested to possess histamine H3 receptor agonistic, inverse agonistic or antagonistic activity.

In view of the art's interest in histamine H3 receptor agonists, inverse agonists and antagonists, novel compounds which interact with the histamine H3 receptor would be a highly desirable contribution to the art. The present invention provides such a contribution to the art being based on the finding that a novel class of imidazo heterocyclic compounds has a high and specific affinity to the histamine H3 receptor.

Due to their interaction with the histamine H3 receptor, the present compounds are useful in the treatment and/or prevention of a wide range of conditions and disorders in which an interaction with the histamine H3 receptor is beneficial. Thus, the compounds may find use eg in the treatment of diseases of the central nervous system, the peripheral nervous system, the cardiovascular system, the pulmonary system, the gastrointestinal system and the endocrinological system.

DEFINITIONS

The following is a detailed definition of the terms used to describe the compounds of the invention.

"Halogen" designates an atom selected from the group consisting of F, Cl, Br and I.

The term "$C_{1-6}$-alkyl" in the present context designates a saturated, branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

The term "$C_{2-6}$-alkenyl" as used herein represents a branched or straight hydrocarbon group having from 2 to 6 carbon atoms and at least one double bond. Examples of such groups include, but are not limited to, vinyl, 1-propenyl, 2-propenyl, isopropenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "$C_{2-6}$-alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 5-hexynyl, 2,4-hexadiynyl and the like.

The term "$C_{1-6}$-alkoxy" in the present context designates a group —O—$C_{1-6}$-alkyl wherein $C_{1-6}$-alkyl is as defined above. Representative examples include, but are not limited to, methoxy, ethoxy, n-propoxy, isopropoxy, butoxy, isobutoxy, sec-butoxy, tert-butoxy, n-pentoxy, isopentoxy, neopentoxy, tert-pentoxy, n-hexoxy, isohexoxy and the like.

The term "$C_{1-6}$-alkylthio" in the present context designates a group —S—$C_{1-6}$-alkyl wherein $C_{1-6}$-alkyl is as defined above. Representative examples include, but are not limited to, methylthio, ethylthio, n-propylthio, isopropylthio, butylthio, isobutylthio, sec-butylthio, tert-butylthio, n-pentylthio, isopentylthio, neopentylthio, tert-pentylthio, n-hexylthio, isohexylthio and the like.

The term "$C_{1-6}$-alkylcarbonyl" in the present context designates a group —C(=O)—$C_{1-6}$-alkyl wherein $C_{1-6}$-alkyl is as defined above. Representative examples include, but are not limited to, methylcarbonyl, ethylcarbonyl, n-propylcarbonyl, isopropylcarbonyl, butylcarbonyl, isobutylcarbonyl, sec-butylcarbonyl, tert-butylcarbonyl, n-pentylcarbonyl, isopentylcarbonyl, neopentylcarbonyl, tert-pentylcarbonyl, n-hexylcarbonyl, isohexylcarbonyl and the like.

The term "$C_{1-6}$-alkylsulfonyl" in the present context designates a group —S(=O)$_2$—$C_{1-6}$-alkyl wherein $C_{1-6}$-alkyl is as defined above. Representative examples include, but are not limited to, methylsulfonyl, ethylsulfonyl, n-propylsulfonyl, isopropylsulfonyl, butylsulfonyl, isobutylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl and the like.

The term "$C_{3-10}$-cycloalkyl" as used herein represents a saturated mono-, bi-, tri- or spirocarbocyclic group having from 3 to 10 carbon atoms. Representative examples are cyclopropyl, cyclobutyl, cyclopentyl, cyclohexyl, cycloheptyl, cyclooctyl, cyclononyl, cyclodecyl, bicyclo[3.2.1]octyl, spiro[4.5]decyl, norpinyl, norbonyl, norcaryl, adamantyl and the like.

The term "$C_{3-10}$-cycloalkylcarbonyl" as used herein represents a group —C(=O)—$C_{3-10}$-cycloalkyl wherein $C_{3-10}$-cycloalkyl is as defined above.

The term "$C_{3-8}$-heterocyclyl" as used herein represents a saturated 3 to 8 membered ring containing one or more heteroatoms selected from nitrogen, oxygen and sulfur. Representative examples are pyrrolidyl, piperidyl, piperazinyl, morpholinyl, thiomorpholinyl, aziridinyl, tetrahydrofuranyl and the like.

The term "aryl" as used herein represents a carbocyclic aromatic ring system such as phenyl, biphenyl, naphthyl, anthracenyl, phenanthrenyl, fluorenyl, indenyl, pentalenyl, azulenyl, biphenylenyl and the like. Aryl is also intended to include the partially hydrogenated derivatives of the carbocyclic aromatic systems enumerated above. Non-limiting examples of such partially hydrogenated derivatives are 1,2,3,4-tetrahydronaphthyl, 1,4-dihydronaphthyl and the like.

The term "aroyl" as used herein represents a group —C(=O)-aryl wherein aryl is as defined above.

The term "arylthio" as used herein represents a group —S-aryl wherein aryl is as defined above.

The term "aryloxy" as used herein represents a group —O-aryl wherein aryl is as defined above.

The term "arylsulfonyl" as used herein represents a group —S(=O)$_2$-aryl wherein aryl is as defined above.

The term "arylamino" as used herein represents a group —NH-aryl wherein aryl is as defined above.

The term "aryl annulated with $C_{3-8}$-heterocyclyl" as used herein represents a ring system which contains an aryl group as defined herein to which a $C_{3-8}$-heterocyclyl group as defined herein is attached and which does not fall under the below definiton of heteroaryl. The aryl group and the heterocyclyl group may form fused, bridged or spirocyclic ring systems. Representative examples are 2,3-methylenedioxyphenyl, 3,4-methylenedioxyphenyl, 2,4-methylenedioxyphenyl, 2,5-methylenedioxyphenyl, 3,5-methylenedioxyphenyl, 3,6-methylenedioxyphenyl, chromanyl, isochromanyl, 2,3-ethylenedioxyphenyl, 3,4-ethylenedioxyphenyl, 2,4-ethylenedioxyphenyl, 2,5-ethylenedioxyphenyl, 3,5-ethylenedioxyphenyl, 3,6-ethylenedioxyphenyl and the like.

The term "heteroaryl" as used herein represents a heterocyclic aromatic ring system containing one or more heteroatoms selected from nitrogen, oxygen and sulfur such as furanyl, thiophenyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5- triazinyl, 1,2,3-oxadiazolyl, 1,2,4-oxadiazolyl, 1,2,5-oxadiazolyl, 1,3, 4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl (thianaphthenyl), indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

The term "heteroaroyl" as used herein represents a group —C(=O)-heteroaryl wherein heteroaryl is as defined above.

The term "heteroarylthio" as used herein represents a group —S-heteroaryl wherein heteroaryl is as defined above.

The term "heteroaryloxy" as used herein represents a group —O-heteroaryl wherein heteroaryl is as defined above.

The term "heteroarylsulfonyl" as used herein represents a group —S(=O)$_2$-heteroaryl wherein heteroaryl is as defined above.

The term "heteroarylamino" as used herein represents a group —NH-heteroaryl wherein heteroaryl is as defined above.

"Aryl-$C_{1-6}$-alkyl", "heteroaryl-$C_{1-6}$-alkyl" etc. means $C_{1-6}$-alkyl as defined above, substituted by an aryl or heteroaryl as defined above, for example:

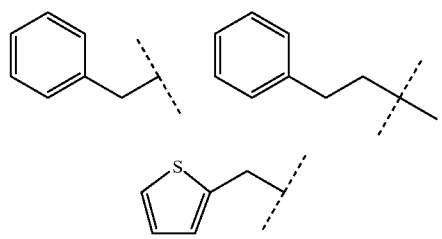

In connection with the terms "—C(=NOR$^7$)$C_{1-6}$-alkyl", "—C(=NOR$^7$)$C_{3-10}$-cycloalkyl", "—C(=NOR$^7$)aryl" and "—C(=NOR$^7$)heteroaryl" as used herein it should be understood that the substituents are attached via the carbon atom, for example as follows:

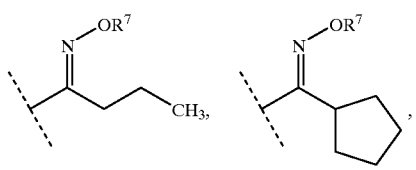

-continued

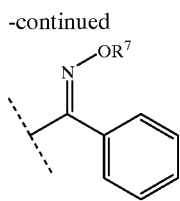

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

As used herein, the phrase "a functional group which can be converted to hydrogen in vivo" is intended to include any group which upon administering the present compounds to the subjects in need thereof can be converted to hydrogen eg enzymatically or by the acidic environment in the stomach. Non-limiting examples of such groups are acyl, carbamoyl, monoalkylated carbamoyl, dialkylated carbamoyl, alkoxycarbonyl, alkoxyalkyl groups and the like such as $C_{1-6}$-alkylcarbonyl, aroyl, $C_{1-6}$-alkylcarbamoyl, di-$C_{1-6}$-alkylcarbamoyl, $C_{1-6}$-alkoxycarbonyl and $C_{1-6}$-alkoxy-$C_{1-6}$-alkyl.

As used herein, the phrase "diseases and disorders related to the histamine H3 receptor" is intended to include any disease or disorder in which an effect, either antagonistic or agonistic, on the histamine H3 receptor is beneficial.

DETAILED DESCRIPTION OF THE INVENTION

The present invention relates to a compound of the general formula (I):

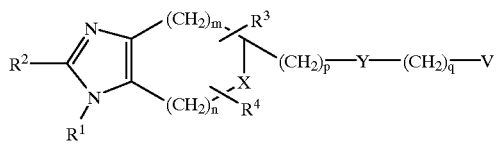

(I)

wherein $R^1$ is hydrogen or a functional group, which can be converted to hydrogen in vivo, $R^2$ is hydrogen, $C_{1-6}$-alkyl, $C_{1-6}$-alkoxy, $C_{1-6}$-alkylthio, halogen, cyano, trifluoromethyl, hydroxy, thiol or —$NR^5R^6$, wherein $R^5$ and $R^6$ independently are hydrogen or $C_{1-6}$-alkyl, $R^3$ and $R^4$ independently are hydrogen or $C_{1-6}$-alkyl, which is optionally substituted with aryl or heteroaryl, which are optionally substituted with one or more substituents selected from nitro, —$NR^7R^8$, —$S(=O)_2NR^7R^8$, —$C(=O)NR^7R^8$, hydroxy, halogen, cyano, trifluoromethyl, —$OCF_3$, —$OCHF_2$, —$OCH_2CHF_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —$C(=O)OR^7$, $C_{1-6}$-alkylcarbonyl, —$C(=NOR^7)C_{1-6}$alkyl, $C_{3-10}$-cycloalkyl, $C_{3-10}$-cycloalkylcarbonyl, —$C(=NOR^7)C_{3-10}$-cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, —$C(=NOR^7)$aryl, —$C(=NOR^7)$heteroaryl, arylthio, heteroarylthio, aryloxy and heteroaryloxy, wherein $R^7$ and $R^8$ independently are hydrogen or $C_{1-6}$-alkyl, m is 0, 1 or 2, n is 1, 2, 3 or 4, X is a valence bond, —O—, —S—, —S(=O)—, —S(=O)$_2$— or —$CF_2$—, p is 0, 1, 2 or 3, Y is —O—, —S—, —S(=O)—, —S(=O)$_2$— or —$NR^9$—, wherein $R^9$ is hydrogen or $C_{1-6}$-alkyl, q is 0, 1, 2 or 3, V is heteroaryl, aryl, $C_{3-10}$-cycloalkyl, $C_{3-8}$-heterocyclyl or aryl annulated with $C_{3-8}$-heterocyclyl, which are optionally substituted with one or more substituents selected from nitro, —$NR^{10}R^{11}$, —$S(=O)_2NR^{10}R^{11}$, —$C(=O)NR^{10}R^{11}$, hydroxy, halogen, cyano, trifluoromethyl, —$OCF_3$, —$OCHF_2$, —$OCH_2CHF_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —$C(=O)OR^{10}$, $C_{1-6}$-alkylcarbonyl, —$C(=NOR^{10})C_{1-6}$-alkyl, oxo, $C_{3-10}$-cycloalkyl, $C_{3-10}$-cycloalkylcarbonyl, —$C(=NOR^{10})C_{3-10}$-cycloalkyl, heteroaryl-$C_{1-6}$-alkyl, arylamino, heteroarylamino, aroyl, heteroaroyl, arylsulfonyl, heteroarylsulfonyl, —$C(=NOR^{10})$aryl, —$C(=NOR^{10})$heteroaryl, arylthio, heteroarylthio, and heteroaryloxy, wherein $R^{10}$ and $R^{11}$ independently are hydrogen or $C_{1-6}$-alkyl, aryl-$C_{1-6}$-alkyl, aryl or aryloxy, which are optionally substituted with one or more substituents selected from nitro, hydroxy, $C_{1-6}$-alkyl, $C_{1-6}$-alkoxy, cyano, trifluoromethyl, —$OCF_3$, halogen $C_{1-6}$-alkyl, $C_{2-6}$-alkenyl or $C_{2-6}$-alkynyl, which are optionally substituted with one or more substituents selected from $C_{3-10}$-cycloalkyl, aryl, $C_{3-8}$-heterocyclyl and heteroaryl, which are optionally substituted with one or more substituents selected from nitro, —$NR^{12}R^{13}$, —$S(=O)_2NR^{12}R^{13}$, —$C(=O)NR^{12}R^{13}$, hydroxy, halogen, cyano, trifluoromethyl, —$OCF_3$, —$OCHF_2$, —$OCH_2CHF_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —$C(=O)OR^{12}$, $C_{1-6}$-alkylcarbonyl, —$C(=NOR^{12})C_{1-6}$-alkyl, $C_{3-10}$-cycloalkyl, $C_{3-10}$-cycloalkylcarbonyl, —$C(=NOR^{12})C_{3-10}$-cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, —$C(=NOR^{12})$aryl, —$C(=NOR^{12})$heteroaryl, arylthio, heteroarylthio, aryloxy and heteroaryloxy, wherein $R^{12}$ and $R^{13}$ independently are hydrogen or $C_{1-6}$-alkyl, with the proviso that when $R^1$, $R^2$, $R^3$ and $R^4$ are hydrogen, X is a valence bond, m is 0, n is 3, p is 0 and Y is —S—, —$(CH_2)_q$—V must not be —$(CH_2)_2$—$NH_2$, as well as any optical or geometric isomer or tautomeric form thereof including mixtures of these or a pharmaceutically acceptable salt thereof.

In another aspect the present invention relates to a compound of the general formula (I"):

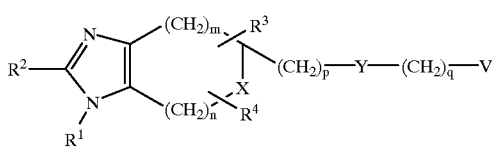

(I″)

wherein

R¹ is hydrogen or a functional group, which can be converted to hydrogen in vivo, R² is hydrogen, $C_{1-6}$-alkyl, $C_{1-6}$-alkoxy, $C_{1-6}$-alkylthio, halogen, cyano, trifluoromethyl, hydroxy, thiol or —NR⁵R⁶, wherein R⁵ and R⁶ independently are hydrogen or $C_{1-6}$-alkyl, R³ and R⁴ independently are hydrogen or $C_{1-6}$-alkyl, which is optionally substituted with aryl or heteroaryl, which are optionally substituted with one or more substituents selected from nitro, —NR⁷R⁸, —S(=O)₂R⁷R⁸, —C(=O)R⁷R⁸, hydroxy, halogen, cyano, trifluoromethyl, —OCF₃, —OCHF₂, —OCH₂CHF₂, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —C(=O)OR⁷, $C_{1-6}$-alkylcarbonyl, —C(=NOR⁷)$C_{1-6}$-alkyl, $C_{3-10}$-cycloalkyl, $C_{3-10}$-cycloalkylcarbonyl, —C(=NOR⁷)$C_{3-10}$-cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, —C(=NOR⁷)aryl, —C(=NOR⁷)heteroaryl, arylthio, heteroarylthio, aryloxy and heteroaryloxy, wherein R⁷ and R⁸ independently are hydrogen or $C_{1-6}$-alkyl, m is 0, 1 or 2, n is 1, 2, 3 or 4, X is a valence bond, —O—, —S—, —S(=O)—, —S(=O)₂— or —CF₂—, p is 0, 1, 2 or 3, Y is —O—, —S—, —S(=O)—, —S(=O)₂— or —NR⁹—, wherein R⁹ is hydrogen or $C_{1-6}$-alkyl, q is 0, 1, 2 or 3, V is heteroaryl, aryl, $C_{3-10}$-cycloalkyl, $C_{3-8}$-heterocyclyl or aryl annulated with $C_{3-8}$-heterocyclyl, which are optionally substituted with one or more substituents selected from nitro, —NR¹⁰R¹¹, —S(=O)₂NR¹⁰R¹¹, —C(=O)NR¹⁰R¹¹, hydroxy, halogen, cyano, trifluoromethyl, —OCF₃, —OCHF₂, —OCH₂CHF₂, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —C(=O)OR¹⁰, $C_{1-6}$-alkylcarbonyl, —C(=NOR¹⁰)$C_{1-6}$-alkyl, $C_{3-10}$-cycloalkyl, $C_{3-10}$-cycloalkylcarbonyl, —C(=NOR¹⁰)$C_{3-10}$-cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, —C(=NOR¹⁰)aryl, —C(=NOR¹⁰)heteroaryl, arylthio, heteroarylthio, aryloxy and heteroaryloxy, wherein R¹⁰ and R¹¹ independently are hydrogen or $C_{1-6}$-alkyl, $C_{1-6}$-alkyl, $C_{2-6}$-alkenyl or $C_{2-6}$-alkynyl, which are optionally substituted with one or more substituents selected from $C_{3-10}$-cycloalkyl, aryl, $C_{3-8}$-heterocyclyl and heteroaryl, which are optionally substituted with one or more substituents selected from nitro, —NR¹²R¹³, —S(=O)₂NR¹²R¹³, —C(=O)NR¹²R¹³, hydroxy, halogen, cyano, trifluoromethyl, —OCF₃, —OCHF₂, —OCH₂CHF₂, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —C(=O)OR¹², $C_{1-6}$-alkylcarbonyl, —C(=NOR¹²)$C_{1-6}$-alkyl, $C_{3-10}$-cycloalkyl, $C_{3-10}$-cycloalkylcarbonyl, —C(=NOR¹²)$C_{3-10}$-cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, —C(=NOR¹²)aryl, —C(=NOR¹²)heteroaryl, arylthio, heteroarylthio, aryloxy and heteroaryloxy, wherein R¹² and R¹³ independently are hydrogen or $C_{1-6}$-alkyl, with the proviso that when R¹, R², R³ and R⁴ are hydrogen, X is a valence bond, m is 0, n is 3, p is 0 and Y is —S—, —(CH₂)$_q$—V must not be —(CH₂)₂—NH₂, as well as any optical or geometric isomer or tautomeric form thereof including mixtures of these or a pharmaceutically acceptable salt thereof.

Preferably, R¹ is hydrogen.

R² is also preferably hydrogen.

Preferably, R³ and R⁴ are both hydrogen.

In a preferred embodiment m is 1 and n is 2.

In another preferred embodiment m is 0 and n is 3 or 4.

In yet another preferred embodiment m is 1 and n is 1.

p is preferably 1 or 2.

X is preferably a valence bond or —O—.

Y is preferably —O—.

q is preferably 0 or 1.

In a preferred embodiment V is selected from heteroaryl, aryl and aryl annulated with $C_{3-8}$-heterocyclyl, which are optionally substituted as defined for formula (I).

Preferably, V is selected from aryl and aryl annulated with $C_{3-8}$-heterocyclyl, which are optionally substituted as defined as for formula (I).

More preferably, V is selected from phenyl, naphthyl, tetrahydronaphthyl and 3,4-methylenedioxyphenyl, which are optionally substituted as defined for formula (I).

Even more preferably, V is selected from phenyl and naphthyl, which are optionally substituted as defined for formula (I).

Preferably, V is unsubstituted or substituted with one or two substituents independently selected from halogen, $C_{3-10}$-cycloalkylcarbonyl, cyano, $C_{1-6}$-alkylcarbonyl, —C(=O)OR¹⁰, $C_{1-6}$-alkyl, $C_{1-6}$-alkoxy, —CF₃ and —OCF₃, wherein R¹⁰ is as defined for formula (I) above, aryl-$C_{1-6}$-alkyl, aryl and aryloxy, which are optionally substituted as defined for formula (I) above.

More preferably, V is unsubstituted or substituted with one or two substituents independently selected from halogen, $C_{3-10}$-cycloalkylcarbonyl, cyano, $C_{1-6}$-alkylcarbonyl, —C(=O)OR¹⁰, $C_{1-6}$-alkyl, $C_{1-6}$-alkoxy, —CF₃ and —OCF₃, wherein R¹⁰ is as defined for formula (I) above, phenyl-$C_{1-6}$-alkyl, phenyl and phenoxy, which are optionally substituted as defined for formula (I) above.

Even more preferably, V is unsubstituted or substituted with one or two substituents independently selected from phenyl, phenoxy and trifluoromethyl.

In another preferred embodiment V is $C_{1-6}$-alkyl or $C_{2-6}$-alkenyl, which is optionally substituted as defined for formula (I) above.

Preferably, V is $C_{1-6}$-alkyl or $C_{2-6}$-alkenyl, which is substituted with aryl, which is optionally substituted as defined for formula (I) above.

More preferably, V is $C_{1-6}$-alkyl or $C_{2-6}$-alkenyl, which is substituted with phenyl, which is optionally substituted as defined for formula (I) above.

In a preferred embodiment the invention relates to a compound of the general formula (Ie):

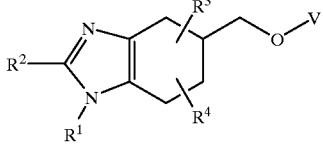
(Ie)

wherein $R^1$, $R^2$, $R^3$, $R^4$ and V are as defined for formula (I) or in any of the above preferred embodiments.

In another preferred embodiment the invention relates to a compound of the general formula (If):

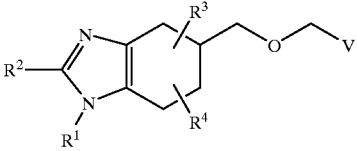
(If)

wherein $R^1$, $R^2$, $R^3$, $R^4$ and V are as defined are as defined for formula (I) or in any of the above preferred embodiments.

In still another preferred embodiment the invention relates to a compound of the general formula (Ig):

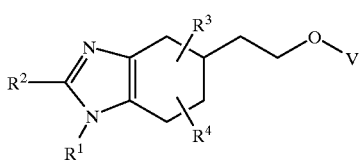
(Ig)

wherein $R^1$, $R^2$, $R^3$, $R^4$ and V are as defined are as defined for formula (I) or in any of the above preferred embodiments.

In yet another preferred embodiment the invention relates to a compound of the general formula (Ih):

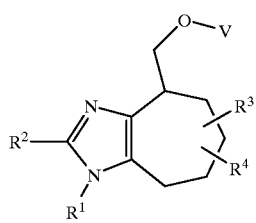
(Ih)

wherein $R^1$, $R^2$, $R^3$, $R^4$ and V are as defined are as defined for formula (I) or in any of the above preferred embodiments.

In a further preferred embodiment the invention relates to a compound of the general formula (Ii):

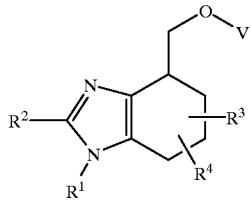
(Ii)

wherein $R^1$, $R^2$, $R^3$, $R^4$ and V are as defined are as defined for formula (I) or in any of the above preferred embodiments.

The following compounds are within the scope of the present invention:
2-(4,5,6,7-tetrahydro-1H-benzimidazol-5-ylmethoxy) benzonitrile,
5-(4-chlorophenoxymethyl)-4,5,6,7-tetrahydro-1H-benzimidazole,
cyclopropyl-(4-(4,5,6,7-tetrahydro-1H-benzimidazol-5-ylmethoxy)methanone,
5-(naphth-1-yloxymethyl)-4,5,6,7-tetrahydro-1H-benzimidazole,
5-(naphth-2-yloxymethyl)-4,5,6,7-tetrahydro-1H-benzimidazole,
5-(5,6,7,8-tetrahydronaphth-2-yloxymethyl)-4,5,6,7-tetrahydro-1H-benzimidazole,
5-(3-chlorophenoxymethyl)-4,5,6,7-tetrahydro-1H-benzimidazole,
3-(4,5,6,7-tetrahydro-1H-benzimidazol-5-ylmethoxy) benzonitrile,
5-(4-benzylphenoxymethyl)-4,5,6,7-tetrahydro-1H-benzimidazole,
5-(3,4-methylenedioxyphenoxymethyl)-4,5,6,7-tetrahydro-1H-benzimidazole,
4-(4,5,6,7-tetrahydro-1H-benzimidazol-5-ylmethoxy) benzoic acid ethyl ester,
5-(2,4-difluorophenoxymethyl)-4,5,6,7-tetrahydro-1H-benzimidazole,
5-(2-chlorophenoxymethyl)-4,5,6,7-tetrahydro-1H-benzimidazole,
5-(2-iodophenoxymethyl)-4,5,6,7-tetrahydro-1H-benzimidazole,
5-(2-trifluoromethyl-phenoxymethyl)-4,5,6,7-tetrahydro-1H-benzimidazole,
5-(2-fluorophenoxymethyl)-4,5,6,7-tetrahydro-1H-benzimidazole,
5-(3-trifluoromethoxyphenoxymethyl)-4,5,6,7-tetrahydro-1H-benzimidazole,
5-(biphenyl-3-yloxymethyl)-4,5,6,7-tetrahydro-1H-benzimidazole,
5-(3-trifluoromethylphenoxymethyl)-4,5,6,7-tetrahydro-1H-benzimidazole,
5-(2,6-difluorophenoxymethyl)-4,5,6,7-tetrahydro-1H-benzimidazole,
5-(4-trifluoromethoxyphenoxymethyl)-4,5,6,7-tetrahydro-1H-benzimidazole,
4-(2-ethylphenoxymethyl)-4,5,6,7-tetrahydro-1H-benzimidazole,
4-(4-cyanophenoxymethyl)-4,5,6,7-tetrahydro-1H-benzimidazole,
4-(1-naphthyloxymethyl)-4,5,6,7-tetrahydro-1H-benzimidazole,
4-(2-chlorophenoxymethyl)-4,5,6,7-tetrahydro-1H-benzimidazole, 4-(2-chlorophenoxymethyl)-1,4,5,6,7,8-hexahydrocycloheptaimidazole,
4-(2,4-difluorophenoxymethyl)-4,5,6,7-tetrahydro-1H-benzimidazole,
4-(2,4-difluorophenoxymethyl)-1,4,5,6,7,8-hexahydrocycloheptaimidazole,
4-(3-acetylphenoxymethyl)-1,4,5,6,7,8-hexahydrocycloheptaimidazole,
5-[2-(2,4-dichlorophenoxy)ethyl]-4,5,6,7-tetrahydro-1H-benzimidazole,
5-[2-(3-phenoxyphenoxy)ethyl]-4,5,6,7-tetrahydro-1H-benzimidazole,
5-[2-(naphth-1-yloxy)ethyl]-4,5,6,7-tetrahydro-1H-benzimidazole,
5-[2-(biphenyl-2-yloxy)ethyl]-4,5,6,7-tetrahydro-1H-benzimidazole,
5-[3-($^4$-chlorophenoxy)propyl]-4,5,6,7-tetrahydro-1H-benzimidazole,
4-[3-(4,5,6,7-tetrahydro-1H-benzimidazol-5-yl)propoxy]benzonitrile,
5-(2-benzyloxyethyl)-4,5,6,7-tetrahydro-1H-benzimidazole,
5-benzyloxy-4,5,6,7-tetrahydro-1H-benzimidazole,
5-((biphenyl-2-yl)methoxymethyl)-4,5,6,7-tetrahydro-1H-benzimidazole,
5-((1-naphthyl)methoxymethyl)-4,5,6,7-tetrahydro-1H-benzimidazole,
5-(4-trifluoromethylbenzyloxymethyl)-4,5,6,7-tetrahydro-1H-benzimidazole,
5-((3-(trifluoromethyl)benzyloxy)methyl)-4,5,6,7-tetrahydro-1H-benzimidazole,
5-((2-phenoxybenzyloxy)methyl)-4,5,6,7-tetrahydro-1H-benzimidazole,
6-phenoxymethyl-3,4,6,7-tetrahydropyrano[3,4-d]imidazole,
5-allyloxymethyl-4,5,6,7-tetrahydro-1H-benzimidazole,
5-(((2-naphthyl)methoxy)methyl)-4,5,6,7-tetrahydro-1H-benzimidazole,
5-(2-chloro-5-trifluoromethylbenzyloxymethyl)-4,5,6,7-tetrahydro-1H-benzimidazole,
(E)-5-(3-phenylallyloxymethyl)-4,5,6,7-tetrahydro-1H-benzimidazole,
5-((biphenyl-4-yl)methoxymethyl)-4,5,6,7-tetrahydro-1H-benzimidazole,
5-(3-phenylpropoxymethyl)-4,5,6,7-tetrahydro-1H-benzimidazole,
5-(2-chloro-3-(trifluoromethyl)benzyloxymethyl)-4,5,6,7-tetrahydro-1H-benzimidazole,
3-(((4,5,6,7-tetrahydro-1H-benzimidazol-5-yl)methoxy)methyl)benzonitrile,
5-(4-phenylbutoxymethyl)-4,5,6,7-tetrahydro-1H-benzimidazole,
5-[(2-(2,4-dichlorophenoxy)benzyloxy)methyl]-4,5,6,7-tetrahydro-1H-benzimidazole
5-[2-(4-fluorobenzyl)benzyloxymethyl]-4,5,6,7-tetrahydro-1H-benzimidazole,
5-[2-(3-(trifluoromethoxy)phenoxy)benzyloxymethyl]-4,5,6,7-tetrahydro-1H-benzimidazole,
5-((5-phenylpentyloxy)methyl)-4,5,6,7-tetrahydro-1H-benzimidazole,
4-(1,4,5,6,7,8-hxahydrocycloheptaimidazol-4-ylmethoxy)benzonitrile,
4-(4-trifluoromethoxyphenoxymethyl)-4,5,6,7-tetrahydro-1H-benzimidazole,
4-(4-trifluoromethylphenoxymethyl)-4,5,6,7-tetrahydro-1H-benzimidazole,
3,5-dimethyl-4-(4,5,6,7-tetrahydro-1H-benzimidazol-4-ylmethoxy)benzonitrile,
3-chloro-4-(4,5,6,7-tetrahydro-1H-benzimidazol-4-ylmethoxy)benzonitrile,
3-(4,5,6,7-tetrahydro-1H-benzimidazol-4-ylmethoxy)benzonitrile,
cyclopropyl-[4-(4,5,6,7-tetrahydro-1H-benzimidazol-4-ylmethoxy)phenyl]methanone,
3-methoxy-4-(4,5,6,7-tetrahydro-1H-benzimidazol-4-ylmethoxy)benzonitrile,
5-(4,5,6,7-tetrahydro-1H-benzimidazol-4-ylmethoxy)-3,4-dihydro-2H-naphthalen-1-one,
4-(4-chlorophenoxymethyl)-4,5,6,7-tetrahydro-1H-benzimidazole,
[5-chloro-2-(4,5,6,7-tetrahydro-1H-benzimidazol-4-ylmethoxy)phenyl]phenylmethanone,
as well as any optical or geometric isomer or tautomeric form thereof including mixtures of these or a pharmaceutically acceptable salt thereof.

The compounds of the present invention may have one or more asymmetric centres and it is intended that any optical isomers, as separated, pure or partially purified optical isomers or racemic mixtures thereof are included within the scope of the invention.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates, which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds of the present invention interact with the histamine H3 receptor and are accordingly useful for the treatment and/or prevention of a wide variety of conditions and disorders in which histamine H3 receptor interactions are beneficial.

Accordingly, in another aspect the present invention relates to compounds of the general formula (I'):

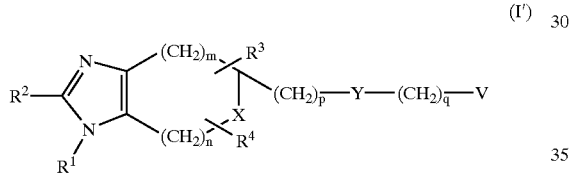

(I')

wherein $R^1$ is hydrogen or a functional group, which can be converted to hydrogen in vivo, $R^2$ is hydrogen, $C_{1-6}$-alkyl, $C_{1-6}$-alkoxy, $C_{1-6}$-alkylthio, halogen, cyano, trifluoromethyl, hydroxy, thiol or —$NR^5R^6$, wherein $R^5$ and $R^6$ independently are hydrogen or $C_{1-6}$-alkyl, $R^3$ and $R^4$ independently are hydrogen or $C_{1-6}$-alkyl, which is optionally substituted with aryl or heteroaryl, which are optionally substituted with one or more substituents selected from nitro, —$NR^7R^8$, —$S(=O)_2NR^7R^8$, —$C(=O)NR^7R^8$, hydroxy, halogen, cyano, trifluoromethyl, —$OCF_3$, —$OCHF_2$, —$OCH_2CHF_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —$C(=O)OR^7$, $C_{1-6}$-alkylcarbonyl, —$C(=NOR^7)C_{1-6}$-alkyl, $C_{3-10}$-cycloalkyl, $C_{3-10}$-cycloalkylcarbonyl, —$C(=NOR^7)C_{3-10}$-cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, —$C(=NOR^7)$aryl, —$C(=NOR^7)$heteroaryl, arylthio, heteroarylthio, aryloxy and heteroaryloxy, wherein $R^7$ and $R^8$ independently are hydrogen or $C_{1-6}$-alkyl, m is 0, 1 or 2, n is 1, 2, 3 or 4, X is a valence bond, —O—, —S—, —S(=O)—, —$S(=O)_2$— or —$CF_2$—, p is 0, 1, 2 or 3, Y is —O—, —S—, —S(=O)—, —$S(=O)_2$— or —$NR^9$—, wherein $R^9$ is hydrogen or $C_{1-6}$-alkyl, q is 0, 1, 2 or 3, V is heteroaryl, aryl, $C_{3-10}$-cycloalkyl, $C_{3-8}$-heterocyclyl or aryl annulated with $C_{3-8}$-heterocyclyl, which are optionally substituted with one or more substituents selected from nitro, —$NR^{10}R^{11}$, —$S(=O)_2NR^{10}R^{11}$, —$C(=O)NR^{10}R^{11}$, hydroxy, halogen, cyano, trifluoromethyl, —$OCF_3$, —$OCHF_2$, —$OCH_2CHF_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —$C(=O)OR^{10}$, —$C(=O)R^{10}$, $C_{1-6}$-alkylcarbonyl, —$C(=NOR^{10})C_{1-6}$-alkyl, oxo, $C_{3-10}$-cycloalkyl, $C_{3-10}$-cycloalkylcarbonyl, —$C(=NOR^{10})$-$C_{3-10}$-cycloalkyl, heteroaryl-$C_{1-6}$-alkyl, arylamino, heteroarylamino, aroyl, heteroaroyl, arylsulfonyl, heteroarylsulfonyl, —$C(=NOR^{10})$aryl, —$C(=NOR^{10})$heteroaryl, arylthio, heteroarylthio, and heteroaryloxy, wherein $R^{10}$ and $R^{11}$ independently are hydrogen or $C_{1-6}$-alkyl, aryl-$C_{1-6}$-alkyl, aryl or aryloxy, which are optionally substituted with one or more substituents selected from nitro, hydroxy, $C_{1-6}$-alkyl, $C_{1-6}$-alkoxy, cyano, trifluoromethyl, —$OCF_3$, halogen $C_{1-6}$-alkyl, $C_{2-6}$-alkenyl or $C_{2-6}$-alkynyl, which are optionally substituted with one or more substituents selected from $C_{3-10}$-cycloalkyl, aryl, $C_{3-8}$-heterocyclyl and heteroaryl, which are optionally substituted with one or more substituents selected from nitro, —$NR^{12}R^{13}$, —$S(=O)_2NR^{12}R^{13}$, —$C(=O)NR^{12}R^{13}$, hydroxy, halogen, cyano, trifluoromethyl, —$OCF_3$, —$OCHF_2$, —$OCH_2CHF_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —$C(=O)OR^{12}$, $C_{1-6}$-alkylcarbonyl, —$C(=NOR^{12})C_{1-6}$-alkyl, $C_{3-10}$-cycloalkyl, $C_{3-10}$-cycloalkylcarbonyl, —$C(=NOR^{12})C_{3-10}$-cycloalkyl, aryl-$C_{1-6}$-alkyl, heteroaryl-$C_{1-6}$-alkyl, arylamino, heteroarylamino, aroyl, heteroaroyl, arylsulfonyl, heteroarylsulfonyl, —$C(=NOR^{12})$aryl, —$C(=NOR^{12})$heteroaryl, arylthio, heteroarylthio, aryloxy and heteroaryloxy, wherein $R^{12}$ and $R^{13}$ independently are hydrogen or $C_{1-6}$-alkyl, as well as any optical or geometric isomer or tautomeric form thereof including mixtures of these or a pharmaceutically acceptable salt thereof as a pharmaceutical composition.

The invention also relates to pharmaceutical compositions comprising, as an active ingredient, at least one compound of the formula (I') or any optical or geometric isomer or tautomeric form thereof including mixtures of these or a pharmaceutically acceptable salt hereof together with one or more pharmaceutically acceptable carriers or diluents.

Furthermore, the invention relates to the use of a compound of the general formula (I') or any optical or geometric isomer or tautomeric form thereof including mixtures of these or a pharmaceutically acceptable salt thereof for the preparation of a pharmaceutical composition for the treatment and/or prevention of diseases and disorders related to the histamine H3 receptor.

In still another aspect, the invention relates to a method for the treatment and/or prevention of diseases and disorders related to the histamine H3 receptor the method comprising administering to a subject in need thereof an effective amount of a compound of the formula (I') or any optical or geometric isomer or tautomeric form thereof including mixtures of these or a pharmaceutically acceptable salt thereof or a pharmaceutical composition comprising the same.

In one aspect the invention relates to compounds with histamine H3 receptor antagonistic activity or inverse agonistic activity which may accordingly be useful in the treatment of a wide range of conditions and disorders in which histamine H3 receptor blockade is beneficial.

In another aspect the invention relates to compounds with histamine H3 receptor agonistic activity and which may accordingly be useful in the treatment of a wide range of conditions and disorders in which histamine H3 receptor activation is beneficial.

In a preferred embodiment of the invention the present compounds are used for the preparation of a pharmaceutical composition for the reduction of weight.

In a preferred embodiment of the invention the present compounds are used for the preparation of a pharmaceutical composition for the treatment and/or prevention of overweight or obesity.

In another preferred embodiment of the invention the present compounds are used for the preparation of a pharmaceutical composition for the suppression of appetite or satiety induction.

In a further preferred embodiment of the invention the present compounds are used for the preparation of a pharmaceutical composition for the prevention and/or treatment of disorders and diseases related to overweight or obesity such as atherosclerosis, hypertension, IGT (impaired glucose tolerance), diabetes, especially Type 2 diabetes (NIDDM (non-insulin dependent diabetes mellitus)), dyslipidaemia, coronary heart disease, gallbladder disease, osteoarthritis and various types of cancer such as endometrial, breast, prostate and colon cancers.

In yet a further preferred embodiment of the invention the present compounds are used for the preparation of a pharmaceutical composition for the prevention and/or treatment of eating disorders such as bulimia and binge eating.

In a further preferred embodiment of the invention the present compounds are used for the preparation of a pharmaceutical composition for the treatment and/or prevention of IGT.

In a further preferred embodiment of the invention the present compounds are used for the preparation of a pharmaceutical composition for the treatment and/or prevention of Type 2 diabetes.

In another preferred embodiment of the invention the present compounds are used for the preparation of a pharmaceutical composition for the delaying or prevention of the progression from IGT to Type 2 diabetes.

In a further preferred embodiment of the invention the present compounds are used for the preparation of a pharmaceutical composition for the delaying or prevention of the progression from non-insulin requiring Type 2 diabetes to insulin requiring Type 2 diabetes.

The compounds of the present invention may also be used for the treatment of air-way disorders such as asthma, as anti-diarrhoeals and for the modulation of gastric acid secretion.

Furthermore, the compounds of the present invention may be used for the treatment of diseases associated with the regulation of sleep and wakefulness and for the treatment of narcolepsy and attention deficit disorders.

Moreover, the compounds of the invention may be used as CNS stimulants or as sedatives.

The present compounds may also be used for the treatment of conditions associated with epilepsy. Additionally, the present compounds may be used for the treatment of motion sickness and vertigo. Furthermore, they may be useful as regulators of hypothalamohypophyseal secretion, antidepressants, modulators of cerebral circulation, and in the treatment of irritable bowel syndrome.

Further, the compounds of the present invention may be used for the treatment of dementia and Alzheimer's disease.

The compounds of the present invention may also be useful for the treatment of allergic rhinitis, ulcer or anorexia.

The compounds of the present invention may furthermore be useful for the treatment of migraine, see R. L. McLeod et al., *The Journal of Pharmacology and Experimental Therapeutics* 287 (1998), 43–50, and for the treatment of myocardial infarction, see C. J. Mackins and R. Levi, *Expert Opinion on Investigational Drugs* 9 (2000), 2537–2542.

The present novel compounds may also interact with the vanilloid receptors, the serotonin receptors, and the adrenergic receptors and may be useful for the treatment of diseases associated with these receptors. Hence, the compounds of the present invention may be vanilloid receptor agonists, and thus be useful for the treatment of obesity by enhancement of the metabolic rate and energy expenditure. Further, by virtue of their interaction with the vanilloid receptor the compounds of the present invention may be useful for the treatment of pain or neurogenic inflammation or inflammatory painful conditions.

In a further preferred embodiment of the invention the present compounds are used for the preparation of a pharmaceutical composition for the treatment and/or prevention of diseases and disorders related to the vanilloid receptor, such as for the treatment and/or prevention of pain, neurogenic inflammation or obesity.

Furthermore, the present compounds may interact with the 5-HT3 receptor (serotonin-3-receptor), the compounds of the present invention may be useful as antiemetics, in particular the chemotherapy-induced emesis. Further potential applications of 5-HT3 antagonists include treatment of central nervous system disorders such as anxiety, schizophrenia, drug abuse and withdrawal symptoms, and pathological and age-associated amnesia.

In a further preferred embodiment of the invention the present compounds are used for the preparation of a pharmaceutical composition for the treatment and/or prevention of diseases and disorders related to the serotonin-3 receptor (5-HT3), such as for the treatment of emesis.

Furthermore, the present compounds may interact with the adrenergic alpha-2-receptor and thus be useful for the treatment of hypertension and of conditions associated with overexpression or hypersensitization of the adrenergic alpha-2 receptor, especially obesity, withdrawal symptoms to an adrenergic alpha-2 agonist, neurological disorders (especially orthostatic hypotension), multiple system atrophy, diabetes mellitus, benign prostatic hyperplasia or drug induced sensitization of the adrenergic alpha-2 receptor. Moreover, the compounds of the present invention, by virtue of their interaction with the adrenergic alpha-2 receptor, may be useful as sedatives and hypnotics (sleep inducing agents) or as stimulants.

In a further preferred embodiment of the invention the present compounds are used for the preparation of a pharmaceutical composition for the treatment and/or prevention of diseases and disorders related to the alpha-2 adrenergic receptor, such as for use as a sleep inducing agent.

In a further aspect of the invention the present compounds are combined with diet and/or exercise.

In a further aspect of the invention the present compounds may be administered in combination with one or more further pharmacologically active substances in any suitable ratios. Such further active agents may be selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC$_4$ (melanocortin 4) agonists, MC$_3$ (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, opioid antagonists (such as naltrexone), exendin-4, GLP-1 and ciliary neurotrophic factor.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

In still another embodiment the antiobesity agent is phendimetrazine, diethylpropion, fluoxetine, bupropion, topiramate or ecopipam.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise imidazolines, sulphonylureas, biguanides, meglitinides, oxadiazolidinediones, thiazolidinediones, insulin sensitizers, α-glucosidase inhibitors, agents acting on the ATP-dependent potassium channel of the β-cells eg potassium channel openers such as those disclosed in WO 97/26265, WO 99/03861 and WO 00/37474 (Novo Nordisk A/S) which are incorporated herein by reference, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists.

In one embodiment of the invention the present compounds are administered in combination with insulin.

In a further embodiment of the invention the present compounds are administered in combination with a sulphonylurea eg tolbutamide, glibenclamide, glipizide, glimepiride, glicazide or glyburide.

In another embodiment of the invention the present compounds are administered in combination with a biguanide eg metformin.

In yet another embodiment of the invention the present compounds are administered in combination with a meglitinide eg repaglinide or senaglinide.

In still another embodiment of the invention the present compounds are administered in combination with a thiazolidinedione eg troglitazone, ciglitazone, pioglitazone, rosiglitazone or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer eg such as those disclosed in WO 99/19313, WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor eg miglitol or acarbose.

In another embodiment of the invention the present compounds are administered in combination with an agent acting on the ATP-dependent potassium channel of the β-cells eg tolbutamide, glibenclamide, glipizide, glicazide or repaglinide.

In yet another embodiment of the invention the present compounds may be administered in combination with nateglinide.

In still another embodiment of the invention the present compounds are administered in combination with an antilipidemic agent eg cholestyramine, colestipol, clofibrate, gemfibrozil, lovastatin, pravastatin, simvastatin, probucol or dextrothyroxine.

In another aspect of the invention, the present compounds are administered in combination with more than one of the above-mentioned compounds eg in combination with metformin and a sulphonylurea such as glyburide; a sulphonylurea and acarbose; nateglinide and metformin; acarbose and meformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with diet and/or exercise, one or more of the above-mentioned compounds and optionally one or more other active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the formula (I) contains a free base such salts are prepared in a conventional manner by treating a solution or suspension of a free base of the formula (I) with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the novel compounds of the formula (I) in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet, which may be prepared by conventional tabletting techniques, may contain:

| Core: | | |
|---|---|---|
| Active compound (as free compound or salt thereof) | | 5.0 mg |
| Lactosum Ph. Eur. | | 67.8 mg |
| Cellulose, microcryst. (Avicel) | | 31.4 mg |
| Amberlite ® IRP88* | | 1.0 mg |
| Magnesii stearas Ph. Eur. | | q.s. |
| Coating: | | |
| Hydroxypropyl methylcellulose | approx. | 9 mg |
| Mywacett 9-40 T** | approx. | 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with further pharmacologically active substances such as those described in the foregoing.

The preparation of the compounds of this invention can be realised in many different ways. The starting imidazole derivatives of the formula (II) may be prepared according to procedures described in literature (see eg Croat. Chem. Acta. 1973, 45, 297. J. Am. Chem. Soc. 1976, 98, 984). The other reactants are either known compounds or compounds, which may be prepared in analogy with the preparation of similar known compounds.

Method A

Compounds of the formula (Ia), wherein m, n and p are as defined for formula (I) and V is aryl or heteroaryl, which may optionally be substituted as defined for formula (I), may be prepared as outlined below:

A compound of the formula (V) wherein m, n and p are as defined above and Pg represents a protecting group like eg triphenylmethyl (trityl) and L represents a leaving group such as eg halogen or mesylate may be reacted with a compound of the formula (VI) wherein V and q are as defined above. This reaction is carried out in the presence of a strong base like eg sodium hydride in a suitable solvent like eg THF or DMF at a temperature of up to reflux for the solvent used for eg 1–200 hours. Removal of the trityl group from a compound of the formula (VII) is accomplished with dilute acid to give a compound of the formula (Ib).

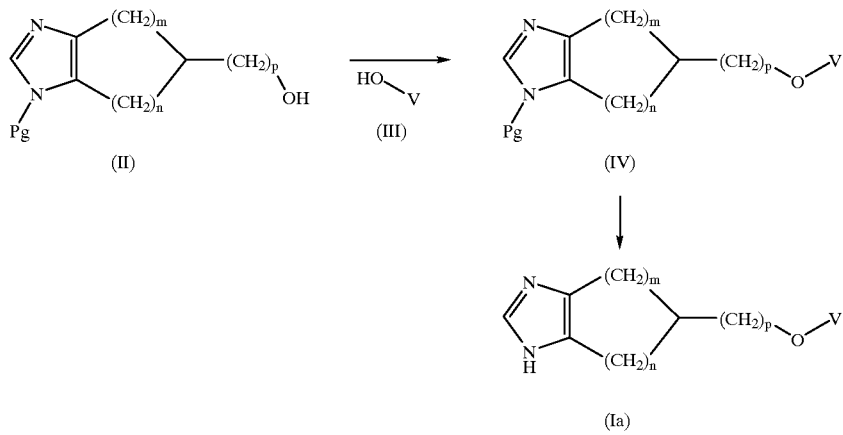

The alcohol of a compound of the formula (II) wherein m, n and p are as defined above and Pg represents a protecting group like eg triphenylmethyl (trityl) may be reacted with a compound of the formula (III) wherein V is as defined above. This reaction is carried out in the presence of a catalyst like eg triphenylphosphine and a base like eg diethyl azodicarboxylate in a suitable solvent like eg THF at a temperature of up to reflux for the solvent used for eg 1–200 hours. Removal of the trityl group of a compound of the formula (IV) is accomplished with dilute acid to give a compound of the formula Ia).

Method B

Compounds of the formula (Ib), wherein m, n, p and V are as defined for formula (I), may be prepared as outlined below:

Method C

A compound of the formula (Ic), wherein m, n, p, q, and V are defined as in formula (I), may be prepared as outlined below:

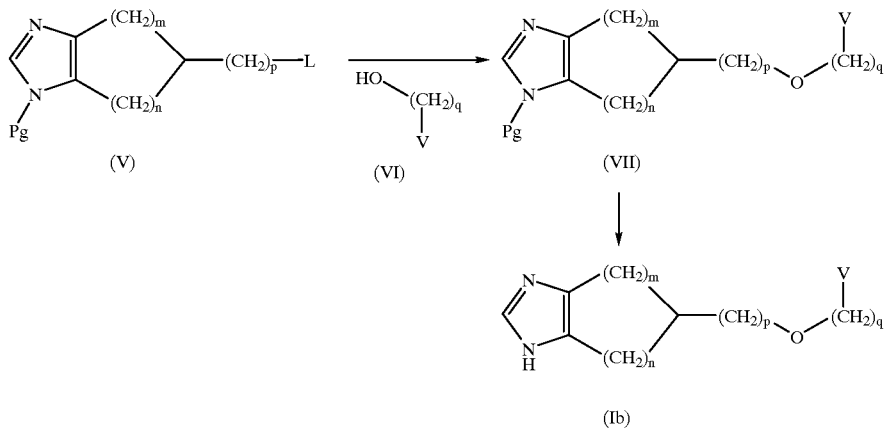

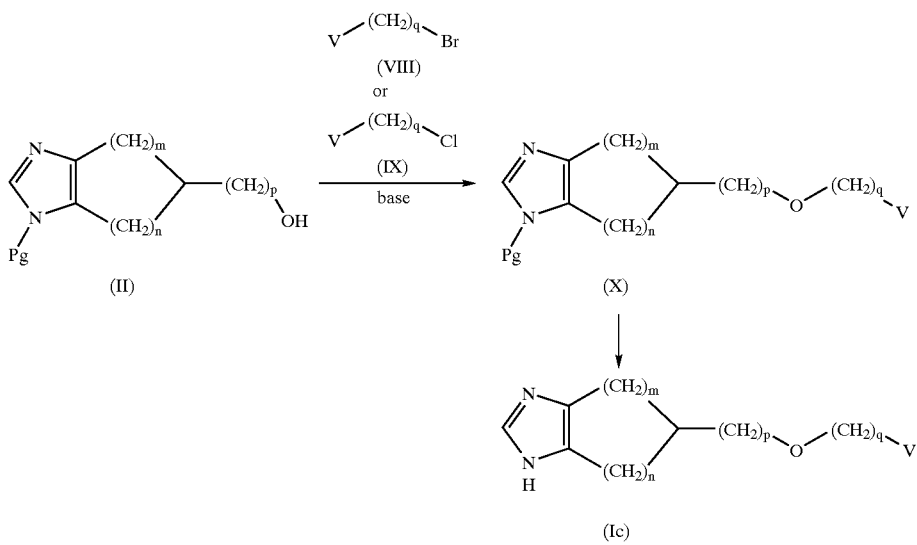

An alcohol of the formula (II), wherein m, n, and p are defined as in formula (I) and PG is a suitable protecting group as is described in the literature (eg T. W. Greene, P. G. M. Wuts, Protective groups in organic synthesis, $2^{nd}$ edition, John Wiley and Sons, Inc., New York) such as eg triphenylmethyl may be reacted with a suitable base such as eg sodium hydride, potassium hydride, lithium hydride in a suitable solvent such as tetrahydrofuran, ether or a hydrocarbon such as toluene or hexane. Successively a halogenide such as a bromide as shown in formula (VIII) or a chloride as shown in formula (IX) or a synthetic equivalent thereof may be reacted with the intermediate. Catalysts such as tetrabutylammonium iodide may be added optionally. The reaction temperature might be between −78° C. and the boiling point of the solvent applied for a reaction time of 0.5–200 hours. Removal of the protection group of a compound of the formula (X) may be accomplished as described in the literature (eg T. W. Greene, P. G. M. Wuts, Protective groups in organic synthesis, $2^{nd}$ edition, John Wiley and Sons, Inc., New York) eg a triphenylmethyl group may be removed with acid, such as acetic acid which may be diluted with another solvent such as water at a temperature between room temperature and 100° C.

Method D

A compound of the formula (Id), wherein n, m, p, q, X, Y, and V are defined as in formula (I), may be prepared as outlined below:

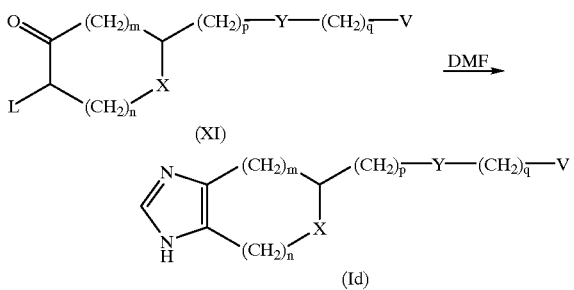

A cyclic ketone, of formula (XI) in which n, m, p, q and V are defined as in formula (I), and L is a leaving group such as bromo, chloro, or methansulfonyl, may be warmed with DMF to a suitable temperature such as a temperature between 100° C. and 200° C. for a time between 0.5 and 200 hours.

The present invention is further illustrated by the following representative examples, which are, however, not intended to limit the scope of the invention in any way.

EXAMPLES

In the examples the following terms are intended to have the following, general meanings:
CDI: carbonyldiimidazole
DBU: 1,8-diazabicyclo[5.4.0]undec-7-ene
DCM: dichloromethane, methylenechloride
DEAD: diethyl azodicarboxylate
DIC: diisopropylcarbodiimide
DIPEA: diisopropylethylamine
DMA: N,N-dimethylacetamide
DMF: N,N-dimethylformamide
DMSO: dimethyl sulfoxide
HOAt: 1-hydroxy-7-azabenzotriazole
NMP: N-methylpyrrolidin-2-one
TFA: trifluoroacetic acid
THF: tetrahydrofuran NMR spectra were recorded on Bruker 300 MHz and 400 MHz instruments. HPLC-MS was performed on a Perkin Elmer instrument (API 100), and HPLC-systems from Merck-Hitachi.

HPLC method A

Hibar™ RT 250-4, Lichrosorb™ RP-18, 5.0 μm, 4.0×125 mm; gradient elution, 5% to 80% solvent B (0.1% TFA in acetonitrile) in solvent A (0.1% TFA in water) within 15 min, 2.0 ml/min, detection at 214 nm, temperature 35° C.

HPLC method B

LiChroCART LiChrospher™ 100 RP-18, 5.0 μm, 4.0× 250 mm; gradient elution, 25% to 80% solvent B (0.1% TFA in acetonitrile) in solvent A (0.1% TFA in water) within 20 min, 2.0 ml/min, detection at 214 nm, temperature 35° C.

HPLC method C

218TP54 C-18 silica column, 4.6 mm×150 mm; linear gradient elution from 5% acetonitrile, 85% water and 10% of a solution of 0.5% TFA in water to 90% acetonitrile and 10% of a solution of 0.5% TFA in water within 15 min, 1 ml/min, detection at 214 nm, temperature 42° C.

HPLC method D

Hibar™ RT 250-4, Lichrosorb™ RP-18, 5.0 μm, 4.0×250 mm; gradient elution, 20% to 80% solvent B (0.1% TFA in acetonitrile) in solvent A (0.1% TFA in water) within 30 min, 1.0 ml/min, detection at 214 nm, temperature 30° C.

HPLC method E

Hibar™ RT 125-4, 5.0 μm, 4.0×125 mm; gradient elution, 5% to 80% solvent B (0.1% TFA in acetonitrile) in solvent A (0.1% TFA in water) within 10 min, 2.0 ml/min, detection at 214 nm, temperature 35° C.

Example 1

2-(4,5,6,7-Tetrahydro-1 H-benzimidazol-5-ylmethoxy) benzonitrile, Oxalic Acid Salt

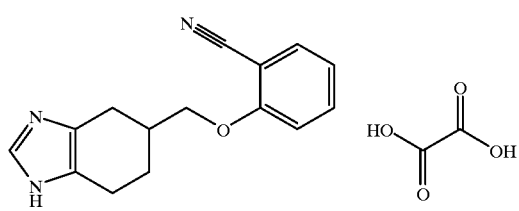

Step 1: 4,5,6,7-Tetrahydro-1H-benzimidazole-5-carboxylic Acid, Hydrochloride Salt

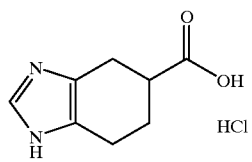

A solution of benzimidazole-5-carboxylic acid (10 g, 62 mmol) in 1 N HCl (70 ml) and H₂O (30 ml) was hydrogenated at 100 bar and 80° C. in the presence of 10% palladium on carbon (2.5 g) for 2 days. The mixture was filtered and the solvent was evaporated. The residue was stirred with acetone (100 ml) and the solid was isolated and dried. This afforded 10.6 g (79%) of 4,5,6,7-tetrahydro-1H-benzimidazole-5-carboxylic acid hydrochloride.

Mp. 248–250° C.; Lit Mp. 137° C. (Croat. Chem. Acta. 1973, 45, 297). HPLC method A: elution at 1.99 min. ¹H NMR (400 MHz, DMSO-d₆) δ 1.8–1.9 (m, 1H), 2.1–2.2 (m, 1H), 2.65 (m, 2H), 2.7–2.9 (m, 3H), 8.90 (s, 1H), 12.6 (brs), 14.5 (brs).

Step 2: 1(3)-Triphenylmethyl-4,5,6,7-tetrahydro-1H-benzimidazole-5-carboxylic Acid Methyl ester

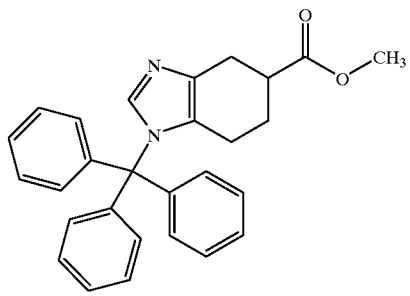

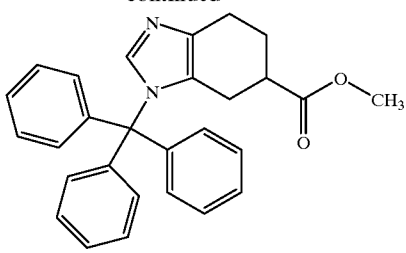

A solution of 4,5,6,7-tetrahydro-1H-benzimidazole-5-carboxylic acid hydrochloride (5.0 g, 23 mmol) in MeOH (100 ml) was stirred under an atmosphere of nitrogen on an ice-bath. Thionyl chloride (2.5 ml, 35 mmol) was added drop wise over 10 minutes. The mixture was stirred for an additional 30 minutes and then refluxed for 2 hours. The volatiles were evaporated to give a residue, which was re-evaporated with acetonitrile (2×) and then stirred with acetonitrile (150 ml). Triethylamine (9.5 ml, 69 mmol) was added to the mixture followed by portion wise addition of triphenylmethyl chloride (6.4 g, 23 mmol). The mixture was stirred overnight at room temperature and then filtered. The solvent was evaporated from the filtrate to give a residue, which was stirred with diethyl ether (200 ml). The mixture was filtered and the solvent was evaporated from the filtrate. This afforded a foamy residue which was dissolved in ethyl actetate (10 ml) and heptane (10 ml) and purified by chromatography on silica gel (150 g, heptane/ethyl acetate 1:1) to give 6.4 g (66%) of 1(3)-triphenylmethyl-4,5,6,7-tetrahydro-1H-benzimidazole-5-carboxylic acid methyl ester.

Mp. 155–156° C. LC-MS: Calc for MH⁺: 423.5; found: 423.4. ¹H NMR (CDCl₃, 400 MHz, two regioisomers, 1:2): δ 1.25–1.40, 1.55–1.70, 1.73–1.85 and 1.97–2.05 (all m, together 4H), 2.45–2.75 and 2.82–2.95 (both m, together 3H), 3.56 and 3.67 (both s, together 3H), 7.10–7.15 (m, 6H), 7.26 and 7.28 (both s, together 1H), 7.30–7.35 (m, 9H).

Step 3:1 (3)-Triphenylmethyl-4,5,6,7-tetrahydro-1H-benzimidazole-5-methanol

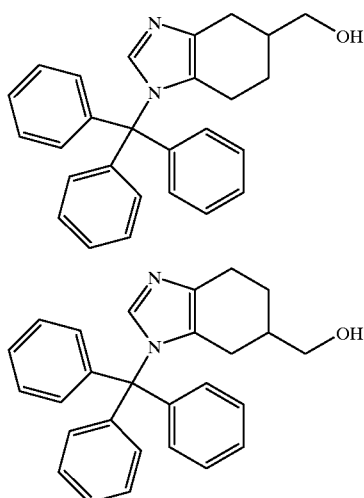

A solution of 1(3)-triphenylmethyl-4,5,6,7-tetrahydro-1H-benzimidazole-5-carboxylic acid methyl ester (5.5 g, 13 mmol) in THF (100 ml) was stirred under an atmosphere of nitrogen. A 1 M solution of lithium aluminiumhydride in THF (8 ml, 8.0 mmol) was added drop wise. The reaction mixture was stirred for 1 hour and then heated at reflux for 30 minutes. To the cooled reaction mixture, H$_2$O (0.5 ml) and 4 N sodium hydroxide (1.0 ml) were added. THF (50 ml) and magnesium sulfate (10 g) were added and the mixture was stirred for 15 minutes. The mixture was filtered and the solvent was evaporated from the filtrate to give a residue which was dried. This afforded 5.35 g of 1(3)-triphenylmethyl-4,5,6,7-tetrahydro-1H-benzimidazole-5-methanol in a quantitative yield.

Mp. 235–238° C. HPLC method A: elution at 7.88 and 8.39 min. LC-MS: Calc for MH$^+$: 395.5; found: 395.4. $^1$H NMR (CDCl$_3$, 400 MHz, two regioisomers, 1:2) δ 1.15–1.45 (m, 2H), 1.65–1.85 (m, 4H), 2.3–2.4 and 2.6–2.8 (both m, together 2H), 3.2–3.35 and 3.45–3.6 (both m, together 2H), 7.10–7.15 (m, 6H), 7.26 (s, 1H), 7.30–7.35 (m, 9H).

Step 4

To a mixture of 1(3)-triphenylmethyl-4,5,6,7-tetrahydro-1H-benzimidazole-5-methanol (160 mg, 0.4 mmol) in THF (3 ml) were added 2-cyanophenol (119 mg, 1.0 mmol) and triphenylphosphine (262 mg, 1.0 mmol) followed by drop wise addition of DEAD (174 mg, 1.0 mmol). The reaction mixture was shaken at room temperature for 24 hours and the volatiles were evaporated. To the residue was added 90% acetic acid (2.5 ml) and the mixture was shaken at 70° C. overnight. The reaction mixture was poured into H$_2$O (40 ml) and 1 N hydrochloric acid (1 ml) was added. The acidic mixture was washed with ethyl acetate (4×10 ml) and then adjusted to pH 11 with 12 N sodium hydroxide (2–3 ml). The alkaline mixture was extracted with ethyl acetate (10 ml). The separated organic phase was treated with a solution of oxalic acid (40 mg, 0.44 mmol) in ethyl acetate (1 ml). On standing a solid was formed which was separated and dried. This afforded 100 mg (73%) of the title compound.

Mp. 240° C. dec. $^1$H NMR (DMSO-d$_6$, 400 MHz): δ 1.6–1.7 (m,1H), 2.05–2.15 (m, 1H), 2.3–2.4 (m, 1H), 2.45–2.55 (m, 1H), 2.6–2.75 (m, 2H), 2.85 (dd, 1H), 4.18 (d, 2H), 7.10 (t, 1H), 7.30 (d, 1H), 7.67 (t, 1H), 7.75 (d, 1H), 8.64 (s, 1H).

Example 2
5-(4-Chlorophenoxymethyl)-4,5,6,7-tetrahydro-1H-benzimidazole, Oxalic Acid salt

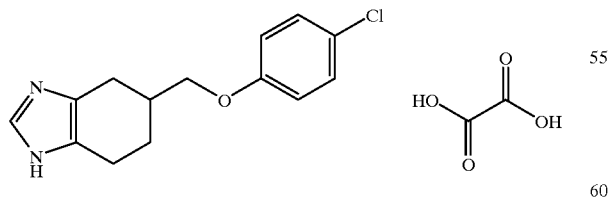

By a similar procedure as described in Example 1 the title compound was prepared. Mp. 240° C. dec. $^1$H NMR (DMSO-d$_6$, 400 MHz): δ 1.55–1.65 (m, 1H), 2.05–2.1 (m, 1H), 2.25–2.35 (m,1H), 2.4–2.5 (m, 1 H), 2.55–2.75 (m, 2H), 2.81 (dd, 1H), 4.00 (d, 2H), 7.00 (d, 2H), 7.33 (d, 2H), 8.69 (s,1H).

Example 3
Cyclopropyl-(4-(4,5,6,7-tetrahydro-1H-benzimidazol-5-ylmethoxy)methanone, Oxalic Acid Salt

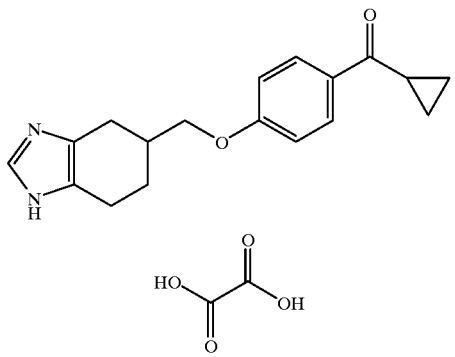

By a similar procedure as described in Example 1 the title compound was prepared. Mp. 236–238° C. $^1$H NMR (DMSO-d$_6$, 400 MHz): δ 0.98 (d, 4H), 1.55–1.65 (m, 1H), 2.05–2.15 (m,1H), 2.25–2.35 (m, 1H), 2.4–2.5 (m, 1H), 2.55–2.7 (m, 2H), 2.80 (dd, 1H), 2.86 (p,1H), 4.11 (d, 2H), 7.10 (d, 2H), 8.04 (d, 2H), 8.38 (s, 1H).

Example 4
5-(Naphth-1-yloxymethyl)-4,5,6,7-tetrahydro-1H-benzimidazole, Oxalic Acid Salt

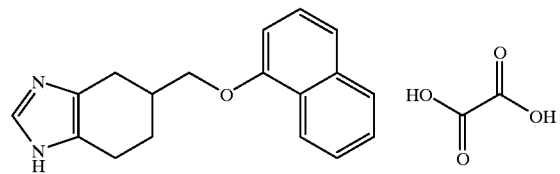

By a similar procedure as described in Example 1 the title compound was prepared. Mp. 236° C. dec. $^1$H NMR (DMSO-d$_6$, 400 MHz): δ 1.7–1.8 (m, 1H), 2.1–2.2 (m, 1H), 2.4–2.5 (m, 1H), 2.55–2.8 (m, 3H), 2.95 (dd, 1H), 4.20 (AB, 2H), 7.00 (d, 1H), 7.4–7.6 (m, 4H), 7.88 (d, 1H), 8.20 (d, 1H), 8.70 (s, 1H).

Example 5
5-(Naphth-2-yloxymethyl)-4,5,6,7-tetrahydro-1H-benzimidazole, Oxalic Acid Salt

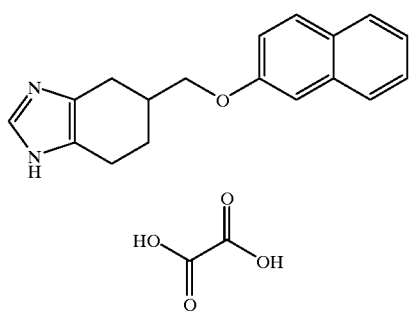

By a similar procedure as described in Example 1 the title compound was prepared. Mp. 162–164° C. $^1$H NMR (DMSO-d$_6$, 400 MHz): δ 1.6–1.75 (m, 1H), 2.1–2.2 (m, 1H), 2.35–2.45 (m, 1H), 2.45–2.55 (m, 1H), 2.6–2.7 (m, 2H), 2.88 (dd, 1H), 4.12 (d, 2H), 7.20 (dd, 1H), 7.35 (t, 1H), 7.37 (s,1H), 7.46 (t,1H), 7.75–7.85 (m, 3H), 8.67 (s,1H).

Example 6

5-(5,6,7,8-Tetrahydronaphth-2-yloxymethyl)-4,5,6,7-tetrahydro-1H-benzimidazole, Oxalic Acid Salt

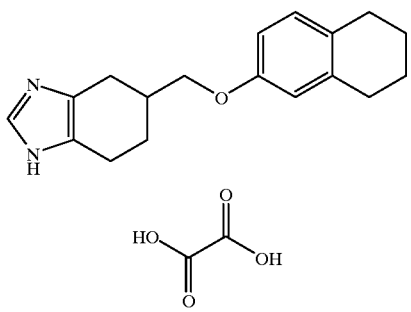

By a similar procedure as described in Example 1 the title compound was prepared. Mp. 165–167° C. $^1$H NMR (DMSO-d$_6$, 400 MHz): δ 1.55–1.65 (m, 1H), 1.7 (m, 4H), 2.0–2.1 (m, 1H), 2.2–2.3 (m, 1H), 2.4–2.5 (m, 1H), 2.55–2.75 (m, 6H), 2.80 (dd, 1H), 3.94 (d, 2H), 6.64 (d, 1H), 6.68 (dd, 1H), 6.94 (d, 1H), 8.65 (s, 1H).

Example 7

5-(3-Chlorophenoxymethyl)-4,5,6,7-tetrahydro-1H-benzimidazole, Oxalic Acid Salt

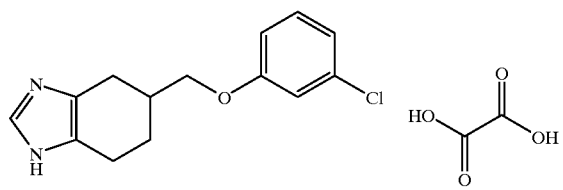

By a similar procedure as described in Example 1 the title compound was prepared. Mp. 225° C. $^1$H NMR (DMSO-d$_6$, 400 MHz): δ 1.55–1.65 (m, 1H), 2.0–2.1 (m, 1H), 2.2–2.35 (m,1H), 2.4–2.5 (m,1H), 2.55–2.7 (m, 2H), 2.79 (dd,1H), 4.02 (d, 2H), 6.96 (dd,1H), 7.00 (d, 1H), 7.06 (d, 1H), 7.31 (t, 1H), 8.47 (s, 1H).

Example 8

3-(4,5,6,7-Tetrahydro-1H-benzimidazol-5-ylmethoxy) benzonitrile, Oxalic Acid Salt

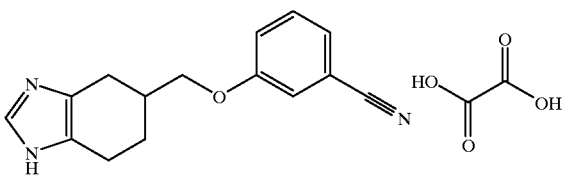

By a similar procedure as described in Example 1 the title compound was prepared. Mp. 221° C. dec. $^1$H NMR (DMSO-d$_6$, 400 MHz): δ 1.55–1.65 (m, 1H), 2.0–2.1 (m, 1H), 2.25–2.35 (m, 1H), 2.4–2.5 (m, 1H), 2.55–2.75 (m, 2H), 2.79 (dd, 1H), 4.07 (d, 2H), 7.33 (dd, 1H), 7.41 (d,1H), 7.45–7.55 (m, 2H), 8.40 (s, 1H).

Example 9

5-(4-Benzylphenoxymethyl)-4,5,6,7-tetrahydro-1H-benzimidazole, Oxalic Acid Salt

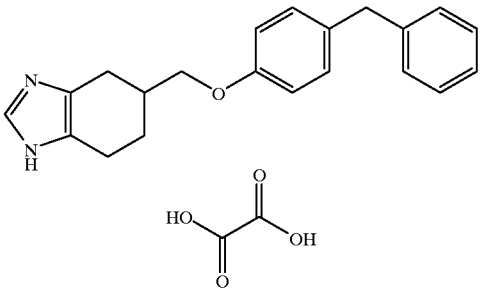

By a similar procedure as described in Example 1 the title compound was prepared. Mp. 230–233° C. $^1$H NMR (DMSO-d$_6$, 400 MHz): δ 1.5–1.6 (m, 1H), 2.0–2.1 (m, 1H), 2.15–2.25 (m, 1H), 2.3–2.4 (m,1H), 2.5–2.65 (m, 2H), 2.73 (dd, 1H), 3.86 (s, 2H), 3.92 (d, 2H), 6.88 (d, 1H), 7.1–7.3 (m, 7H), 8.10 (s, 1H).

Example 10

5-(3,4-Methylenedioxyphenoxymethyl)-4,5,6,7-tetrahydro-1H-benzimidazole, Oxalic Acid Salt

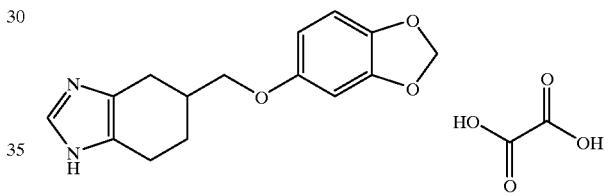

By a similar procedure as described in Example 1 the title compound was prepared. Mp. 228° C. $^1$H NMR (DMSO-d$_6$, 400 MHz): δ 1.5–1.6 (m, 1H), 2.0–2.1 (m, 1H), 2.15–2.3 (m, 1H), 2.35–2.45 (m, 1H), 2.55–2.7 (m, 2H), 2.77 (dd, 1H), 3.90 (d, 2H), 5.96 (s, 2H), 6.49 (dd, 1H), 6.65 (d, 1H), 6.80 (d,1H), 8.40 (s, 1H).

Example 11

4-(4,5,6,7-Tetrahydro-1H-benzimidazol-5-ylmethoxy) benzoic Acid Ethyl Ester, Oxalic Acid Salt

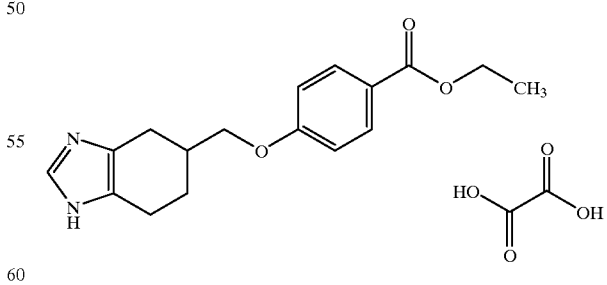

By a similar procedure as described in Example 1 the title compound was prepared. Mp. 243° C. dec. $^1$H NMR (DMSO-d$_6$, 400 MHz): δ 1.31 (t, 3H), 1.55–1.7 (m, 1H), 2.05–2.15 (m,1H), 2.25–2.4 (m,1H), 2.4–2.5 (m, 1H), 2.55–2.75 (m, 2H), 2.85 (dd, 1H), 4.11 (d, 2H), 4.28 (q, 2H), 7.09 (d, 2H), 7.93 (d, 2H), 8.38 (s, 1H).

Example 12
5-(2,4-Difluorophenoxymethyl)-4,5,6,7-tetrahydro-1H-benzimidazole, Hydrochloride Salt

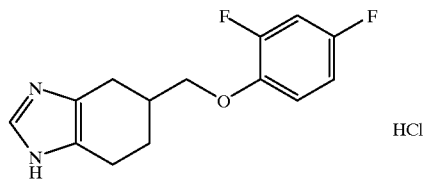

A mixture of 1(3)-triphenylmethyl-4,5,6,7-tetrahydro-1H-benzimidazole-5-methanol (1.0 g, 2.5 mmol), 2,4-difluorophenol (390 mg, 3.0 mmol) and triphenylphosphine (786 mg, 3.0 mmol) in dry THF (20 ml) was placed under nitrogen. The mixture was stirred on an ice-bath and DEAD (470 μl, 3.0 mmol) was added drop wise. The reaction mixture was stirred overnight at ambient temperature and then the volatiles were evaporated. To the residue was added 90% acetic acid (20 ml) and the mixture was heated at reflux temperature for 1–2 hours. The reaction mixture was poured into $H_2O$ (200 ml) and 1 N hydrochloric acid (100 ml) was added. The acidic mixture was washed with diethyl ether (3×100 ml) and then adjusted to pH 11 with 12 N sodium hydroxide. The alkaline mixture was extracted with ethyl acetate (2×150 ml). The combined organic extracts were dried (magnesium sulphate), filtered and the solvent was evaporated. The residue was dissolved in 1 N hydrochloric acid (10 ml) and the volatiles were evaporated to give a residue that was triturated twice with acetone. This afforded 700 mg (93%) of the title compound as a solid.
Mp. 225–227° C. HPLC method A: elution at 10.05 min.

Example 13
5-(2-Chlorophenoxymethyl)-4,5,6,7-tetrahydro-1H-benzimidazole, Hydrochloride Salt

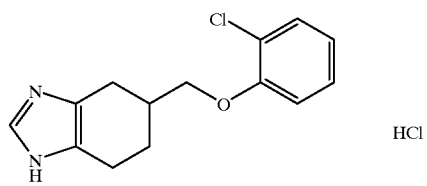

By a similar procedure as described in Example 12 the title compound was prepared.
Mp. 224–226° C.
Microanalysis for $C_{14}H_{15}ClN_2O$, HCl:
Calc: C: 56.20%; H: 5.39%; N: 9.36%.
Found: C: 56.37%; H: 5.49%; N: 9.32%.

Example 14
5-(2-Iodophenoxymethyl)-4,5,6,7-tetrahydro-1H-benzimidazole, Oxalic Acid Salt

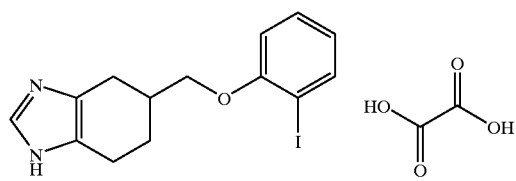

By a similar procedure as described in Example 1 the title compound was prepared HPLC method B: elution at 9.17 min. LC-MS: Calc for $MH^+$: 355.2; found: 354.8.

Example 15
5-(2-Trifluoromethylphenoxymethyl)-4,5,6,7-tetrahydro-1H-benzimidazole, Hydrochloride Salt

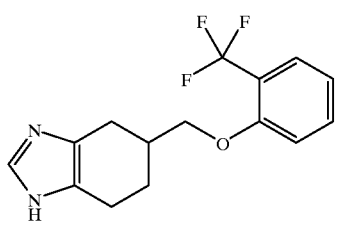

By a similar procedure as described in Example 12 the title compound was prepared.
Mp. 208–211° C.
Microanalysis for $C_{16}H_{15}F_3N_2O$, HCl:
Calc: C: 54.14%; H: 4.85%; N: 8.42%.
Found: C: 53.86%; H: 5.05%; N: 8,66%.

Example 16
5-(2-Fluorophenoxymethyl)-4,5,6,7-tetrahydro-1H-benzimidazole, Hydrochloride Salt

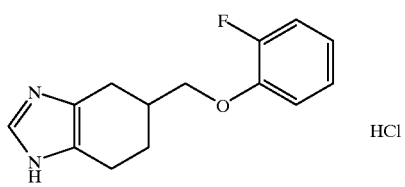

By a similar procedure as described in Example 12 the title compound was prepared.
Mp. 192–194° C.
Microanalysis for $C_{14}H_{15}FN_2O$,HCl:
Calc: C: 59.47%; H: 5.70%; N: 9.91%.
Found: C: 59.49%; H: 5.92%; N: 9.91%.

Example 17
5-(3-Trifluoromethoxyphenoxymethyl)-4,5,6,7-tetrahydro-1H-benzimidazole, Hydrochloride Salt

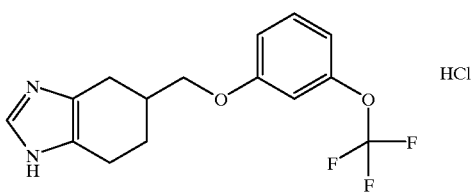

By a similar procedure as described in Example 12 the title compound was prepared.
Mp. 170–171° C.
Microanalysis for $C_{15}H_{15}F_3N_2O_2$,HCl):
Calc: C: 51.66%; H: 4.62%; N: 8.03%.
Found: C: 51.67%; H: 4.75%; N: 8.04%.

Example 18

5-(Biphenyl-3-yloxymethyl)-4,5,6,7-tetrahydro-1H-benzimidazole, Hydrochloride Salt

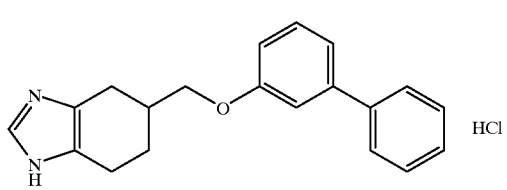

By a similar procedure as described in Example 12 the title compound was prepared.

Mp. 165–167° C.

Microanalysis for $C_{20}H_{20}N_2O,HCl,½H_2O$:

Calc: C: 68.66%; H: 6.34%; N: 8.01%.

Found: C: 68.60%; H: 6.38%; N: 8.17%.

Example 19

5-(3-Trifluoromethylphenoxymethyl)-4,5,6,7-tetrahydro-1H-benzimidazole, Hydrochloride Salt

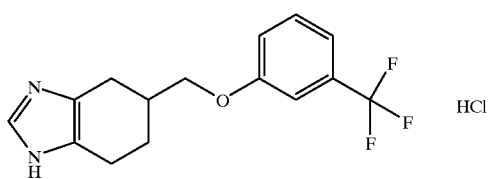

By a similar procedure as described in Example 12 the title compound was prepared.

Mp. 218–220° C.

Microanalysis for $C_{16}H_{15}F_3N_2O,HCl$:

Calc: C: 54.14%; H: 4.85%; N: 8.42%.

Found: C: 54.09%; H: 5.03%; N: 8.42%.

Example 20

5-(2,6-Difluorophenoxymethyl)-4,5,6,7-tetrahydro-1H-benzimidazole, Hydrochloride Salt

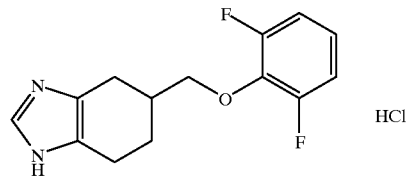

By a similar procedure as described in Example 12 the title compound was prepared.

Mp. 225–227° C. HPLC method A: elution at 9.79 min.

Example 21

5-(4-Trifluoromethoxyphenoxymethyl)-4,5,6,7-tetrahydro-1H-benzimidazole, Hydrochloride Salt

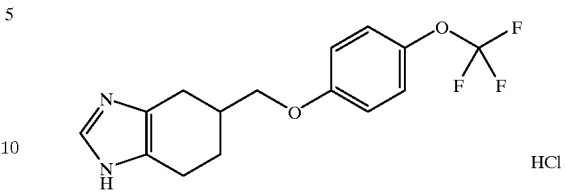

By a similar procedure as described in Example 12 the title compound was prepared.

Mp. 251–253° C. HPLC method A: elution at 12.28 min.

Example 22

4-(2-Ethylphenoxymethyl)$_{4,5,6,7}$-tetrahydro-1H-benzimidazole, Oxalic Acid Salt

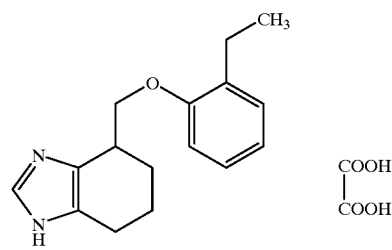

Step 1: 1-Triphenylmethyl-4,5,6,7-tetrahydro-1H-benzimidazole-4-carboxylic Acid Ethyl Ester

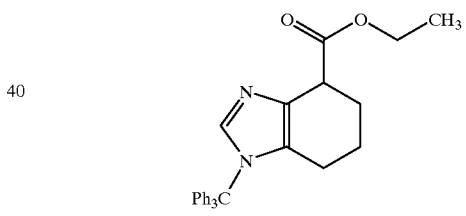

To a solution of 4,5,6,7-tetrahydro-1H-benzimidazole-4-carboxylic acid ethyl ester (18.9 g, 97 mmol, J. Am. Chem. Soc., 1996, 98, 984) in acetonitrile (250 ml) were added triethylamine (27 ml, 194 mmol) and a solution of triphenylmethyl chloride (40.6 g, 146 mmol) in acetonitrile (500 ml). The resulting mixture was stirred at 20° C. overnight. The mixture was concentrated under reduced pressure and the residue was re-dissolved in ethyl acetate, washed with water (2×) and brine (1×), and concentrated under reduced pressure. The residue was recrystallised from ethyl acetate/heptane, to yield 20.8 g (49%) of 1-triphenylmethyl-4,5,6,7-tetrahydro-1H-benzimidazole-4-carboxylic acid ethyl ester as colourless solid. From the mother liquor more product (10.3 g, 24%) was isolated by column chromatography (silica gel, gradient elution with heptane/ethyl acetate 9:1 to 1:1).

$^1$H NMR (300 MHz, CDCl$_3$) δ 1.29 (t, J=7 Hz, 3H), 1.30–1.50 (m, 2H), 1.58–1.73 (m, 2H), 1.75–2.02 (m, 2H), 3.73 (t, J=6 Hz,1H), 4.19 (m, 2H), 7.13 (m, 6H), 7.25–7.36 (m, 10H).

Step 2: 4-Hydroxymethyl-1-triphenylmethyl-4,5,6,7-tetrahydro-1H-benzimidazole

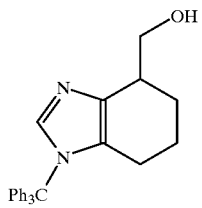

To a solution of 1-triphenylmethyl-4,5,6,7-tetrahydro-1H-benzimidazol-4-carboxylic acid ethyl ester (14.0 g, 32 mmol) in THF (100 ml) was added lithium aluminum hydride (24 ml, 1 mol/L in THF, 24 mmol). The mixture was stirred at 20° C. for 45 min, and water (3.5 ml) and sodium hydroxide (3.5 ml, 4 mol/L in water) were carefully added. $H_2O$ (14 ml) and concentrated aqueous hydrochloric acid (1.13 ml) were added, and the mixture was filtered and concentrated under reduced pressure. The residue was re-dissolved in ethyl acetate (150 ml), dried (magnesium sulfate), filtered, and kept at 20° C. overnight. Filtration yielded 7.0 g (55%) of 4-hydroxymethyl-1-triphenylmethyl-4,5,6,7-tetrahydro-1H-benzimidazole as a colourless solid.

Mp. 168–170° C. $^1$H NMR (400 MHz, CDCl$_3$) δ 1.08–1.19 (m, 1H), 1.28–1.50 (m, 2H), 1.54–1.66 (m, 2H), 1.72–1.80 (m, 1H), 2.91–3.00 (m, 1H), 3.59 (t, J=10 Hz, 1H), 3.72–3.81 (m, 1H), 4.62 (d, br, J=10 Hz, 1H), 7.13 (m, 6H), 7.27 (s, 1H), 7.33 (m, 9H).

Step 3

To a solution of 4-hydroxymethyl-1-triphenylmethyl-4,5,6,7-tetrahydro-1H-benzimidazole (0.21 g, 0.54 mmol) in THF (3 ml) were added triphenylphosphine (0.20 g, 0.75 mmol), 2-ethylphenol (0.073 ml, 0.60 mmol), and DEAD (0.118 ml, 0.75 mmol). The mixture was shaken at 20° C. overnight, concentrated under reduced pressure, and the residue was purified by column chromatography (silica gel, gradient elution with heptane/ethyl acetate 9:1 to 1:1). The resulting product (100 mg) was dissolved in 5 ml of a mixture of glacial acetic acid and $H_2O$ (9:1), and kept at 70° C. for 20 hours. The mixture was concentrated and the residue was re-dissolved in ethyl acetate. To this solution was added a solution of oxalic acid (45 mg) in ethyl acetate (5 ml), whereby 23 mg (12%) of the title compound precipitated as a colourless solid.

Mp. 133–134° C. $^1$H NMR (400 MHz, DMSO-d$_6$) δ 1.02 (t, J=7 Hz, 3H), 1.70–2.08 (m, 4H), 2.44–2.62 (m, 4H), 3.25 (m, 1H), 4.07 (t, J=10 Hz, 1H), 4.28 (dd, J=10 Hz, 4 Hz, 1H), 6.88 (t, J=7 Hz, 1H), 6.96 (d, J=9 Hz, 1H), 7.11–7.18 (m, 2H), 8.48 (s, 1H).

Example 23

4-(4-Cyanophenoxymethyl)-4,5,6,7-tetrahydro-1H-benzimidazole, Oxalic Acid Salt

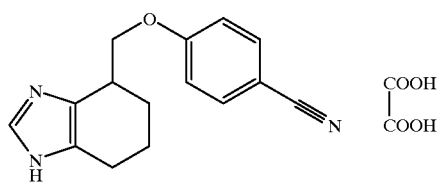

Using the procedure described in Example 22 and starting from 4-hydroxymethyl-1-triphenylmethyl-4,5,6,7-tetrahydro-1H-benzimidazole (0.21 g, 0.54 mmol) and 4-cyanophenol (0.071 g, 0.6 mmol) 34 mg (18%) of the title compound were obtained.

$^1$H NMR (300 MHz, DMSO-d$_6$) δ 1.60–2.00 (m, 4H), 2.55–2.62 (m, 2H), 3.18–3.27 (m, 1H), 4.18 (t, J=8 Hz, 1H), 4.29 (dd, J=8 Hz, 6 Hz, 1 H), 7.17 (d, J=8 Hz, 2H), 7.77 (d, J=8 Hz, 2H), 8.33 (s, 1H).

Example 24

4-(Naphth-1-yloxymethyl)-4,5,6,7-tetrahydro-1H-benzimidazole, Oxalic Acid Salt

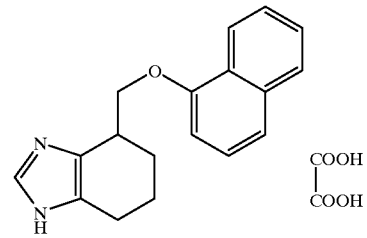

Using the procedure described in Example 22 and starting from 4-hydroxymethyl-1-triphenylmethyl-4,5,6,7-tetrahydro-1H-benzimidazole (0.21 g, 0.54 mmol) and 2-phenylphenol (0.087 g, 0.6 mmol) 39 mg (20%) of the title compound was obtained.

Mp. 213–216° C. $^1$H NMR (400 MHz, DMSO-d$_6$) δ 1.75–1.83 (m, 1H), 1.85–2.04 (m, 4H), 2.06–2.13 (m, 1H), 2.61 (m, 2H), 3.33 (m, 1H), 4.19 (t, J=9 Hz, 1H), 4.47 (dd, J=9 Hz, 6 Hz, 1H), 7.01 (d, J=8 Hz, 1H), 7.39–7.56 (m, 4H), 7.87 (d, J=8 Hz, 1H), 8.12 (m, 2H).

Example 25

4-(2-Chlorophenoxymethyl)-4,5,6,7-tetrahydro-1H-benzimidazole, Hydrochloride Salt

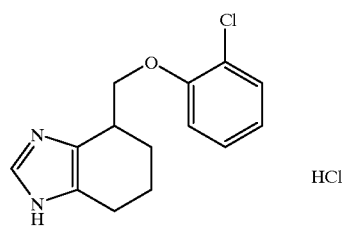

Using a procedure similar to that described in Example 22 and starting from 4-hydroxymethyl-1-triphenylmethyl-4,5,6,7-tetrahydro-1H-benzimidazole (0.19 g, 0.48 mmol) and 2-chlorophenol (0.1 ml, 1 mmol) 20 mg (14%) of the title compound was obtained as a solid.

Mp. 207–209° C. $^1$H NMR (400 MHz, DMSO-d$_6$) δ 1.74–2.05 (m, 4H), 2.62 (m, 2H), 4.23 (dd, J=10 Hz, 8 Hz, 1H), 4.36 (dd, J=10 Hz, 3 Hz, 1H), 6.99 (t, J=8 Hz, 1H), 7.21 (d, J=9 Hz, 1H), 7.31 (t, J=8 Hz, 1H), 7.42 (d, J=9 Hz, 1H), 8.95 (s, 1H), 14.23 (s, br, 2H).

Microanalysis for $C_{14}H_{15}ClN_2O$, HCl (299.20):

Calc: C: 56.20%, H: 5.39%, N: 9.36%;

Found: C: 56.49%, H: 5.46%, N: 9.31%.

Example 26
4-(2-Chlorophenoxymethyl)-1,4,5,6,7,8-hexahydrocycloheptaimidazole, Hydrochloride Salt

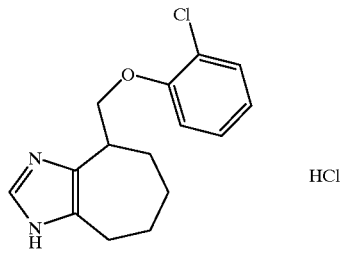

Step 1: 1-Triphenylmethyl-1,4,5,6,7,8-hexahydrocycloheptaimidazole-4-Carboxylic Acid Methyl Ester

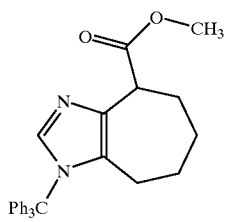

To a solution of crude 1,4,5,6,7,8-hexahydrocycloheptaimidazole-4-carboxylic acid methyl ester (8.75 g, approx. 45.0 mmol, J. Am. Chem. Soc. 1976, 98, 984) in dichloromethane (100 ml) were added triethylamine (15.4 ml, 111 mmol) and a solution of triphenylmethyl chloride (18.5 g, 66.4 mmol) in dichloromethane (100 ml). The resulting mixture was stirred at 20° C. overnight. The mixture was washed with water and dried with magnesium sulfate. Filtration, concentration, and column chromatography (silica gel, gradient elution with heptane/ethyl acetate 9:1 to 1:1) yielded 5.5 g (28%) of the title compound as a solid.

Mp. 161–163° C. $^1$H NMR (400 MHz, CDCl$_3$): δ 0.89 (m, 1H), 1.18 (m, 1H), 1.55–1.65 (m, 2H), 1.74–1.83 (m, 1H), 1.89–2.01 (m, 2H), 2.09–2.19 (m, 1H), 3.74 (s, 3H), 3.93 (m, 1H), 7.04 (s, 1H), 7.15 (m, 6H), 7.32 (m, 9H).

Step 2: (1-Triphenylmethyl-1,4,5,6,7,8-hexahydrocycloheptaimidazole-4-yl)methanol

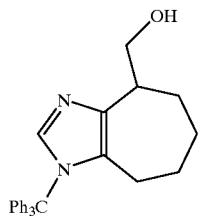

To a solution of 1-triphenylmethyl-1,4,5,6,7,8-hexahydrocycloheptaimidazole-4-carboxylic acid methyl ester (5.5 g, 12.6 mmol) in THF (140 ml) was added lithium aluminum hydride (9.5 ml, 1 mol/L in THF, 9.5 mmol). The mixture was stirred at 20° C. for 2 hours, and water (1.4 ml) and NaOH (1.4 ml, 4 mol/l in water) were carefully added. After stirring at room temperature for 0.5 hours, water (5 ml) was added, and after stirring for 0.5 hours the mixture was dried by addition of magnesium sulfate. Filtration, concentration, and precipitation from methanol yielded 4.4 g (86%) of the title alcohol as a solid.

Mp. 169–171° C. $^1$H NMR (400 MHz, CDCl$_3$): δ 0.75–0.85 (m, 1H), 1.22–1.32 (m, 2H), 1.38–1.50 (m, 1H), 1.55–1.65 (m, 1H), 1.75–1.94 (m, 2H), 1.98–2.05 (m, 1H), 2.81–2.90 (m, 1H), 3.82 (m, 1H), 3.96 (t, J=10 Hz, 1H), 5.11 (s, br, 1H), 7.06 (s, 1H), 7.13 (m, 6H), 7.32 (m, 9H).

Step 3

Using a procedure similar to that described in Example 22 and starting from (1-triphenylmethyl-1,4,5,6,7,8-hexahydrocycloheptaimidazole-4-yl)methanol (0.20 g, 0.49 mmol) and 2-chlorophenol (0.1 ml, 1 mmol) 94 mg (61%) of the title compound was obtained as a solid.

Mp. 167–171° C. $^1$H NMR (400 MHz, DMSO-d$_6$) δ 1.45–1.95 (m, 5H), 2.10 (m, 1H), 2.80 (s, br, 2H), 3.48 (s, br, 1H), 4.22 (m, 2H), 6.98 (t, J=8 Hz, 1H), 7.20 (d, J=8 Hz, 1H), 7.30 (m, 1H), 7.91 (d, br, J=8 Hz, 1H), 8.88 (s, 1H), 14.23 (s, br, 2H).

Example 27
4-(2,4-Difluorophenoxymethyl)-4,5,6,7-tetrahydro-1H-benzimidazole, Hydrochloride Salt

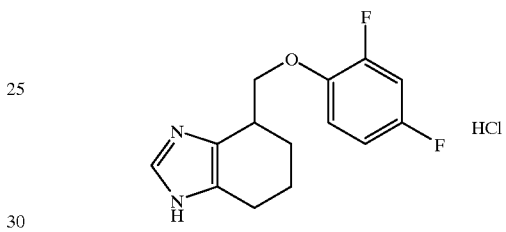

Using a procedure similar to that described in Example 22 and starting from 4-hydroxymethyl-1-triphenylmethyl-4,5,6,7-tetrahydro-1H-benzimidazole (0.31 g, 0.78 mmol) and 2,4-difluorophenol (0.15 ml, 1.57 mmol) was obtained 134 mg (57%) of the title compound as a solid.

Mp. 222–223° C. $^1$H NMR (400 MHz, DMSO-d$_6$) δ 1.72–2.03 (m, 4H), 2.62 (s, br, 2H), 3.29 (s, br, 1H), 4.22 (t, J=8 Hz, 1H), 4.31 (dd, J=8 Hz, 5 Hz, 1H), 7.03 (m, 1H), 7.23–7.33 (m, 2H), 8.95 (s, 1H), 14.30 (s, br, 2H).

Example 28
4-(2,4-Difluorophenoxymethyl)-1,4,5,6,7,8-hexahydrocycloheptaimidazole, Hydrochloride Salt

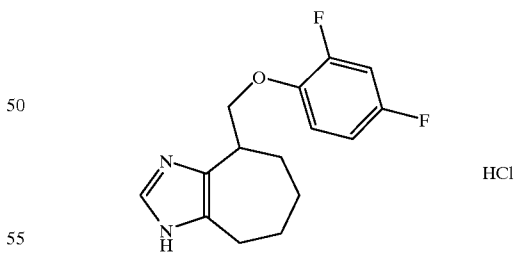

Using a procedure similar to that described in Example 22 and starting from (1-triphenylmethyl-1,4,5,6,7,8-hexahydrocycloheptaimidazole-4-yl)methanol (0.32 g, 0.78 mmol) and 2,4-difluorophenol (0.15 ml, 1.57 mmol) 125 mg (51%) of the title compound was obtained as a hygroscopic foam.

$^1$H NMR (400 MHz, DMSO-d$_6$) δ 1.45–1.95 (m, 5H), 2.05 (m, 1H), 2.78 (s, br, 2H), 3.41 (s, br, 1H), 4.22 (m, 2H), 7.02 (m, 1H), 7.20–7.34 (m, 2H), 8.83 (s, 1H), 14.12 (s, br, 2H).

Example 29
4-(3-Acetylphenoxymethyl)-1,4,5,6,7,8-hexahydrocycloheptaimidazole, Hydrochloride Salt

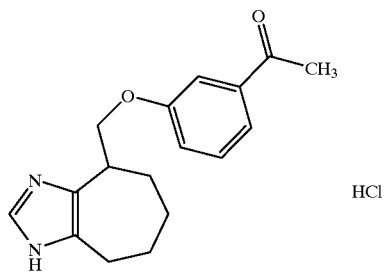

Using a procedure similar to that described in Example 22 and starting from (1-triphenylmethyl-1,4,5,6,7,8-hexahydrocycloheptaimidazole-4-yl)methanol (0.32 g, 0.78 mmol) and 3-acetylphenol (0.21, 1.56 mmol) was obtained 120 mg (48%) of the title compound as a hygroscopic foam.

$^1$H NMR (400 MHz, DMSO-$d_6$) δ 1.45–1.95 (m, 5H), 2.04–2.12 (m, 4H), 2.81 (s, br, 2H), 3.41 (s, br, 1H), 4.22 (m, 2H), 7.25 (m, 1H), 7.43 (m, 2H), 7.57 (d, J=8 Hz,1H), 8.88 (s,1H), 14.25 (s, br, 2H).

Example 30
5-[2-(2,4-Dichlorophenoxy)ethyl]-4,5,6,7-tetrahydro-1H-benzimidazole Hydrochloride

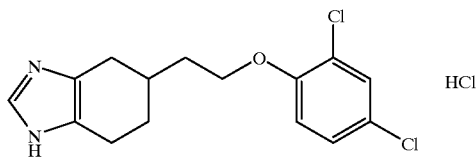

Step 1: (4,5,6,7-Tetrahydro-1H-benzimidazol-5-yl)acetonitrile Hydrochloride

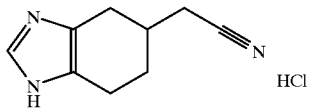

A mixture of 1(3)-triphenylmethyl-4,5,6,7-tetrahydro-1H-benzimidazole-5-methanol (8.0 g, 20 mmol, prepared as described in Example 1) and dry pyridine (50 ml) was placed under an atmosphere of nitrogen and on an ice-bath. Methanesulfonyl chloride (3.0 ml, 40 mmol) was added dropwise at 0° C. The ice-bath was removed and the mixture was stirred at ambient temperature for 2 hours. The volatiles were evaporated and the residue was stirred with a mixture of toluene (300 ml) and $H_2O$ (150 ml). The phases were separated and the organic phase was washed with $H_2O$ (50 ml) and brine and dried ($Na_2SO_4$). The solvent was evaporated and the residue was dried in vacuo to give 10.2 g of crude methanesulfonic acid (1(3)-triphenylmethyl-4,5,6,7-tetrahydro-1H-benzimidazol-5-yl)methyl ester. This mesylate (10.2 g, 20 mmol) was stirred with a 0.5 M lithium cyanide solution in DMF (60 ml, 30 mmol) under an atmosphere of nitrogen. Potassium iodide (approx. 0.5 g) was added and the mixture was stirred at 80° C. overnight. The volatiles were evaporated and the residue was treated with $H_2O$ (150 ml) and ethyl acetate (300 ml). The phases were separated and the organic phase was washed with water and brine and dried (magnesium sulphate). The solvent was evaporated and the residue was re-evaporated with acetonitrile to give 9.6 g of crude (1(3)-triphenylmethyl-4,5,6,7-tetrahydro-1H-benzimidazol-5-yl)acetonitrile. 90% Acetic acid (150 ml) was added and the mixture was heated at reflux for 1 hour. The volatiles were evaporated and the residue was stirred with a mixture of 0.5 N hydrochloric acid (100 ml) and diethyl ether (100 ml). The phases were separated and the aqueous phase was washed with diethyl ether (2×100 ml). The aqueous phase was evaporated to dryness and the residue was re-evaporated several times with acetone to give 3.5 g (89%) of 4,5,6,7-tetrahydro-1H-benzimidazole-5-acetonitrile hydrochloride.

$^1$H NMR (DMSO-$d_6$, 400 MHz): δ 1.50–1.65 (m, 1H), 1.95–2.05 (m, 1H), 2.15–2.25 (m, 1H), 2.35–2.45 (m,1H), 2.55–2.75 (m, 4H), 2.83 (dd,1H), 8.90 (s,1H), 14.5 (brs, 2H).

Step 2: 4,5,6,7-Tetrahydro-1H-benzimidazole-5-acetic Acid Hydrochloride

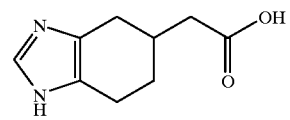

A solution of 4,5,6,7-tetrahydro-1H-benzimidazole-5-acetonitrile hydrochloride (3.0 g, 15 mmol) in 5 N hydrochloric acid (75 ml) was heated at reflux overnight. The volatiles were evaporated and the residue was re-evaporated with acetonitrile (3x). The residue was dissolved in acetone and left for crystallisation. The precipitate was isolated and dried to give 3.25 g (99%) of (4,5,6,7-tetrahydro-1H-benzimidazole-5-acetic acid hydrochloride.

$^1$H NMR (DMSO-$d_6$, 400 MHz): δ 1.45–1.60 (m, 1H), 1.90–1.95 (m, 1H), 2.1–2.2 (m, 1H), 2.25–2.40 (m, 3H), 2.55–2.70 (m, 2H), 2.78 (dd, 1H), 8.90 (s, 1H), 12.3 (brs, 1H), 14.55 (brs, 2H).

Step 3: 2-(1(3)-Triphenylmethyl-4,5,6,7-tetrahydro-1H-benzimidazol-5-yl)ethanol

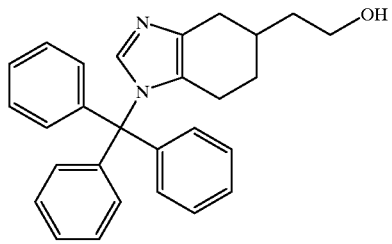

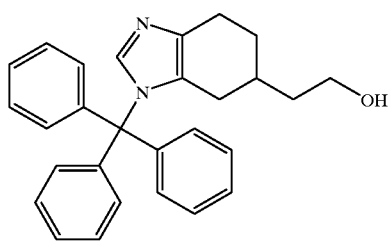

A mixture of 4,5,6,7-tetrahydro-1H-benzimidazole-5-acetic acid (2.2 g, 10 mmol) and ethanol (40 ml) was placed on an ice-bath and thionylchloride (1.78 g, 15 mmol) was added dropwise. When addition was complete, the mixture was stirred for 30 minutes and then heated at reflux for 5 hours. The solvent was evaporated and the residue was re-evaporated with acetonitrile and then stirred with acetonitrile (40 ml) and triethylamine (1.5 ml). The resulting mixture was filtered and the solid was discarded. From the filtrate the solvent was evaporated to give crude 4,5,6,7-tetrahydro-1H-benzimidazole-5-acetic acid ethyl ester. This ester was dissolved in acetonitrile (40 ml) and triethylamine (1.5 ml, 11 mmol) was added followed by portionwise addition of triphenylmethylchloride (2.8 g, 10 mmol). When addition was complete the mixture was stirred overnight at ambient temperature. The mixture was filtered and from the filtrate the solvent was evaporated. The residue was dissolved in ethyl acetate (25 ml) and left for crystallisation. The solid formed was isolated and discarded and from the filtrate the solvent was evaporated. The residue was dissolved in THF (40 ml) and the mixture was placed under an atmosphere of nitrogen. 1 N Lithiumaluminium hydride in THF (6 ml, 6 mmol) was added dropwise. When addition was complete the mixture was stirred at ambient temperature for 3 hours. The mixture was quenched with small amounts of water and 4 N Sodium hydroxide and ethyl acetate was added (50 ml). The solid was removed by filtration and the filtrate was dried (magnesium sulphate). The solvent was evaporated to give a residue that was crystallised from ethyl acetatete (20 ml). This afforded 1.3 g (32%) of 2-(1(3)-triphenylmethyl-4,5,6,7-tetrahydro-1H-benzimidazol-5-yl)ethanol.

HPLC method E: elution at 6.78 and 7.28 min.

Step 4

Using a procedure similar to that described in Example 1 and starting from 2-(1(3)-triphenylmethyl-4,5,6,7-tetrahydro-1H-benzimidazol-5-yl)ethanol (0.40 g, 1.0 mmol) and 2,4-dichlorophenol (0.25 g, 1.5 mmol), was obtained 250 mg (72%) of the title compound.

$^1$H NMR (DMSO-d$_6$, 400 MHz): δ 1.48–1.62 (m, 1H), 1.80–1.90 (m, 2H), 1.95–2.12 (m, 2H), 2.32–2.42 (m, 1H), 2.50–2.70 (m, 2H), 2.80 (dd, 1H), 4.18 (t, 2H), 7.20 (d, 1H), 7.35 (dd, 1H), 7.58 (d, 1H), 8.89 (s, 1H), 14.3 (brs, 2H).

Example 31

5-[2-(3-Phenoxyphenoxy)ethyl]-4,5,6,7-tetrahydro-1H-benzimidazole Hydrochloride

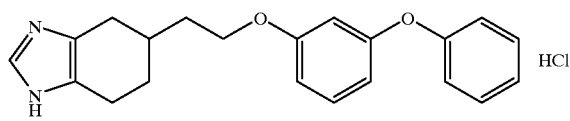

Using a procedure similar to that described in Example 30 and starting from 2-(1(3)-triphenylmethyl-4,5,6,7-tetrahydro-1H-benzimidazol-5-yl)ethanol (0.20 g, 0.50 mmol) and 3-phenoxyphenol (0.14 g, 0.75 mmol), 140 mg (75%) of the title compound was obtained.

HPLC method D: elution at 17.56 min.

Example 32

5-[2-(Naphth-1-yloxy)ethyl]-4,5,6,7-tetrahydro-1H-benzimidazole Hydrochloride

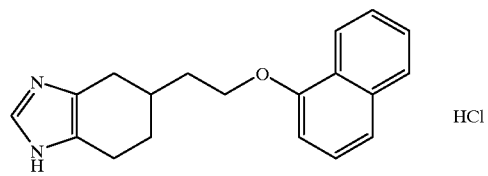

Using a procedure similar to that described in Example 30 and starting from 2-(1(3)-triphenylmethyl-4,5,6,7-tetrahydro-1H-benzimidazol-5-yl)ethanol (0.20 9, 0.50 mmol) and 1-naphthol (0.108 g, 0.75 mmol), 75 mg (46%) of the title compound was obtained.

$^1$H NMR (DMSO-d$_6$, 400 MHz): δ 1.50–1.65 (m, 1 H), 1.85–2.25 (m, 4H), 2.38–2.42 (m, 1H), 2.55–2.75 (m, 2H), 2.80–2.90 (m, 1H), 4.30 (s, 2H), 7.02 (d,1H), 7.38–7.60 (m, 4H), 7.85 (d, 1H), 8.15 (d, 1H), 8.88 (s, 1H), 14.3 (brs, 2H).

Example 33

5-[2-(Biphenyl-2-yloxy)ethyl]-4,5,6,7-tetrahydro-1H-benzimidazole Hydrochloride

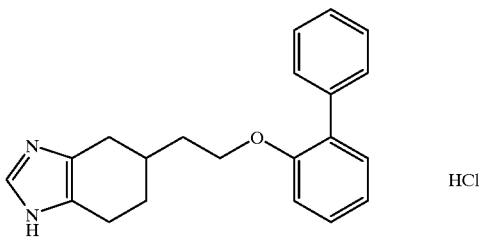

Using a procedure similar to that described in Example 30 and starting from 2-(1(3)-triphenylmethyl-4,5,6,7-tetrahydro-1H-benzimidazol-5-yl)ethanol (0.20 g, 0.50 mmol) and 2-phenylphenol (0.127 g, 0.75 mmol), 100 mg (56%) of the title compound was obtained.

$^1$H NMR (DMSO-d$_6$, 400 MHz) δ 1.35–1.50 (m, 1H), 1.65–1.80 (m, 2H), 1.85–1.95 (m, 2H), 2.20–2.30 (m, 1H), 2.42–2.55 (m, 1H), 2.55–2.70 (m, 2H), 4.02–4.15 (m, 2H), 7.05 (t, 1H), 7.15 (d, 1H), 7.25–7.33 (m, 5H), 7.46 (d, 2H), 8.88 (s, 1H), 14.25 (brs, 2H).

Example 34

5-[3-(4-Chlorophenoxy)propyl]-4,5,6,7-tetrahydro-1H-benzimidazole Hydrochloride

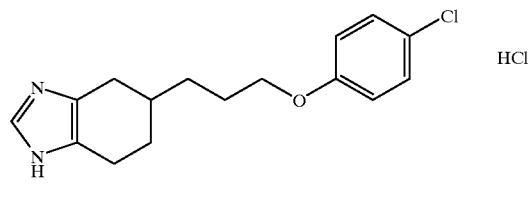

Step 1: 3-(4,5,6,7-Tetrahydro-1H-benzimidazol-5-yl)propionitrile hydrochloride

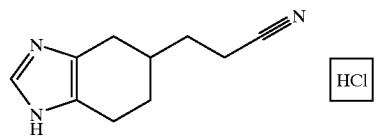

A mixture of 2-(1(3)-triphenylmethyl-4,5,6,7-tetrahydro-1H-benzimidazol-5-yl)ethanol (1.0 g, 2.45 mmol, prepared as described in Example 30) and dry pyridine (10 ml) was placed under an atmosphere of nitrogen and on an ice-bath. Methanesulfonyl chloride (0.5 g, 4.2 mmol) was added dropwise at 0° C. The ice-bath was removed and the mixture was stirred at ambient temperature for 2 hours. The volatiles were evaporated and the residue was stirred with a mixture of diethyl ether (100 ml) and H$_2$O (100 ml). The phases were separated and the organic phase was washed with H$_2$O (20 ml) and brine and dried (Na$_2$SO$_4$). The solvent was evaporated and the residue was dried in vacuo to give 1 g of crude methanesulfonic acid 2-(1(3)-triphenylmethyl-4,5,6,7-tetrahydro-1H-benzimidazol-5-yl)ethyl ester. This mesylate (1 g) was stirred with a 0.5 M lithium cyanide solution in DMF (10 ml, 5 mmol) under an atmosphere of nitrogen. Potassium iodide (approx. 0.2 g) was added and the mixture was stirred at 85° C. overnight. The volatiles were evaporated and the residue was treated with H$_2$O (100 ml) and ethyl acetate (150 ml). The phases were separated and the organic phase was washed with water and brine and dried (magnesium sulphate). The solvent was evaporated and the residue was re-evaporated with acetonitrile to give crude 3-(1(3)-triphenylmethyl-4,5,6,7-tetrahydro-1H-benzimidazol-5-yl)propionitrile. 90% Acetic acid (40 ml) was added and the mixture was heated at reflux for 1 hour. The volatiles were evaporated and the residue was stirred with a mixture of 1 N hydrochloric acid (10 ml) and H$_2$O (50 ml). The mixture was washed with diethyl ether (3×50 ml). The aqueous phase was evaporated to dryness and the residue was dissolved in 1 N hydrochloric acid (25 ml) and re-evaporated. The residue was re-evaporated with acetonitrile (2×) and dried to give 350 mg (68%) of 3-(4,5,6,7-tetrahydro-1H-benzimidazol-5-yl)propionitrile hydrochloride.

$^1$H NMR (DMSO-d$_6$, 400 MHz): δ 1.40–1.52 (m, 1H), 1.70 (q, 2H), 1.85–2.00 (m, 2H), 2.25–2.35 (m, 1H), 2.55–2.70 (m, 4H), 2.76 (dd, 1H), 8.91 (s, 1H), 14.45 (brs, 2H).

Step 2: 3-(4,5,6,7-Tetrahydro-1H-benzimidazol-5-yl) propionic Acid Ethyl Ester Hydrochloride

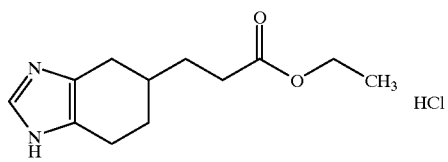

A solution of 3-(4,5,6,7-tetrahydro-1H-benzimidazol-5-yl)propionitrile hydrochloride (340 mg, 1.6 mmol) in 6 N hydrochloric acid (25 ml) was heated at reflux overnight. The volatiles were evaporated and the residue was re-evaporated with acetonitrile. The residue was stirred with acetonitrile and the solid was isolated and dried to give 370 mg of crude 3-(4,5,6,7-tetrahydro-1H-benzimidazol-5-yl) propionic acid hydrochloride. A mixture of this acid (370 mg) and ethanol (10 ml) was placed on an ice-bath under an atmosphere of nitrogen and thionylchloride (0.2 ml) was added dropwise. When addition was complete, the mixture was stirred for 30 minutes and then heated at reflux for 1 hour. The solvent was evaporated and the residue was re-evaporated with acetonitrile and then stirred with acetonitrile (20 ml). The resulting mixture was filtered and the solid was discarded. From the filtrate the solvent was evaporated and the residue was dried to give 320 mg (77%) of 3-(4,5,6,7-tetrahydro-1H-benzimidazol-5-yl)propionic acid ethyl ester hydrochloride.

Mp. 160–162° C. $^1$H NMR (DMSO-d$_6$, 400 MHz): δ 1.18 (t, 3H), 1.38–1.50 (m, 1H), 1.57–1.72 (m, 2H), 1.72–1.85 (m, 1H), 1.85–1.95 (m, 1H), 2.18–2.29 (m, 1H), 2.40 (t, 2H), 2.55–2.75 (m, 3H), 4.05 (q, 2H), 8.89 (s, 1H), 14.4 (brs, 2H).

Step 3: 3-(1(3)-Triphenylmethyl-4,5,6,7-tetrahydro-1H-benzimidazol-5-yl)-1-propanol

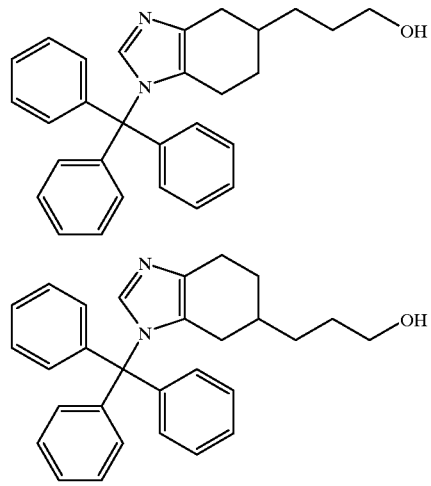

To a mixture of 3-(4,5,6,7-tetrahydro-1H-benzimidazol-5-yl)propionic acid ethyl ester hydrochloride and acetonitrile (20 ml) was added triethylamine (0,35 ml, 2.5 mmol) followed by portionwise addition of triphenylmethylchloride (376 mg, 1.35 mmol). When addition was complete the mixture was stirred overnight at ambient temperature. The volatiles were evaporated and the residue was stirred with a mixture of ethyl acetate (50 ml) and H$_2$O (25 ml). The phases were separated and the organic phase was dried (magnesium sulphate) and the solvent was evaporated. The residue was re-evaporated with THF and then dissolved in dry THF (20 ml). The resulting solution was placed under an atmosphere of nitrogen and 1 N lithiumaluminium hydride in THF (1.2 ml, 1.2 mmol) was added dropwise. When addition was complete the mixture was stirred at ambient temperature for 2 hours. The mixture was quenched with a few drops of water and a few drops of 4 N sodium hydroxide and ethyl acetate was added (100 ml) followed by magnesium sulphate. The mixture was stirred for 15 minutes and then filtered. The solvent was evaporated to give a residue that was crystallised from ethyl acetate. This afforded 280 mg (55%) of 3-(1(3)-triphenylmethyl-4,5,6,7-tetrahydro-1H-benzimidazol-5-yl)-1-propanol.

HPLC method E: elution at 6.93 and 7.33 min.

Step 4

Using a procedure similar to that described in Example 1 and starting from 3-(1(3)-triphenylmethyl-4,5,6,7-tetrahydro-1H-benzimidazol-5-yl)-1-propanol (100 mg, 0.24 mmol) and 4-chlorophenol (48 mg, 0.38 mmol), 60 mg (78%) of the title compound was obtained.

Mp. 225–226° C. HPLC method D: elution at 16.34 min.

Example 35

4-[3-(4,5,6,7-Tetrahydro-1H-benzimidazol-5-yl)propoxy] benzonitrile hydrochloride

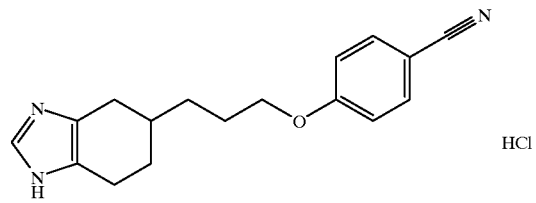

Using a procedure similar to that described in Example 34 and starting from 3-(1(3)-triphenylmethyl-4,5,6,7-tetrahydro-1H-benzimidazol-5-yl)-1-propanol (100 mg, 0.24 mmol) and 4-cyanophenol (45 mg, 0.38 mmol), 50 mg (66%) of the title compound was obtained.

Mp. 229–231° C. HPLC method D: elution at 12.39 min.

Example 36

5-(2-Benzyloxyethyl)-4,5,6,7-tetrahydro-1H-benzimidazole Hydrochloride

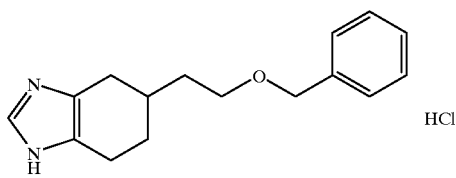

A mixture of dry DMF (5 ml), benzylalcohol (216 mg, 2.0 mmol) and 60% sodium hydride (80 mg, 2.0 mmol) placed under an atmosphere of nitrogen was heated at 50° C. for 30 minutes. The mixture was allowed to cool to ambient temperature and methanesulfonic acid 2-(1(3)-triphenylmethyl-4,5,6,7-tetrahydro-1H-benzimidazol-5-yl) ethyl ester (0.5 g, 1.2 mmol, prepared as described in Example 34) dissolved in dry DMF (5 ml) was added and the reaction mixture was stirred for 2 days. The mixture was poured into $H_2O$ (100 ml) and extracted with diethyl ether (2×50 ml). The combined organic extracts were washed with $H_2O$ (3×50 ml) and the solvent was evaporated. The residue was dissolved in 90% acetic acid (20 ml) and the mixture was heated at reflux for 1–2 hours. The volatiles were evaporated and the residue was stirred with a mixture of $H_2O$ (25 ml) and diethyl ether (20 ml). The phases were separated and the aqueous phase was washed with diethyl ether (2×20 ml). The aqueous phase was adjusted to pH 10–11 with 4 N sodium hydroxide and the oily precipitate was extracted with ethyl acetate (2×20 ml). The combined organic extracts were evaporated and the residue was dissolved in 1 N hydrochloric acid and re-evaporated. The residue was re-evaporated with acetone several times and then stirred with acetonitrile (5 ml). The mixture was filtered and the solid was discarded. The filtrate was evaporated to give 110 mg (31%) of the title compound.

$^1$H NMR (DMSO-$d_6$, 400 MHz): δ 1.40–1.55 (m, 1H), 1.55–1.75 (m, 1H), 1.85–2.10 (m, 3H), 2.22–2.35 (m, 1H), 2.55–2.80 (m, 3H), 3.55 (t, 2H), 4.48 (s, 2H), 7.15–7.40 (m, 5H), 8.88 (s, 1H), 14.4 (brs, 2H).

Example 37

5-Benzyloxy-4,5,6,7-tetrahydro-1H-benzimidazole

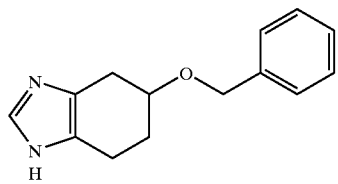

Step 1: 4-Methoxycyclohex-3-enol

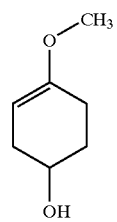

The preparation of -methoxycyclohex-3-enol was done as described in Okamura, W. H., Elnagar, H. Y., Ruther, M., Dobreff, S. *J. Org. Chem.* 1993, 58, 600–601.

At −33° C., lithium (5.0 g, 720 mmol) was added to liquid ammonia (200 ml). A solution of p-methoxyphenol (8.0 g, 32.2 mmol) in diethyl ether (50 ml) was added over a period of 5 min. to the blue solution. The reaction mixture was stirred for 45 min at −33° C. Ethanol (3.8 ml) was added. The reaction mixture was stirred for 1 hour at −33° C. Ethanol (8 ml) was added. The reaction mixture was stirred for 30 hours at −33° C. The latter procedure was repeated three times, until a colourless solution was obtained. Solid ammonium chloride (20 g) was added. The reaction mixture was left open at room temperature for 16 hours, until the ammonia was evaporated. Water (200 ml) was added. The solution was extracted with ethyl acetate (6×150 ml). The combined organic extracts were dried over magnesium sulphate. The solvent was removed in vacuo. The crude product was purified by flash chromatography on silica (300 g), using ethyl acetate/heptane 1:1 as eluent, to give 3.61 g of 4-methoxyyclohex-3-enol, which was slightly contaminated with 4-hydroxycyclohexanone.

$^1$H NMR (CDCl$_3$): δ 1.70–2.70 (m, 7 H); 3.55 (s, 3 H); 3.95 (m, 1 H); 4.50 (t, 1 H).

Step 2: ((4-(Methoxy)cyclohex-3-enyloxy)methyl)benzene

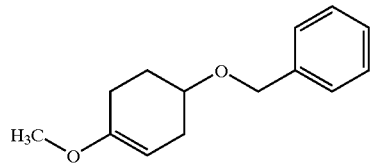

4-Methoxycyclohex-3-enol (3.60 g, 28.09 mmol), which was prepared as described in the previous step, was dissolved in THF (150 ml). Sodium hydride (60% in mineral oil, 2.8 g, 64.37 mmol) was given to the solution. The reaction mixture was stirred for 30 min at room temperature. Tetrabutylammonium iodide (1.0 g, 2.809 mmol) was added. Benzyl bromide (6.7 ml, 56.18 mmol) was added. The reaction mixture was stirred for 16 hours at room temperature. Water (200 ml) was added carefully. The phases were separated. The aqueous phase was extracted with ethyl acetate (3×100 ml). The combined organic layers were washed with a saturated aqueous solution of sodium hydrogencarbonate (200 ml) and dried over magnesium sulphate. The solvent was removed in vacuo. The crude product was purified by flash chromatography on silica (200 g), using ethyl acetate/heptane 1:1 as eluent, to give 4.0 g of ((4-(methoxy)cyclohex-3-enyloxy)methyl)benzene, which was slightly contaminated with 4-benzyloxycyclohexanone.

$^1$H NMR (CDCl$_3$): δ 1.70–2.50 (m, 6 H); 3.50 (s, 3 H); 3.65 (m, 1 H); 4.50 (m, 1 H); 4.60 (m, 2 H); 7.10–7.50 (m, 5 H).

Step 3: 4-Benzyloxy-2-bromocyclohexanone

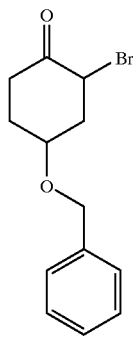

A solution of bromine (0.56 ml, 10.90 mmol) in DCM (30 ml) was added dropwise to a solution of ((4-(methoxy) cyclohex-3-enyloxy)methyl)benzene (3.4 g, 15.57 mmol), which was prepared as described in the last step, in DCM (100 ml). The reaction mixture was stirred for 1 hour at room temperature. Tert-butyl methyl ether (150 ml) was added. The solution was washed with ice cooled water (200 ml), a saturated aqueous solution of sodium thiosulphate (100 ml), and a saturated aqueous solution of sodium hydrogencarbonate. The organic layer was dried over magnesium sulphate. The solvent was removed in vacuo. The crude product was purified by flash chromatography on silica (90 g), using ethyl acetate/heptane (1:2) as eluent, to give 1.40 g of a mixture of diastereoisomeres of 4-benzyloxy-2-bromocyclohexanone.

$^1$H NMR (CDCl$_3$, major diastereoisomer): δ 1.70–2.90 (m, 6 H); 3.95 (m, 1 H); 4.65 (m, 2 H); 4.85 (dd, 1 H); 7.35 (m, 1 H).

Step 4

A mixture of diastereoisomeres of 4-benzyloxy-2-bromocyclohexanone (1.60 g, 10.59 mmol) and formamide (7 ml) was heated for 1.5 hours to 150° C. At was cooled to room temperature and stirred at room temperature for 16 hours. Water (100 ml) was added. It was washed with ethyl acetate. The aqueous phase was made basic (pH 13) with a 1 N sodium hydroxide solution. It was extracted with tert-butyl methyl ether (3×70 ml). The tert-butyl methyl ether phase was dried over magnesium sulphate. The solvent was removed in vacuo to give 195 mg of the title compound.

HPLC method C: elution at 7.38 min. MS: Calc for [M+H]$^+$: 229; Found: 229. $^1$H NMR (CDCl$_3$): δ 2.00 (m,1 H); 2.10 (m, 1 H); 2.60 (m, 1 H); 2.75 (m, 2 H); 3.00 (dd, 1 H); 3.90 (m, 1 H); 4.62 (s, 2 H); 7.20–7.40 (m, 5 H); 7.45 (s, 1 H).

For biological testing, the title compound was transferred into its hydrochloride salt, by dissolving in ethyl acetate (100 ml) and addition of hydrogen chloride in ethyl acetate (3.0 M, 20 ml). The precipitation was collected.

Microanalysis for C$_{14}$H$_{16}$N$_2$O, HCl, H$_2$O (282.78):

Calc: C: 59.47%; H: 6.77%; N: 9.91%;

Found: C: 59.47%; H: 6.78 N: 11.03%.

Example 38
5-((Biphenyl-2-yl)methoxymethyl)-4,5,6,7-tetrahydro-1H-benzimidazole

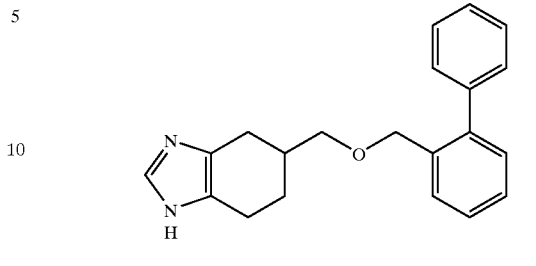

Step 1: 5-((Biphenyl-2-yl)methoxymethyl)-1-(triphenylmethyl)-4,5,6,7-tetrahydro-1H-benzimidazole and 5-((Biphenyl-2-yl)methoxymethyl)-3-(triphenylmethyl)-4,5,6,7-tetrahydro-3H-benzimidazole, hydrochlorides

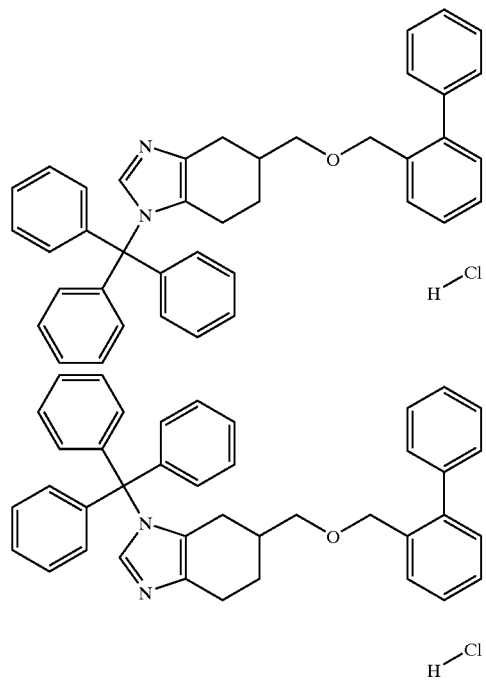

A 60% dispersion of sodium hydride in mineral oil (0.24 g, 6.1 mmol) was added to a solution of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (2.0 g, 5.1 mmol) in THF (100 ml). After the reaction had ceased, tetrabutylammonium iodide (0.10 g, 0.25 mmol) and 2-(bromomethyl) biphenyl (1.0 ml; 5.6 mmol) were added subsequently. The reaction mixture was stirred for 16 hours at room temperature. Water (200 ml) was added carefully. The mixture was extracted with ethyl acetate (3×150 ml). The combined organic layers were washed with a saturated solution of sodium hydrogencarbonate (200 ml) and dried over magnesium sulphate. The solvent was removed in vacuo. The crude product was purified by flash chromatography on silica, using first ethyl acetate/heptane (1:1) and then DCM/methanol/25% aqueous ammonia (first: 200:10:1, then: 100:10:1) as eluent, to give 0.24 g of a mixture of 5-((biphenyl-2-yl)methoxymethyl)-1-(triphenylmethyl)-4,5,6,7-tetrahydro-1H-benzimidazole and 5-((biphenyl-2-yl)methoxymethyl)-3-(triphenylmethyl)-4,5,6,7-tetrahydro-3H-benzimidazole.

$^1$H NMR (CDCl$_3$): δ 1.30 (m, 2 H); 1.70 (m, 2 H); 1.95 (m,1 H); 2.35 (dd, 1 H); 2.70 (dd, 1 H); 3.20 (dd, 1 H); 3.35 (dd, 1 H); 4.35 (AB, 2 H); 6.80–7.50 (m, 25 H).

Step 2

A mixture of 5-((biphenyl-2-yl)methoxymethyl)-1-(triphenylmethyl)-4,5,6,7-tetrahydro-1H-benzimidazole and 5-((biphenyl-2-yl)methoxymethyl)-3-(triphenylmethyl)-4,5,6,7-tetrahydro-3H-benzimidazole (0.24 g, 0.43 mmol) was dissolved in a mixture of acetic acid (9 ml) and water (1 ml). The reaction mixture was stirred at 90° C. for 2 hours. The solvent was removed in vacuo. The residue was dissolved in ethyl acetate (10 ml). A 3.5 M solution of hydrogen chloride in ethyl acetate (0.13 ml) was added. The solvent was removed in vacuo. The residue was dissolved in acetone (10 ml). The crystals were isolated, washed with acetone (2×5 ml) and dried in vacuo to give 94 mg of the hydrochloride salt of the title compound.

HPLC method C: elution at 10.14 min. MS: Calc for [M+H]$^+$: 319; Found: 319. $^1$H NMR (DMSO-d$_6$): δ 1.50 (m, 1 H); 1.95 (m, 1 H); 2.05 (m, 1 H); 2.30 (dd, 1 H); 2.60 (m, 2 H); 2.70 (m, 1 H); 3.35 (d, 2 H); 4.35 (AB 2 H); 7.20–7.60 (m, 9 H); 8.35 (s, 1 H); 14.20 (br, 2 H).

Microanalysis for C$_{21}$H$_{22}$N$_2$O, HCl (354.88):

Calc: C: 71.08%; H: 6.53%; N: 7.89%;

Found: C: 70.32%; H: 6.73%; N: 7.96%.

Example 39

5-((1-Naphthyl)methoxymethyl)-4,5,6,7-tetrahydro-1H-benzimidazole

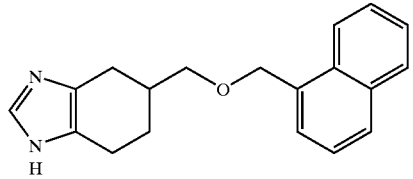

Step 1: 5-((1-Naphthyl)methoxymethyl)-1-(triphenylmethyl)-4,5,6,7-tetrahydrobenzimidazole and 5-((1-naphthyl)methoxymethyl)-3-(triphenylmethyl)-4,5,6,7-tetrahydrobenzimidazole

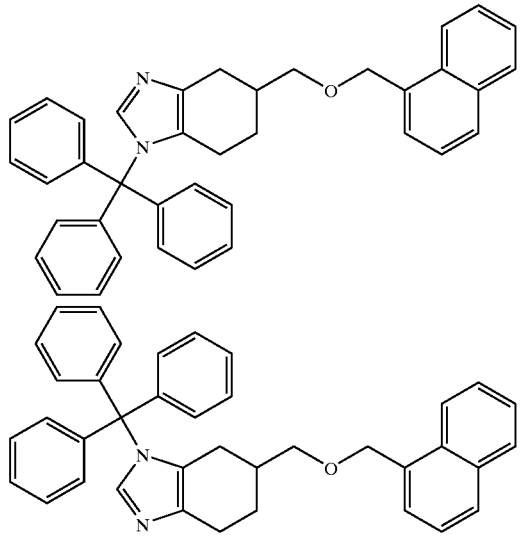

A 60% dispersion of sodium hydride in mineral oil (0.24 g, 6.1 mmol) was added to a solution of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (2.0 g, 5.1 mmol) in THF (100 ml). After the reaction had ceased tetrabutylammonium iodide (0.10 g, 0.25 mmol) and 1-(bromomethyl)naphthalene (1.2 g, 5.8 mmol) were added subsequently. The reaction mixture was stirred for 16 hours at room temp. Water (200 ml) was added carefully. The mixture was extracted with ethyl acetate (3×150 ml). The combined organic layers were washed with a saturated solution of sodium hydrogen carbonate (200 ml) and dried over magnesium sulphate. The solvent was removed in vacuo. The crude product was purified by flash chromatography on silica (90 g), using a gradient of ethyl acetate/heptane (from 50:50 to 100:0) as eluent, to give 400 mg of a mixture of 5-((1-naphthyl)methoxymethyl)-1-(triphenylmethyl)-4,5,6,7-tetrahydrobenzimidazole and 5-((1-naphthyl)methoxymethyl)-3-(triphenylmethyl)-4,5,6,7-tetrahydrobenzimidazole.

$^1$H NMR (CDCl$_3$, 2 sets of signals): δ 1.40 (m, 1 H); 1.70 (m, 2 H); 1.90 (m, 1 H); 2.00 (m,1 H); 2.40, 2.65, and 2.75 (dd, m, and dd, together 2 H); 3.15, 3.25, 3.40, and 3.55 (all dd, together 2 H); 4.75 asnd 4.90 (both s, together 2 H); 7.00–8.10 (m, 23 H).

Step 2

A solution of a mixture of 5-((1-naphthyl)methoxymethyl)-1-(triphenylmethyl)-4,5,6,7-tetrahydrobenzimidazole and 5-((1-naphthyl)methoxymethyl)-3-(triphenylmethyl)-4,5,6,7-tetrahydrobenzimidazole (0.40 mg, 0.75 mmol) in acetic acid (9 ml) and water (1 ml) was stirred at 90° C. for 1.5 hours. The solvent was removed in vacuo. The residue was dissolved in ethyl acetate (10 ml). A 3.5 M solution of hydrogen chloride in ethyl acetate (0.25 ml) was added. The solvent was removed in vacuo. The residue was taken up in acetone. The crystals were isolated, washed with acetone (2×10 ml) and dried in vacuo to give 140 mg of the hydrochloride salt of the title compound.

HPLC method C: elution at 9.48 min. MS: Calc for [M+H]$^+$: 293; Found: 293. $^1$H NMR (DMSO-d$_6$) δ 1.50 (m, 1 H); 2.0 (m,1 H); 2.15 (m, 1 H); 2.35 (dd, 1 H); 2.60 (m, 2 H); 2.75 (dd, 1 H); 3.55 (d, 2 H); 4.95 (s, 2 H); 7.45–7.65 (m, 4 H); 7.90 (d, 1 H); 7.95 (d, 1 H); 8.10 (d, 1 H); 8.80 (s, 1 H); 14.10 (br, 2 H).

Microanalysis for C$_{19}$H$_{20}$N$_2$O, HCl (328.84):

Calc: C: 69.40%; H: 6.44%; N: 8.52%;

Found: C: 68.27%; H: 6.36%; N: 8.24%.

Example 40

5-(4-Trifluoromethylbenzyloxymethyl)-4,5,6,7-tetrahydro-1H-benzimidazole

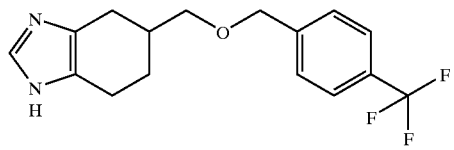

Step 1: 5-(4-Trifluoromethylbenzyloxymethyl)-1-(triphenylmethyl)-4,5,6,7-tetrahydrobenzimidazole and 5-(4-Trifluoromethylbenzyloxymethyl)-3-(triphenylmethyl)-4,5,6,7-tetrahydrobenzimidazole

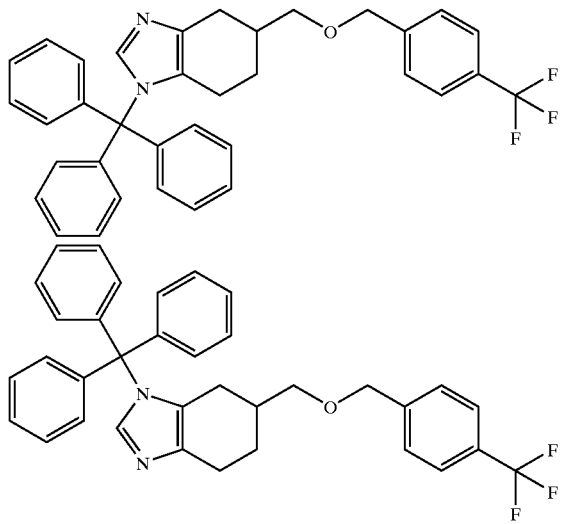

A 60% dispersion of sodium hydride in mineral oil (4.1 g, 101 mmol) was added to a solution of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (2.0 g, 5.1 mmol) in THF (10 ml). After the reaction had ceased, tetrabutylammonium iodide (0.1 g, 0.25 mmol) and 4-trifluoromethylbenzyl bromide (1.3 g, 5.6 mmol) were added subsequently. The reaction mixture was stirred for 16 hours at room temp. Water (100 ml) was added carefully. The mixture was extracted with ethyl acetate (3×80 ml). The combined organic layers were washed with a saturated aqueous solution of sodium hydrogencarbonate (100 ml) and dried over magnesium sulphate. The solvent was removed in vacuo. The crude product was purified by flash chromatography on silica (90 g), using a gradient of ethyl acetate/heptane (from 50:50 to 100:0) as eluent, to give 1.65 g of a mixture of 5-(4-trifluoromethylbenzyloxymethyl)-1-(triphenylmethyl)-4,5,6,7-tetrahydrobenzimidazole and 5-(4-trifluoromethylbenzyloxymethyl)-3-(triphenylmethyl)-4,5,6,7-tetrahydrobenzimidazole.

$^1$H NMR (CDCl$_3$, to sets of signals): δ 1.40 (m, 1 H); 1.60–2.10 (m, 4 H); 2.40, 2.65, and 2.80 (dd, m, and dd, together 2 H); 3.10, 3.20, 3.85, and 3.95 (all dd, together 2 H); 4.35 and 4.52 (both s, together 2 H); 7.00–7.60 (m, 20 H).

Step 2

A solution of a mixture of 5-(4-trifluoromethylbenzyloxymethyl)-1-(triphenylmethyl)-4,5,6,7-tetrahydrobenzimidazole and 5-(4-trifluoromethylbenzyloxymethyl)-3-(triphenylmethyl)-4,5,6,7-tetrahydrobenzimidazole (1.65 g, 3.0 mmol) in acetic acid (9 ml) and water (1 ml) was heated to 80° C. for 2 hours. The solvent was removed in vacuo. The residue was dissolved in ethyl acetate. A 3.5 M solution of hydrogen chloride in ethyl acetate (0.80 ml) was added. The solvent was removed in vacuo. The residue was dissolved in acetone (10 ml). The solvent was removed in vacuo. This latter procedure was repeated 2 times. The resulting crystals were collected to give 0.75 g of the hydrochloride salt of the title compound.

HPLC method C: elution at 9.72 min. MS: Calc for [M+H]$^+$: 311; Found: 311. $^1$H NMR (DMSO-d$_6$): δ 1.51 (m, 1 H), 2.00 (m,1 H); 2.15 (m, 1 H); 2.37 (dd, 1 H); 2.65 (m, 2 H); 2.75 (dd, 1 H); 3.50 (d, 2 H); 4.60 (s, 2 H); 7.55 (d, 2 H); 7.70 (d, 2 H); 8.88 (s, 1 H); 14.20 (br, 2 H).

Microanalysis for C$_{16}$H$_{17}$F$_3$N$_2$O, HCl (310.32, 36.46):
Calc: C: 55.42%; H: 5.23%; N: 8.08%;
Found: C: 56.13%; H: 5.42%; N: 7.87%.

Example 41

5-((3-(Trifluoromethyl)benzyloxy)methyl)-4,5,6,7-tetrahydro-1H-benzimidazole

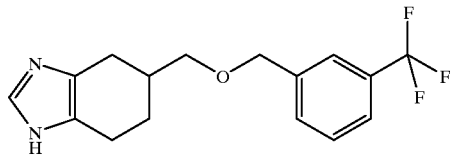

Step 1: 5-((3-(Trifluoromethyl)benzyloxy)methyl)-1-triphenylmethyl-4,5,6,7-tetrahydro-1H-benzimidazole and 5-((3-(trifluoromethyl)benzyloxy)methyl)-3-triphenylmethyl-4,5,6,7-tetrahydro-1H-benzimidazole

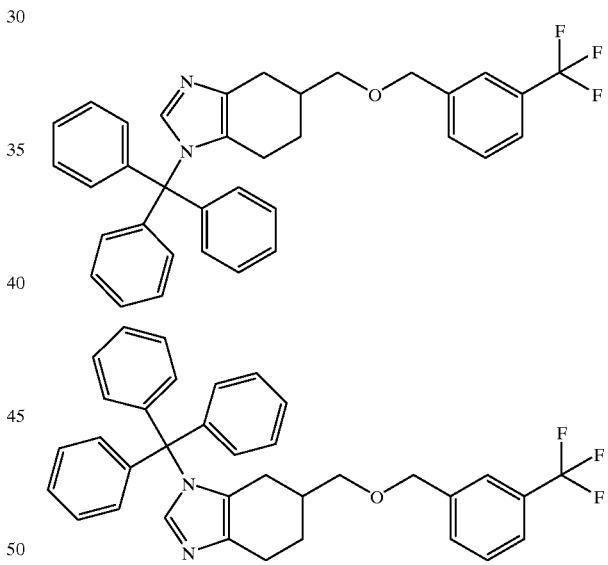

A 60% dispersion of sodium hydride in mineral oil (3.04 g, 76 mmol) was added portionwise to a solution of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol 1.50 g, 3.80 mmol) in THF (10 ml). After the reaction had ceased tetrabutylammonium iodide (0.07 g, 0.19 mmol) and 3-(trifluoromethyl)benzyl bromide (0.64 ml, 4.18 mmol) were added subsequently. The reaction mixture was stirred for 16 hours at room temperature. Water (50 ml) was added carefully. The mixture was extracted with ethyl acetate (3×100 ml). The combined organic layers were washed with a saturated aqueous solution of sodium hydrogen carbonate (100 ml) and dried over magnesium sulphate. The solvent was removed in vacuo. The crude product was purified by flash chromatography on silica (90 g), using a gradient of ethyl acetate/heptane (from 50:50 to 100:0) as eluent, to give 1.50 g of a mixture of 5-((3-(trifluoromethyl)benzyloxy)methyl)-1-triphenylmethyl-4,5,6,7-tetrahydro-1H-benzimidazole and 5-((3-(trifluoromethyl)benzyloxy)methyl)-3-triphenylmethyl-4,5,6,7-tetrahydro-3H-benzimidazole.

$^1$H NMR (CDCl$_3$, 2 sets of signals): δ 1.45 (m, 1 H); 1.75 (m, 2 H); 1.85–2.10 (m, 2 H); 2.40, 2.70, and 2.80 (dd, m, and dd, together 2 H); 3.15, 3.20, 3.35, and 3.45 (m, m, dd, and dd, together 2 H); 4.37 and 4.52 (both s, together 2 H); 7.20–7.60 (m, 20 H).

Step 2

A mixture of 5-((3-(trifluoromethyl)benzyloxy)methyl)-1-triphenylmethyl-4,5,6,7-tetrahydro-1H-benzimidazole and 5-((3-(trifluoromethyl)benzyloxy)methyl)-3-triphenylmethyl-4,5,6,7-tetrahydro-3H-benzimidazole (1.50 g, 2.71 mmol) was dissolved in a mixture of acetic acid (9 ml) and water (1 ml). The reaction mixture was heated to 80° C. for 2 hours. The solvent was removed in vacuo. The residue was dissolved in ethyl acetate (10 ml). A 3.5 M solution of hydrogen chloride in ethyl acetate (0.80 ml, 2.8 mmol) was added. The solvent was removed in vacuo. Acetone (10 ml) was added. The solvent was removed in vacuo. Acetone (10 ml) was added. The resulting precipitation was collected and dried in vacuo to give 0.70 g of the hydrochloride of the title compound.

HPLC method C: elution at 9.49 min. MS: Calc for [M+H]$^+$: 325; Found: 325. $^1$H NMR (DMSO-d$_6$): δ 1.53 (m, 1 H); 2.00 (m, 1 H); 2.15 (m, 1 H); 2.35 (dd, 1 H); 2.65 (m, 2 H); 2.75 (dd, 1 H); 3.50 (d, 2 H); 4.60 (s, 2 H); 7.65 (m, 4 H); 8.90 (s, 1 H).

Microanalysis for C$_{16}$ H$_{17}$F$_3$N$_2$O, HCl (310.32, 36.46):
Calc: C: 55.42%; H: 5.23%; N: 8.08%;
Found: C: 55.63%; H: 5.26%; N: 7.90%.

Example 42
5-((2-Phenoxybenzyloxy)methyl)-4,5,6,7-tetrahydro-1H-benzimidazole

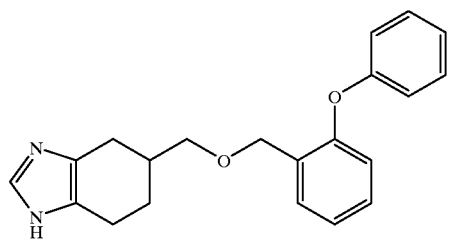

Step 1: 2-Phenoxybenzoic Acid Methyl Ester

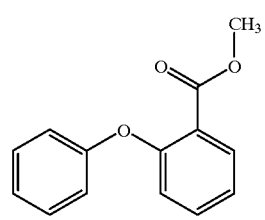

Thionyl chloride (2.0 ml, 28.0 mmol) was added dropwise to a solution of 2-phenoxybenzoic acid (5.0 g, 23.3 mmol) in methanol (70 ml). The reaction mixture was stirred at 70° C. for 3 hours. The solvent was removed in vauco. The crude product was used in the next step without further purification.

$^1$H NMR (CDCl$_3$): δ 3.80 (s, 3 H); 6.95 (m, 3 H); 7.05 (t,1 H); 7.15 (t, 1 H); 7.30 (t, 2 H); 7.45 (t, 1 H); 7.90 (d, 1 H).

Step 2: 2-Phenoxybenzylalcohol

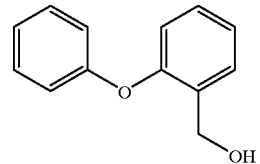

A 1.0 M solution of lithium aluminum hydride in THF (25 ml, 25 mmol) was added to a solution of crude 2-phenoxybenzoic acid methyl ester (5.23 g, 22.9 mmol) in THF. The reaction mixture was stirred for 2.5 hours at room temperature. Methanol (10 ml) was added carefully. THF (50 ml) was added. Magnesium sulphate was added. The solids were filtered off. The solvent was removed in vacuo. The crude product was purified by flash chromatography on silica (90 g), using ethyl acetate/heptane (1:1) as eluent, to give 4.08 g of 2-phenoxybenzylalcohol.

$^1$H NMR (CDCl$_3$) δ 4.70 (m, 2 H); 6.85 (d, 1 H); 6.97 (d, 2 H); 7.10 (m, 2 H); 7.25 (t, 1 H); 7.35 (t, 2 H); 7.45 (d, 1 H).

Step 3: 2-Phenoxybenzyl bromide

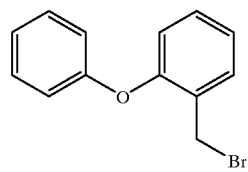

Phosphorus tribromide (5.5 ml, 57.1 mmol) was added dropwise over a period of 10 min to a solution of 2-phenoxybenzylalcohol (4.08 g, 20.4 mmol) in dioxane (165 ml). The reaction mixture was stirred for 40 min. Another portion of phosphorus tribromide (5.5 ml, 57.1 mmol) was added. The reaction mixture was stirred for 56 hours at room temperature. It was cooled to 0° C. Water (45 ml) was added carefully. The reaction mixture was stirred for 30 min at room temperature. The mixture was extracted with ethyl acetate (100 ml). The ethyl acetate phase was washed with 1 N hydrochloric acid. The combined aqueous layers were extracted with ethyl acetate. The combined organic layers were washed with a saturated aqueous soludtion of sodium hydrogen carbonate (100 ml) and dried over magnesium sulphate. The solvent was removed in vacuo. The crude product was purified by flash chromatography on silica (90 g), using ethyl acetate/heptane (1:3) as eluent, to give 4.80 g of 2-phenoxybenzyl bromide.

$^1$H NMR (CDCl$_3$): δ 4.60 (s, 2 H); 6.85 (d, 1 H); 7.10 (m, 4 H); 7.25 (t, 1 H); 7.35 (m, 2 H); 7.45 (d, 1 H).

Step 4: 5-((2-Phenoxybenzyloxy)methyl)-1-triphenylmethyl-4,5,6,7-tetrahydro-1H-benzimidazole and 5-((2-Phenoxybenzyloxy)methyl)-3-triphenylmethyl-4,5,6,7-tetrahydro-3H-benzimidazole

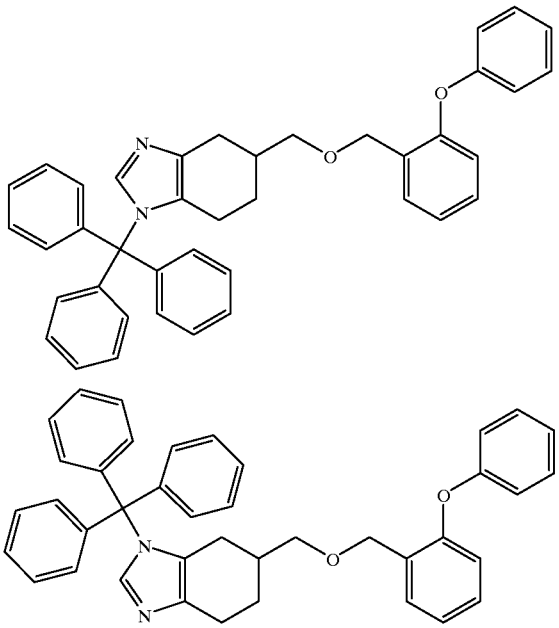

A 60% suspension of sodium hydride in mineral oil (4.1 g, 101 mmol) was added to a solution of a mixture of (1-(triphenylmethyl)-4,5,6,7-tetrahydro-1H-benzimidazol-5-yl)-methanol and (3-(triphenylmethyl)-4,5,6,7-tetrahydro-3H-benzimidazol-5-yl)methanol (2.0 g, 5.1 mmol) in THF (8 ml). When the reaction had ceased tetrabutylammonium iodide (0.10 g, 0.25 mmol) and a solution of 2-phenoxybenzyl bromide (1.5 g, 5.6 mmol) in THF (5 ml) were added successively. The reaction mixture was stirred for 16 h. Water (100 ml) was added carefully. The mixture was extracted with ethyl acetate (3×60 ml). The combined organic layers were washed with a saturated aqueous solution of sodium hydrogen carbonate (100 ml) and dried over magnesium sulphate. The solvent was removed in vacuo. The crude product was purified by flash chromatography on silica (90 g), using ethyl acetate/heptane (gradient from 50:50 to 100:0) as eluent, to give 1.21 g of 5-((2-phenoxybenzyloxy)methyl)-1-triphenylmethyl-4,5,6,7-tetrahydro-1H-benzimidazole and 5-((2-phenoxybenzyloxy)methyl)-3-triphenylmethyl-4,5,6,7-tetrahydro-3H-benzimidazole.

$^1$H NMR (CDCl$_3$, 2 sets of signals): δ 1.10–1.50 (m, together 2 H); 1.60–2.00 (m, together 3 H); 2.35, 2.65, and 2.75 (dd, m, and dd, together 2 H); 3.15, 3.30, and 3.45 (m, t, and dd, together 2 H); 4.40 and 4.50 (both AB, together 2 H); 6.80–7.55 (m, together 25 H).

Step 5

A mixture of 5-((2-phenoxybenzyloxy)methyl)-1-triphenylmethyl-4,5,6,7-tetrahydro-1H-benzimidazole and 5-((2-phenoxybenzyloxy)methyl)-3-triphenylmethyl-4,5,6,7-tetrahydro-3H-benzimidazole (1.20 g, 2.1 mmol) was dissolved in a mixture of acetic acid (9 ml) and water (1 ml). The mixture was heated to 90° C. for 2 hours. The solvent was removed in vacuo. The residue was dissolved in ethyl acetate (10 ml). a 3.5 M solution of hydrogen chloride in ethyl acetate (0.60 ml) was added. The solvent was removed in vacuo. The crude product was purified by flash chromatography on silica (40 g), using DCM/methanol/25% aqueous ammonia (first: 100:10:1, then 100:20:2) as eluent to give 74 mg of the title compound. For biological testing, the title compound was transferred into its hydrochloride salt by lyophilization of its solution in 0.1 N hydrochloric acid (40 ml).

HPLC method C: elution at 10, 18min. $^1$H NMR (DMSO-d$_6$) δ 1.45 (m,1 H); 1.95 (m, 1 H); 2–05 (m, 1 H); 2.30 (dd, 1 H); 2.55 (m, 2 H); 2.70 (dd, 1 H); 3.40 (d, 2 H); 4.50 (s, 2 H); 6.90 (m, 3 H); 7.10 (t, 1 H); 7.20 (t, 1 H); 7.35 (m, 3 H); 7.50 (d, 1 H); 8.90 (s, 1 H); 14.40 (br, 1 H).

MS: Calc for [M+H]$^+$: 335; Found: 335.

Microanalysis for C$_{21}$H$_{22}$N$_2$O$_2$, HCl, H$_2$O (334.42, 36.46, 18.02):

Calc: C: 64.86%; H: 6.48%; N: 7.20%;

Found: C: 63.31%; H: 6.23%; N: 7.23%.

Example 43

6-Phenoxymethyl-3,4,6,7-tetrahydropyrano[3,4-d]imidazole

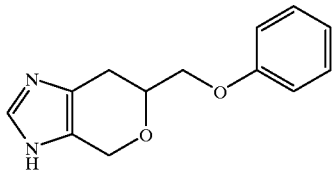

Step 1: Phenoxyacetaldehyde

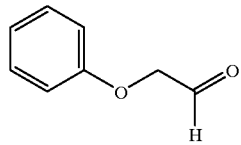

At −78° C., a solution of dimethylsulphoxide (5.11 ml, 72 mmol) in DCM (50 ml) was added dropwise to a solution of oxalyl chloride (6.12 ml, 72 mmol) in DCM (150 ml). The reaction mixture was stirred for 10 min at −78° C. A solution of 2-phenoxyethanol (10.0 g, 72 mmol) in DCM (70 ml) was added dropwise. The reaction mixture was stirred at −78° C. for 10 min. A solution of triethylamine (50 ml, 360 mmol) in DCM (50 ml) was added dropwise. The reaction mixture was stirred for 10 min at −78° C. It was warmed to room temperature. The reaction mixture was washed with a 10% aqueous solution of sodium hydrogensulphate (2×200 ml) and subsequently with brine (2×200 ml). It was dried over magnesium sulphate. The solvent was removed in vacuo. The crude product was purified by flash chromatography on silica (100 g), using ethyl acetate/heptane (1:3) as eluent, to give 2.73 g of phenoxyacetaldehyde.

$^1$H NMR (CDCl$_3$): δ 4.55 (s, 2 H); 7.00 (m, 3 H); 7.30 (m, 2 H); 9.90 (s, 1 H).

Step 2: 2-Phenoxymethyl-2,3-dihydropyran-4-one

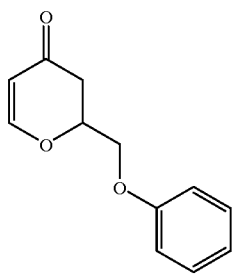

1-Methoxy-3-(trimethylsilyloxy)-1,3-butadiene (4.95 ml; 26 mmol) was added to a solution of phenoxyacetaldehyde (3.56 g, 26 mmol) in DCM (40 ml). The solution was cooled to −5° C. A 2.3 M solution of zinc chloride in DCM (5.6 ml, 13 mmol) was added. The reaction mixture was stirred for 16 hours, while it was warming up to room temperature. It was diluted with ethyl acetate (150 ml) and washed with a 10% aqueous solution of sodium hydrogensulphate (100 ml). The aqueous phase was extracted with ethyl acetate (100 ml). The combined organic layers were washed with a saturated aqueous solution of sodium hydrogencarbonate (100 ml) and dried over magnesium sulphate. The solvent was removed in vacuo. The crude product was purified by flash chromatography on silica (200 g), using ethyl acetate/heptane (1:1) as eluent, to give 2.36 g of 2-phenoxymethyl-2,3-dihydropyran-4-one.

$^1$H NMR (CDCl$_3$): δ 2.55 (dd, 1 H); 2.87 (dd, 1 H); 4.20 (m, 2 H); 4.80 (dddd, 1 H); 5.50 (d, 1 H); 6.95 (m, 3 H); 7.80 (m, 2 H); 7.40 (d, 1 H).

Step 3: 2-Phenoxymethyltetrahydropyran-4-one

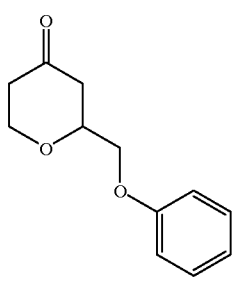

2-Phenoxymethyl-2,3-dihydropyran-4-one (2.30 g, 11.3 mmol) was dissolved in ethyl acetate (150 ml). 10% Palladium on charcoal (400 mg) was added. The reaction mixture was hydrogenated until the reaction stopped. The catalyst was removed by filtration through a glas-filter. The solvent was removed in vacuo. The crude product was purified by flash chromatography on silica (200 g), using ethyl acetate/heptane 1:1 as eluent, to give 1.36 g of 2-phenoxymethyltetrahydropyran-4-one.

$^1$H NMR (CDCl$_3$): δ 2.35–2.80 (m, 4 H); 3.80 (dt, 1 H); 4.10 (m, 3 H); 4.40 (dd, 1 H); 6.95 (m, 3 H); 7.30 (m, 2 H).

Step 4: 5-Bromo-2-(phenoxymethyl)tetrahydropyran-4-one

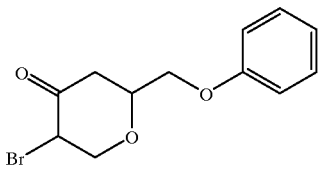

A solution of 2-phenoxymethyltetrahydropyran-4-one (1.36 g, 6.6 mmol) and copper(II) bromide (2.95 g, 13.2 mmol) in THF (20 ml) was heated to reflux for 1 hour. The reaction mixture was cooled to room temperature. The precipitation was removed by filtration. The solution was diluted with tert-butyl methyl ether (100 ml), and washed with a saturated aqueous solution of sodium hydrogencarbonate (100 ml). The aqueous phase was extracted with tert-butyl methyl ether. The organic layers were combined and dried over magnesium sulphate. The solvent was removed in vacuo. The crude product was purified by flash chromatography on silica (100 g), using ethyl acetate/heptane 1:3 as eluent, to give 498 mg of 5-bromo-2-(phenoxymethyl)tetrahydropyran-4-one.

$^1$H NMR (CDCl$_3$): δ 2.88 (m, 2 H); 3.80 (m, 2 H); 4.10 (m, 2 H); 4.55 (m, 1 H); 4.70 (m,1 H); 6.90 (m, 3 H); 7.25 (m, 2 H).

Step 4

A suspension of 5-bromo-2-(phenoxymethyl)tetrahydropyran-4-one (498 mg, 1.75 mmol) in formamide (6 ml) was heated to 150° C. for 1.5 hours. The reaction mixture was cooled to room temperature and stirred at this temperature for 16 hours. It was diluted with water (30 ml) and extracted with ethyl acetate (2×50 ml). The aqueous solution was made basic with a 1 N aqueous solution of sodium hydroxide (pH 14). It was extracted with tert-butyl methyl ether (3×50 ml). The combined tert-butyl methyl ether extracts were dried over magnesium sulphate. The solvent was removed in vacuo to give 31 mg of the title compound.

HPLC method C: elution at 7.09 min. MS: Calc for [M+H]$^+$: 231; Found: 231. $^1$H NMR (CDCl$_3$): δ 2.70 (m, 2 H); 4.10 (m, 2 H); 4.20 (m, 1 H); 4.80 (AB, 2 H); 6.95 (m, 3 H); 7.30 (m, 2 H); 7.50 (s, 1 H).

In order to obtain a water soluable salt of the title compound, it was lyophilized with 0.5 N hydrochloric acid (30 ml). The product was dissolved in water and the solution was applied to a 0.25 g Seppack® cartridge, which was pretreated with acetonitrile (10 ml), a solution of 50% acetonitrile in water (10 ml) and a 0.1% solution of trifluoracetic acid in water (10 ml). It was washed out with a 0.1% solution of trifluoracetic acid in water (10 ml) and subsequently a 15% solution of acetonitrile in a 0.1% solution of trifluoracetic acid in water. The solution was taken and lyophilized.

Example 44

5-Allyloxymethyl-4,5,6,7-tetrahydro-1H-benzimidazole

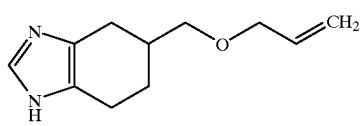

Step 1: Allyloxy-1-triphenylmethyl-4,5,6,7-tetrahydro-1H-benzimidazole and allyloxy-3-triphenylmethyl-4,5,6,7-tetrahydro-3H-benzimidazole

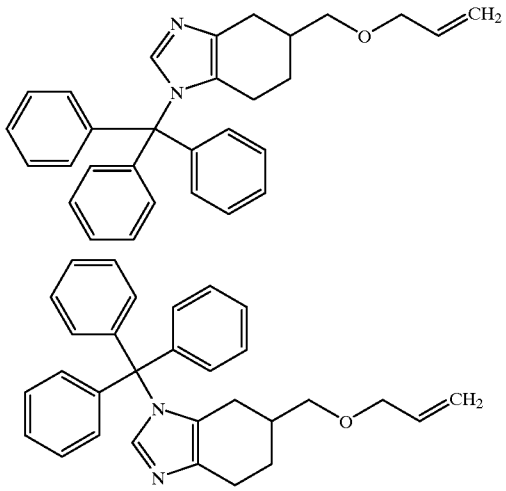

At 0° C., a 60% dispersion of sodium hydride in mineral oil (508 mg, 12.7 mmol) was added portionwise to a suspension of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (500 mg, 1.27 mmol) in THF (5 ml). After the development of hydrogen had ceased, allyl bromide (0.13 ml, 1.52 mmol) and subsequently tetrabutylammonium iodide were added. The reaction mixture was stirred for 16 hours, while it was warming up to room temperature. It was cooled to 0° C. Water (1 ml) was added carefully dropwise. A 1 N aqueous solution of sodium hydroxide (30 ml) was added. The mixture was extracted with tert-butyl methyl ether (3×30 ml). The combined organic layers were dried over magnesium sulphate. The solvent was removed. The crude product was purified by flash chromatography on silica (80 g), using ethyl acetate as eluent, to give 290 mg of a mixture of allyloxy-1-triphenylmethyl-4,5,6,7-tetrahydro-1H-benzimidazole and allyloxy-3-triphenylmethyl-4,5,6,7-tetrahydro-1H-benzimidazole.

$^1$H NMR (CDCl$_3$, 2 sets of signals): δ 1.15–1.40 (m, 2 H); 1.70 and 1.90 (both m, together 3 H); 2.35, 2.65, and 2.75 (dd, m, and dd, together 2 H), 3.05, 3.25, and 3.30 (m, dd, and dd, together 2 H); 3.80 and 3.95 (both d, together 2 H); 5.05–5.30 (m, 2 H); 5.85 (m, 1 H); 7.05–7.40 (m, 16 H).

Step 2

A solution of a mixture of allyloxy-1-triphenylmethyl-4,5,6,7-tetrahydro-1H-benzimidazole and allyloxy-3-triphenylmethyl-4,5,6,7-tetrahydro-3H-benzimidazole (290 mg, 0.73 mmol) in a mixture of glacial acetic acid (9 ml) and water (1 ml) was heated to 70° C. for 2 hours. The reaction mixture was cooled to room temperature. The solvent was removed in vacuo. The crude product was purified by flash chromatography on silica (50 g), using DCM/methanol/25% aqueous ammonia (100:10:1) as eluent, to give 107 mg of the title compound.

HPLC method C: elution at 50.76 min. $^1$H NMR (CDCl$_3$) δ 1.50 (m, 1 H); 2.05 (m, 1 H); 2.15 (m, 1 H); 2.30 (m, 1 H); 2.65 (m, 3 H); 3.40 (m, 2 H); 4.00 (m, 2 H); 5.15 (d, 1 H); 5.30 (d, 1 H); 5.95 (m, 1 H); 7.45 (s, 1 H); 8.65 (br, 1 H). MS: Calc for [M+H]$^+$: 193; Found: 193.

For biological testing, the title compound was transferred into its hydrochloride salt: The title compound (58 mg) was dissolved in ethyl acetate (2 ml). A 3.5 M solution of hydrogen chloride in ethyl acetate (1 ml) was added. The solvent was removed in vacuo. The residue was dissolved in ethyl acetate (1 ml) and heptane (3 ml). The solvent was removed. The residue was dried in vacuo.

Example 45
5-(((2-Naphthyl)methoxy)methyl)-4,5,6,7-tetrahydro-1H-benzimidazole

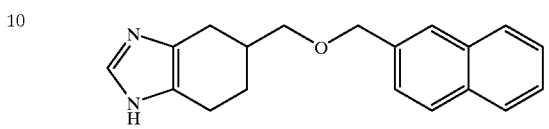

Step 1: 5-(((2-Naphthyl)methoxy)methyl)-1-triphenylmethyl-4,5,6,7-tetrahydro-1H-benzimidazole and 5-(((2-naphthyl)methoxy)methyl)-3-triphenylmethyl-4,5,6,7-tetrahydro-3H-benzimidazole

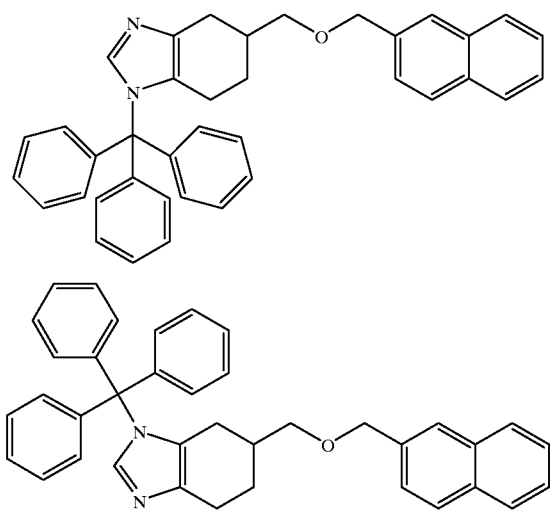

At 0° C., a 60% dispersion of sodium hydride in mineral oil (3.0 g, 76 mmol) was added to a solution of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (1.5 g, 3.8 mmol) in THF (10 ml). After the evolution of hydrogen had ceased, tetrabutylammonium iodide (70 mg, 0.19 mmol) was added. (2-Naphthyl)methyl bromide (0.92 g, 4.18 mmol) was added successively. The reaction mixture was stirred for 16 hours at room temperature. Water (100 ml) was added slowly dropwise. The reaction mixture was extracted with ethyl acetate (3×70 ml). The combined organic layers were washed with a saturated aqueous solution of sodium hydrogencarbonate and dried over magnesium sulphate. The solvent was removed in vacuo. The crude product was purified by flash chromatography on silica (90 g), using a gradient of ethyl acetate/heptane (from 50:50 to 100:0), to give 590 mg of a mixture of 5-(((2-naphthyl)methoxy)methyl)-1-triphenylmethyl-4,5,6,7-tetrahydro-1H-benzimidazole and 5-(((2-naphthyl)methoxy)methyl)-3-triphenylmethyl-4,5,6,7-tetrahydro-3H-benzimidazole.

$^1$H NMR (CDCl$_3$, 2 sets of signals): δ 1.25 and 1.45 (both m, together 1 H); 1.75 (m, 1 H); 1.90 (m, 1 H); 2.60–2.90 (m, 3 H); 3.10, 3.20, and 3.40 (all m, together 3 H); 4.50 and 4.65 (both s, together 2 H); 7.00–7.95 (m, 16 H).

Step 2

A solution of a mixture of 5-(((2-naphthyl)methoxy)methyl)-1-triphenylmethyl-4,5,6,7-tetrahydro-1H-benzimidazole and 5-(((2-naphthyl)methoxy)methyl)-3-triphenylmethyl-4,5,6,7-tetrahydro-3H-benzimidazole (590 mg, 1.1 mmol) in a mixture of glacial acetic acid (5 ml) and water (0.6 ml) was heated to 70° C. for 2 hours. The solvent was removed in vacuo. The crude product was purified by flash chromatography on silica, using DCM/methanol/25% aqueous ammonia (100:10:1) as eluent, to give 300 mg of the title compound.

HPLC method C: elution at 9.67 min. MS: Calc for [M+H]$^+$: 293; Found: 293.

Microanalysis for $C_{19}H_{20}N_2O$, $H_2O$ (292.38, 18.02):

Calc: C: 73.52%; H: 7.14%; N: 9.02%;

Found: C: 73.29%; H: 6.85%; N: 8.99%.

The title compound was transferred into its hydrochloride salt, by dissolving it in ethyl acetate (30 ml) and addition of a 3.5 M solution of hydrogen chloride in ethyl acetate (3 ml). The precipitation was collected and dried in vacuo.

$^1$H NMR (DMSO-d$_6$): δ 1.50 (m, 1 H); 2.00 (m, 1 H); 2.15 (m, 1 H); 2.30 (dd, 1 H); 2.60 (m, 2 H); 2.70 (dd, 1 H); 3.50 (d, 2 H); 4.65 (s, 2 H); 7.50 (m, 3 H); 7.85 (s, 1 H); 7.95 (m, 3 H); 8.20 (s, 1 H).

Example 46

5-(2-Chloro-5-trifluoromethylbenzyloxymethyl)-4,5,6,7-tetrahydro-1H-benzimidazole

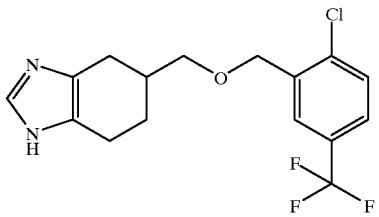

Step 1: 5-(2-Chloro-5-trifluoromethylbenzyloxymethyl)-1-triphenylmethyl-4,5,6,7-tetrahydro-1H-benzimidazole and 5-(2-chloro-5-trifluoromethylbenzyloxymethyl)-3-triphenylmethyl-4,5,6,7-tetrahydro-3H-benzimidazole

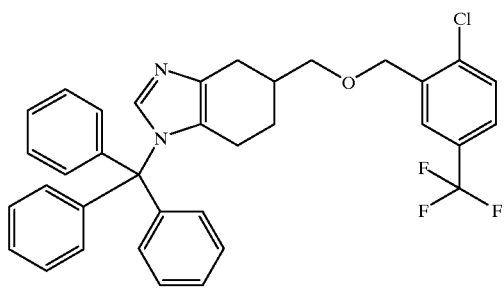

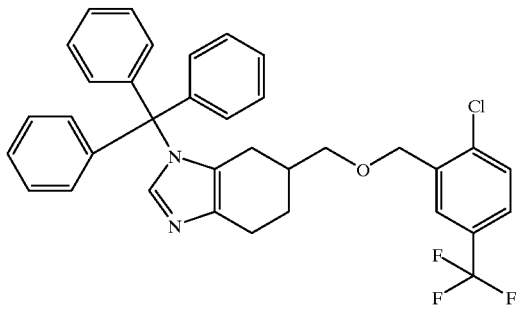

At 0° C., a 60% dispersion of sodium hydride in mineral oil (2.0 g, 50.7 mmol) was added portionwise to a solution of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (1.0 g, 2.54 mmol) in THF. The reaction mixture was stirred until the evolution of hydrogen had ceased. Tetrabutylammonium iodide (0.05 g, 0.13 mmol) and 2-chloro-5-(trifluoromethyl)benzyl bromide (0.76 g, 2.79 mmol) (purchased from Fluorochem no: 6424) were added. The reaction mixture was stirred at room temperature for 16 hours. Water (100 ml) was added very carefully dropwise. The mixture was extracted with ethyl acetate (3×60 ml). The combined organic layers were washed with a saturated aqueous solution of sodium hydrogencarbonate (100 ml) and dried over magnesium sulphate. The solvent was removed in vacuo. The crude product was purified by flash chromatography on silica (40 g), using a gradient of ethyl acetate/heptane (from 50:50 to 100:0) as eluent, to give 560 mg of a mixture of 5-(2-chloro-5-trifluoromethylbenzyloxymethyl)-1-triphenylmethyl-4,5,6,7-tetrahydro-1H-benzimidazole and 5-(2-chloro-5-trifluoromethylbenzyloxymethyl)-3-triphenylmethyl-4,5,6,7-tetrahydro-3H-benzimidazole.

$^1$H NMR (CDCl$_3$, 2 sets of signals): δ 1.20–2.10 (m, 5 H); 2.40, 2.70, and 2.80 (dd, m, and dd, together 2 H); 3.20, 3.30, 3.40, and 3.55 (all m, together 2 H); 4.40 and 4.60 (s, and AB, together 2 H); 7.15, 7.30, and 7.45 (all m, together 15 H), 7.55 and 7.70 (both s, together 1 H).

Step 2

A solution of a mixture of 5-(2-chloro-5-trifluoromethylbenzyloxymethyl)-1-triphenylmethyl-4,5,6,7-tetrahydro-1H-benzimidazole and 5-(2-chloro-5-trifluoromethylbenzyloxymethyl)-3-triphenylmethyl-4,5,6,7-tetrahydro-3H-benzimidazole in a mixture of acetic acid (5 ml) and water (0.6 ml) was heated to 90° C. for 2 hours. The reaction mixture was cooled to room temperature. The solvent was removed in vacuo. The crude product was purified by flash chromatography on silica (40 g), using a mixture of DCM/methanol/25% aqueous ammonia (100:10:1) as eluent, to give 310 mg of the title compound.

$^1$H NMR (CDCl$_3$): δ 1.60 (m, 1 H), 3.10 (m, 1 H); 2.25 (m, 1 H); 2.43 (dd, 1 H); 2.65 (m, 2 H); 2.80 (dd, 1 H); 3.60 (d, 2 H); 4–65 (s, 2 H); 6.60 (br, 1 H); 7.45 (AB, 2 H); 7.53 (s, 1 H); 7.75 (s, 1 H). HPLC method C: elution at 10.34 min. MS: Calc for [M+H]$^+$: 345; Found: 345

The title compound was transferred into its hydrochloride salt, by dissolving it in ethyl acetate (30 ml) and addition of a 3.5 M solution of hydrogen chloride in ethyl acetate (3 ml). The precipitation was collected and dried in vacuo.

Microanalysis for $C_{16}H_{16}ClF_3N_2O$, HCl (344.77, 36.46):
Calc: C: 50.41%; H: 4.49%; N: 7.35%;
Found: C: 51.09%; H: 4.61%; N: 7.30%.

Example 47
(E)-5-(3-Phenylallyloxymethyl)-4,5,6,7-tetrahydro-1H-benzimidazole

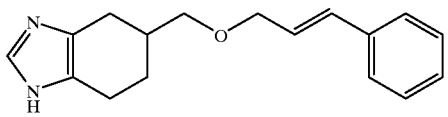

Step 1: (E)-5-(3-Phenylallyloxymethyl)-1-triphenylmethyl-4,5,6,7-tetrahydro-1H-benzimidazole and (E)-5-(3-phenylallyloxymethyl)-3-triphenylmethyl-4,5,6,7-tetrahydro-3H-benzimidazole

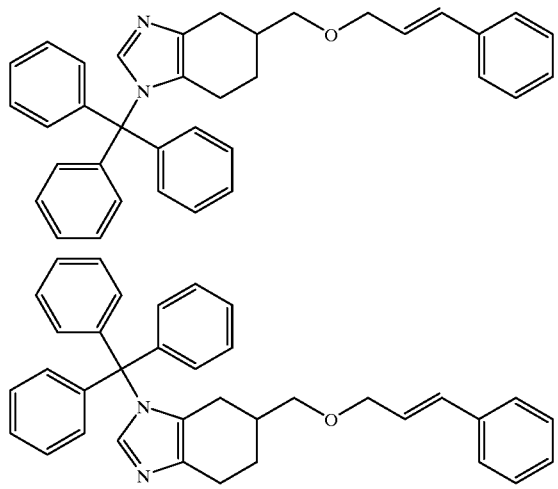

At 0° C., a 60% dispersion of sodium hydride in mineral oil (4.1 g, 101 mmol) was added to a suspension of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (2.0 g, 5.07 mmol) in THF (10 ml). After the hydrogen evolution had ceased, tetrabutylammonium iodide (100 mg, 0.25 mmol) was added. A solution of cinnamyl bromide (5.0 g, 25 mmol) in THF (5 ml) was added dropwise. The reaction mixture was stirred for 16 hours at room temperature. The reaction mixture was cooled to 0° C. Water (20 ml) was added carefully dropwise. The reaction mixture was extracted with ethyl acetate (3×60 ml). The combined organic layers were washed with a saturated aqueous solution of sodium hydrogencarbonate (100 ml) and successively dried over magnesium sulphate. The solvent was removed in vacuo. The crude product was purified by flash chromatography on silica (90 g), using a gradient of ethyl acetate/heptane (1:2 to pure ethyl acetate) as eluent, to give 501 mg of a mixture of (E)-5-(3-phenylallyloxymethyl)-1-triphenylmethyl-4,5,6,7-tetrahydro-1H-benzimidazole and (E)-5-(3-phenylallyloxymethyl)-3-triphenylmethyl-4,5,6,7-tetrahydro-3H-benzimidazole.

$^1$H NMR (CDCl$_3$, 2 sets of signals): δ 1.20–1.55 (m, 2 H); 1.75 and 1.90 (both m, together 3 H); 2.40, 2.65, and 2.80 (dd, m, and dd, together 2 H); 3.15, 3.20, and 3.45 (m, dd, and dd, together 2 H); 4.00 and 4.10 (both m, together 2 H); 6.15 and 6.25 (both m, together 1 H); 6.50 and 6.60 (both d, together 1 H); 7.00–7.50 (m, 21 H).

Step 2

A mixture of (E)-5-(3-phenylallyloxymethyl)-1-triphenylmethyl-4,5,6,7-tetrahydro-1H-benzimidazole and (E)-5-(3-phenylallyloxymethyl)-3-triphenylmethyl-4,5,6,7-tetrahydro-3H-benzimidazole (501 mg, 0.98 mmol) was dissolved in a mixture of acetic acid (5.0 ml) and water (0.6 ml). The reaction mixture was stirred for 2 hours at 90° C. The solvent was removed in vacuo. The crude product was purified by flash chromatography on silica (40 g), using DCM/methanol/25% aqueous ammonia (100:10:1) as eluent, to give 179 mg of the title compound.

$^1$H NMR (CDCl$_3$): δ 1.60 (m, 1 H); 2.10 (m, 1 H); 2.20 (m, 1 H); 2.40 (m, 1 H); 2.65 (m, 2 H); 2.80 (m, 1 H); 3.50 (m, 2 H); 4.20 (m, 2 H); 6.30 (m, 1 H); 6.65 (d, 1 H); 7.20–7.45 (m, 5 H); 7.50 (s, 1 H). HPLC method C: elution at 8.90 min. MS: Calc for [M+H]$^+$: 269; Found: 269.

80 mg of the title compound was transformed into its hydrochloride salt, by dissolving it in ethyl acetate (30 ml) and addition of a 3.5 M solution of hydrogen chloride in ethyl acetate (3 ml). The precipitation was collected and dried in vacuo.

Microanalysis for C$_{17}$H$_{20}$N$_2$O, HCl (268.36, 36.46)
Calc: C: 66.99%; H: 6.94%; N: 9.19%;
Found: C: 66.24%; H: 7.12%; N: 8.99%.

Example 48
5-((Biphenyl-4-yl)methoxymethyl)-4,5,6,7-tetrahydro-1H-benzimidazole

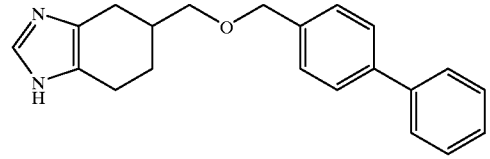

Step 1: 5-((Biphenyl-4-yl)methoxymethyl)-1-triphenylmethyl-4,5,6,7-tetrahydro-1H-benzimidazole and 5-((biphenyl-4-yl)methoxymethyl)-3-triphenylmethyl-4,5,6,7-tetrahydro-3H-benzimidazole

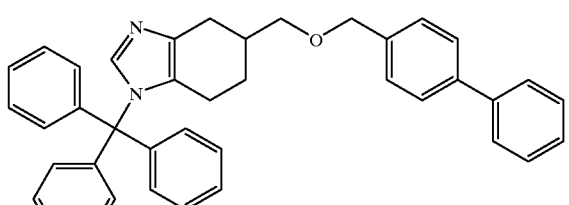

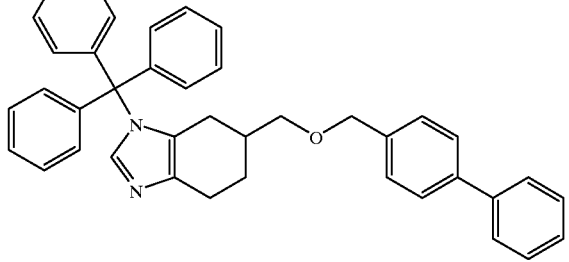

At 0° C., a 60% dispersion of sodium hydride in mineral oil (2.0 g, 51 mmol) was added portionwise to a suspension of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (1.0 g, 2.54 mmol) in THF (10 ml). After the evolution of hydrogen had ceased, tetrabutylammonium iodide (50 mg, 0.13 mmol) and subsequently 4-bromomethylbiphenyl (purchased from TCI no B1847, 690 mg, 2.79 mmol) were added. The reaction mixture was stirred for 16 hours at room temperature. It was cooled to 0° C. Water (10 ml) was added carefully dropwise. The mixture was extracted with ethyl acetate (3×60 ml). The combined organic layers were washed with a saturated aqueous solution of sodium hydrogencarbonate (100 ml) and dried over magnesium sulphate. The solvent was removed in vacuo. The crude product was purified by flash chromatography on silica (90 g), using a gradient of ethyl acetate/heptane (from 1:2 to 1.0) as eluent, to give 440 mg of a mixture of 5-((biphenyl-4-yl)methoxymethyl)-1-triphenylmethyl-4,5,6,7-tetrahydro-1H-benzimidazole and 5-((biphenyl-4-yl)methoxymethyl)-3-triphenylmethyl-4,5,6,7-tetrahydro-3H-benzimidazole.

$^1$H NMR (CDCl$_3$, 2 sets of signals): δ 1.20–1.55 (m, 2 H); 1.60–2.00 (m, 3 H); 2.40, 2.65, and 2.75 (all m, together 2 H); 3.15, 3.35, and 3,45 (m, dd, and dd, together 2 H); 4.38 and 4.50 (both s, together 2 H); 7.50–7.65 (m, 25 H).

Step 2

A solution of a mixture of 5-((biphenyl-4-yl)methoxymethyl)-1-triphenylmethyl-4,5,6,7-tetrahydro-1H-benzimidazole and 5-((biphenyl-4-yl)methoxymethyl)-3-triphenylmethyl-4,5,6,7-tetrahydro-3H-benzimidazole (440 mg, 0.78 mmol) in a mixture of acetic acid (5 ml) and water (0.6 ml) was heated to 90° C. for 2.25 hours. The solvent was removed in vacuo. The crude product was purified by flash chromatography on silica (40 g), using DCM/methanol/25% aqueous ammonia (100:10:1) as eluent, to give 220 mg of the title compound.

$^1$H NMR (CDCl$_3$) δ 1.55 (m, 1 H); 2.10 (m, 1 H); 2.25 (m, 1 H); 2.40 (m, 1 H); 2.65 (m, 2 H); 2.80 (dd, 1 H); 3.50 (m, 2 H); 4.60 (s, 2 H); 5.40 (br, 1 H); 7.30–7.65 (m, 10 H). HPLC method C: elution at 10.56 min. MS: Calc for [M+H]$^+$: 319; Found: 319.

Microanalysis for C$_{21}$H$_{22}$N$_2$O, ½ H$_2$O (318.42, ½ 18.02):
Calc: C: 77.03%; H: 7.08%; N: 8.56%;
Found: C: 77.47%; H: 7.34%; N: 8.56%.

The title compound was transformed into its hydrochloride salt, by dissolving it in ethyl acetate (30 ml) and addition of a 3.5 M solution of hydrogen chloride in ethyl acetate (3 ml). The precipitation was collected and dried in vacuo.

Example 49
5-(3-Phenylpropoxymethyl)-4,5,6,7-tetrahydro-1H-benzimidazole

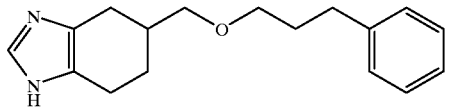

To a solution of (E)-5-(3-phenylallyloxymethyl)-4,5,6,7-tetrahydro-1H-benzimidazole (90 mg) in ethanol (40 ml) palladium on coal (50% wet, 1.0 g) was added. The reaction mixture was kept under a hydrogen atmosphere at room pressure for 4 hours. The catalyst was removed by filtration through a plug of celite. The solvent was removed in vacuo. The crude product was purified by subjecting it to a Sep-Pack® chromatography, using a gradient of water/acetonitrile with 0.1% TFA (from 10% acetonitrile to 45% acetonitril). Subsequent lyophilization of the pure fractions in the presence of 0.1 N hydrochloric acid gave 15 mg of the hydrochloride salt of the title compound.

$^1$H NMR (crude product, free base, CDCl$_3$): δ 1.55 (m,1 H); 1.90 (m, 2 H); 2.10 (m, 2 H); 2.40 (m, 1 H); 2.70 (m, 5 H); 3.40 (m, 4 H); 7.10–7.40 (m, 6 H). HPLC method C: elution at 9.74 min. MS: Calc for [M+H]$^+$: 271; Found: 271.

Example 50
5-(2-Chloro-3-(trifluoromethyl)benzyloxymethyl)-4,5,6,7-tetrahydro-1H-benzimidazole

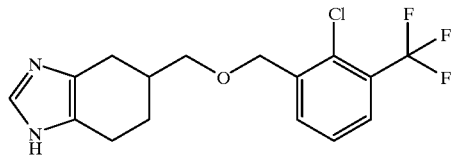

Step 1: (2-Chloro-3-(trifluoromethyl)phenyl)methanol

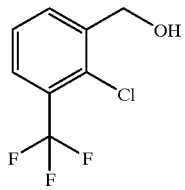

Sodium borohydride (2.54 g, 67.1 mmol) was added to a solution of 2-chloro-3-(trifluoromethyl)benzaldehyde (purchased at Interchim, cat. # 21117, 10.0 g, 47.9 mmol) in a mixture of DCM (40 ml) and 2-propanol (20 ml), while the mixture was cooled with a water bath. The reaction mixture was stirred for 16 hours at room temperature. At 0° C., a 10% aqueous solution of sodium hydrogensulphate (20 ml) was added dropwise. The reaction mixture was diluted with DCM (100 ml) and water (100 ml). The phases were separated. The organic layer was washed with a saturated aqueous solution of sodium hydrogencarbonate (100 ml) and dried over magnesium sulphate. The solvent was removed in vacuo to give 9.37 g of crude (2-chloro-3-(trifluoromethyl)phenyl)methanol, which was used for the next step without further purification.

$^1$H NMR (CDCl$_3$): δ 2.05 (br, 1 H); 4.90 (s, 2 H); 7.45 (t, 1 H); 7.70 (d, 1 H); 7.80 (d, 1 H). HPLC method C: elution at 11.12 min.

Step 2: 1-(Bromomethyl)-2-chloro-3-(trifluoromethyl)benzene

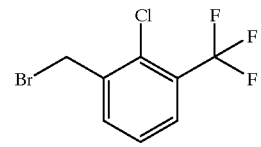

Phosphorus tribromide (11.75 ml, 125 mmol) was added to a solution of crude (2-chloro-3-(trifluoromethyl)phenyl)methanol (9.37 g, 44.5 mmol) in dioxane (200 ml). The reaction mixture was stirred for 1 hour. Another portion of phosphorus tribromide (11.75 ml, 125 mmol) was added. The reaction mixture was stirred for 16 hours at room temperature. It was diluted with ethyl acetate (200 ml). A 10% aqueous solution of sodium hydrogensulphate (200 ml) was added, while cooling with a water bath. The phases were separated. The organic phase was washed with a 10% aqueous solution of sodium hydrogensulphate (100 ml). The combined aqueous layers were extracted with ethyl acetate (100 ml). The combined organic layers were washed with a saturated aqueous solution of sodium hydrogencarbonate (100 ml) and dried over magnesium sulphate. The solvent was removed in vacuo. The crude product was purified by flash chromatography on silica (150 g), using ethyl acetate/heptane (1:3) as eluent, to give 6.94 g of 1-(bromomethyl)-2-chloro-3-(trifluoromethyl)benzene.

$^1$H NMR (CDCl$_3$): δ 4.65 (s, 2 H); 7.40 (t, 1 H); 7.70 (m, 2 H).

Step 3: 5-(2-Chloro-3-(trifluoromethyl)benzyloxymethyl)-1-triphenylmethyl-4,5,6,7-tetrahydro-1H-benzimidazole and 5-(2-chloro-3-(trifluoromethyl)benzyloxymethyl)-3-triphenylmethyl-4,5,6,7-tetrahydro-3H-benzimidazole

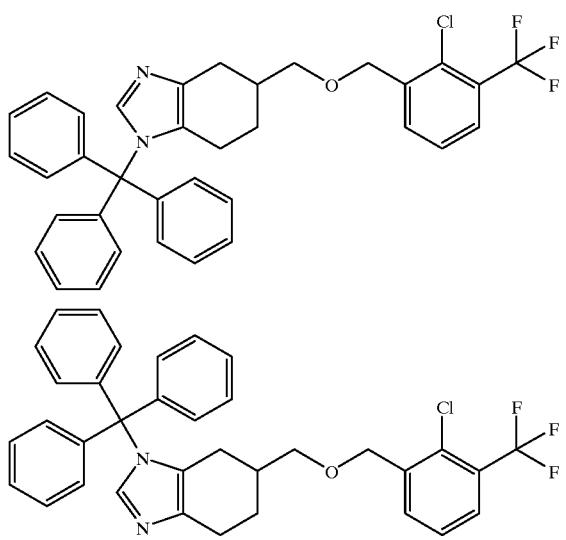

At 0° C., a 60% dispersion in mineral oil of sodium hydride (500 mg, 12.6 mmol) was added to a suspension of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (250 mg, 0.63 mmol) in THF (4 ml). After the evolution of hydrogen had ceased, A solution of 1-(bromomethyl)-2-chloro-3-(trifluoromethyl)benzene (190 mg, 0.69 mmol) in THF (2 ml) was added. Tetrabutylammonium iodide (12 mg, 0.03 mmol) was added. The reaction mixture was stirred for 56 hours, while the reaction mixture was warming up to room temperature. It was diluted with THF (10 ml). Water (10 ml) was added carefully dropwise, while the reaction mixture was cooled with a water bath. It was diluted with ethyl acetate (20 ml) and washed with a 10% aqueous solution of sodium hydrogensulphate (20 ml). The aqueous solution was extracted with ethyl acetate (20 ml). The combined organic layers were washed with a saturated aqueous solution of sodium hydrogencarbonate (100 ml) and dried over magnesium sulphate. The solvent was removed in vacuo. The crude product was purified by flash chromatography on silica (90 g), using first pure ethyl acetate and successively DCM/methanol/25% aqueous ammonia (100:10:1) as eluent, to give 48 mg of a mixture of 5-(2-chloro-3-(trifluoromethyl)benzyloxymethyl)-1-triphenylmethyl-4,5,6,7-tetrahydro-1H-benzimidazole and 5-(2-chloro-3-(trifluoromethyl)benzyloxymethyl)-3-triphenylmethyl-4,5,6,7-tetrahydro-3H-benzimidazole.

$^1$H NMR (CDCl$_3$, 2 sets of signals): δ 1.40 (m, 2 H); 1.65–2.10 (m, 3 H); 2.45, 2.70, and 3.85 (dd, m, and dd, together 2 H); 3.20, 3.30, 3.45, and 3.55 (all dd, together 2 H); 4.45 and 4.60 (both s, together 2 H); 7.00–7.40, 7.45, 7.60, and 7.70 (m, dd, dd, and dd, together 19 H).

Step 4

A solution of a mixture of 5-(2-chloro-3-(trifluoromethyl)benzyloxymethyl)-1-triphenylmethyl-4,5,6,7-tetrahydro-1H-benzimidazole and 5-(2-chloro-3-(trifluoromethyl)benzyloxymethyl)-3-triphenylmethyl-4,5,6,7-tetrahydro-3H-benzimidazole in a mixture of acetic acid (9 ml) and water (1 ml) was heated to 70° C. for 2 hour. The reaction mixture was cooled to room temperature. The solvent was removed in vacuo. The crude product was purified by flash chromatography on silica (40 g), using a mixture of DCM/methanol/25% aqueous ammonia (100:10:1) as eluent, to give 25 mg of the title compound.

$^1$H NMR (CDCl$_3$): δ 1.60 (m, 1 H); 2.10 (m, 1 H); 2.25 (m, 1 H); 2.45 (dd, 1 H); 2.65 (m, 2 H); 2.80 (dd, 1 H); 3.60 (d, 2 H); 4.65 (s, 2 H); 6.10 (br, 1 H); 7.40 (t, 1 H); 7.50 (s, 1 H); 7.65 (d, 2 H); 7.75 (d, 1 H). HPLC method C: elution at 10.42 min. MS: Calc for [M+H]$^+$: 345; Found: 345.

For biological testing, the title compound was transformed into its hydrochloride salt, by dissolving it in ethyl acetate (10 ml) and addition of a 3.5 M solution of hydrogen chloride in ethyl acetate (1.5 ml, 5.25 mmol). The solvent was removed in vacuo.

Microanalysis for $C_{16}H_{16}ClF_3N_2O$, HCl (344.77, 36.46):
Calc: C: 50.41%; H: 4.49%; N: 7.35%;
Found: C: 50.62%; H: 4.51%; N: 7.18%.

Example 51
3-(((4,5,6,7-Tetrahydro-1H-benzimidazol-5-yl)methoxy)methyl)benzonitrile

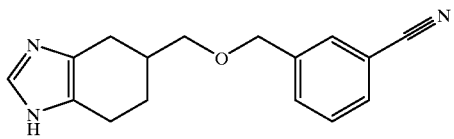

Step 1: 3-(((1-Triphenylmethyl-4,5,6,7-tetrahydro-1H-benzimidazol-5-yl)methoxy)methyl)benzonitrile and 3-(((3-triphenylmethyl-4,5,6,7-tetrahydro-3H-benzimidazol-5-yl)methoxy)methyl)benzonitrile

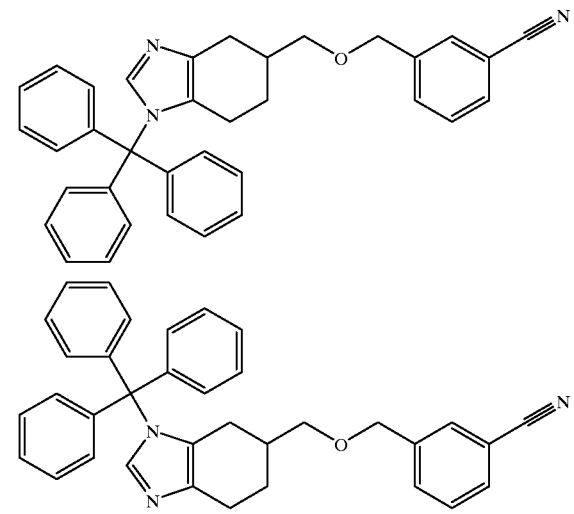

At 0° C., a 60% suspension of sodium hydride in mineral oil (3.0 g, 76 mmol) was added to a suspension of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (1.50 g, 3.80 mmol) in THF (10 ml). After the hydrogen evolution had ceased, tetrabutylammonium iodide (70 mg, 0.19 mmol) and 3-(bromomethyl)benzonitrile (0.82 g, 4.18 mmol) were added successively. The reaction mixture was stirred for 16 hours at room temperature. Water (100 ml) was added carefully. The mixture was extracted with ethyl acetate (3×70 ml). The combined organic layers were washed with a saturated aqueous solution of sodium hydrogencarbonate (100 ml) and dried over magnesium sulphate. The solvent was removed in vacuo. The crude product was purified by flash chromatography on silica (90 g), using a gradient of ethyl acetate/heptane (from 1:1 to 1:0) as eluent, to give 0.18 g of a mixture of 3-(((1-triphenylmethyl-4,5,6,7-tetrahydro-1H-benzimidazol-5-yl)methoxy)methyl)benzonitrile and 3-(((3-triphenylmethyl-4,5,6,7-tetrahydro-3H-benzimidazol-5-yl)methoxy)methyl)benzonitrile.

$^1$H NMR (CDCl$_3$, 2 sets of signals): δ 1.20–2.10 (m 5 H); 2.40, 2.70, and 2.80 (dd, m, and dd, together 2 H); 3.15, 3.25, 3.35, and 3.50 (all dd, together 2 H); 4.35 and 4.50 (both s, together 2 H); 7.00–7.65 (m, 16 H).

Step 2

A solution of a mixture of 3-(((1-triphenylmethyl-4,5,6,7-tetrahydro-1H-benzimidazol-5-yl)methoxy)methyl)benzonitrile and 3-(((3-triphenylmethyl-4,5,6,7-tetrahydro-3H-benzimidazol-5-yl)methoxy)methyl)benzonitrile (0.18 g, 0.34 mmol) in acetic acid (5 ml) and water (0.6 ml) was heated to 90° C. for 2 hours. The solvent was removed in vacuo. The crude product was purified by flash chromatography on silica (40 g), using DCM/methanol/~25% aqueous ammonia (100:10:1) as eluent, to give 71 mg of the title compound.

$^1$H NMR (CDCl$_3$): δ 1.60 (m, 1 H); 2.10 (m, 1 H); 2.25 (m, 1 H); 2.45 (dd, 1 H); 2.70 (m, 2 H); 2.80 (dd, 1 H); 3.50 (m, 2 H); 4.60 (s, 2 H); 4.80 (br, 1 H); 7.30 (s, 1 H); 7.50 (m, 1 H); 7.55 (m, 2 H); 7.65 (s, 1 H). HPLC method C: elution at 7.48 min. MS: Calc for [M+H]$^+$: 268; Found: 268.

For biological testing, the title compound was transformed into its hydrochloride salt, by dissolving it in ethyl acetate (10 ml) and addition of a 3.5 M solution of hydrogen chloride in ethyl acetate (1.5 ml, 5.25 mmol). The solvent was removed in vacuo. The residue was crystallized form acetone.

Example 52
5-(4-Phenylbutoxymethyl)-4,5,6,7-tetrahydro-1H-benzimidazole

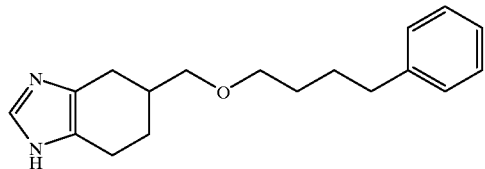

Step 1: 4-(Bromobutyl)benzene

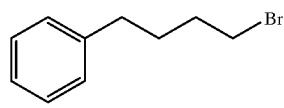

Phosphorus tribromide (17.6 ml, 186 mmol) was added dropwise to a solution of 4-phenyl-1-butanol (10.0 g, 66.6 mmol) in dioxane (200 ml). The reaction mixture was stirred for 1 hour at room temperature. Another portion of phosphorus tribromide (17.6 ml, 186 mmol) was added dropwise. The reaction mixture was stirred for 16 hours at room temperature. It was cooled to 0° C. Water (130 ml) was added dropwise. The reaction mixture was stirred for 30 min at room temperature. It was diluted with ethyl acetate (200 ml) and washed with 1 N hydrochloric acid (200 ml). The aqueous phase was extracted with ethyl acetate (2×100 ml). The combined organic layers were washed with a saturated aqueous solution of sodium hydrogencarbonate (200 ml) and dried over magnesium sulphate. The solvent was removed in vacuo. The crude product was purified by flash chromatography on silica (300 g), using ethyl acetate/heptane 1:3 as eluent, to give 8.54 g of (4-bromobutyl)benzene.

$^1$H NMR (CDCl$_3$): δ 1.75 (tt, 2 H); 1.90 (tt, 2 H); 2.65 (t, 2 H); 3.40 (tt, 2 H); 7.10 (m, 3 H); 7.25 (m, 2 H).

Step 2: 5-(4-Phenylbutoxymethyl)-1-triphenylmethyl-4,5,6,7-tetrahydro-1H-benzimidazole and 5-(4-phenylbutoxymethyl)-3-triphenylmethyl-4,5,6,7-tetrahydro-3H-benzimidazole

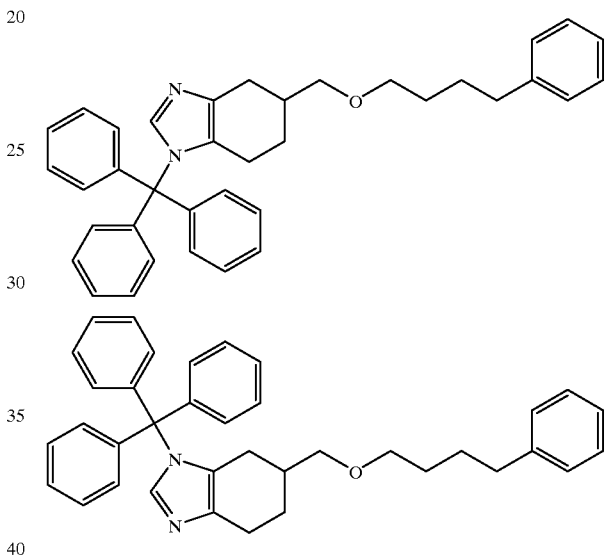

At 0° C., a 60% dispersion of sodium hydride (0.30 g, 6.34 mmol) was added to a suspension of a mixture of of (1-(triphenylmethyl))-4,5,6,7-tetrahydro-1H-benzimidazol-5-yl)methanol and (3-(triphenylmethyl)-4,5,6,7-tetrahydro-3H-benzimidazol-5-yl)methanol (0.50 g, 1.23 mmol) in N,N-dimethylformamide. The reaction mixture was stirred for 20 min at room temperature. Tetrabutylammonium iodide (20 mg, 0.06 mmol) and (4-bromobutyl)benzene (0.80 g, 3.80 mmol) were added successively. The reaction mixture was stirred for 2 days at 60° C. It was cooled to room temperature. Water (50 ml) was added dropwise. The reaction mixture was extracted with ethyl acetate (3×70 ml). The combined organic layers were washed with a saturated aqueous solution of sodium hydrogencarbonate (100 ml) and dried over magnesium sulphate. The solvent was removed in vacuo. The crude product was purified by flash chromatography on silica (40 g), using a gradient of ethyl acetate/heptane (from 1:1 to 4:1) as eluent, to give 0.52 g of a mixture of 5-(4-phenylbutoxymethyl)-1-triphenylmethyl-4,5,6,7-tetrahydro-1H-benzimidazole and 5-(4-phenylbutoxymethyl)-3-triphenylmethyl-4,5,6,7-tetrahydro-3H-benzimidazole.

$^1$H NMR (CDCl$_3$, 2 sets of signals): δ 11.05–2.05 (m, 9 H); 2.35, 2.60, 2.75 (dd, m, and dd, together 4 H); 3.05, 3.20, and 3.40 (all m, together 4 H); 7.10 (m, 8 H); 7.25 (m, 13 H).

Step 3

A mixture of 5-(4-phenylbutoxymethyl)-1-triphenylmethyl-4,5,6,7-tetrahydro-1H-benzimidazole and 5-(4-phenylbutoxymethyl)-3-triphenylmethyl-4,5,6,7-tetrahydro-3H-benzimidazole (0.50 g, 0.95 mmol) was dissolved in a mixture of acetic acid (5 ml) and water (0.6 ml). The reaction mixture was heated to 90° C. for 2 hours. The solvent was removed in vacuo. The crude product was purified by flash chromatography on silica (40 g), using DCM/methanol/25% aqueous ammonia (100:10:1) as eluent, to give 0.27 g of the title compound.

$^1$H NMR (CDCl$_3$) δ 1.50 (m,1 H); 1.65 (m, 4 H); 2.00 (m, 1 H); 2.15 (m, 1 H); 2.30 (dd, 1 H); 2.65 (m, 4 H); 2.75 (dd, 1 H); 3.40 (m, 2 H); 3.45 (m, 2 H); 4.90 (br, 1 H); 7.20 (m, 3 H); 7.25 (m, 2 H); 7.45 (s, 1 H). HPLC method C: elution at 9.50 min. MS: Calc for [M+H]$^+$:285; Found: 285.

For biological testing, the title compound was transformed into its hydrochloride salt, by dissolving it in ethyl acetate (10 ml) and addition of a 3.5 M solution of hydrogen chloride in ethyl acetate (1.5 ml, 5.25 mmol). The solvent was removed in vacuo. The residue was dissolved in acetone (5 ml). The solvent was removed in vacuo.

Microanalysis for C$_{18}$H$_{24}$N$_2$O, HCl (284.40, 36.46):

Calc: C: 67.38%; H: 7.85%; N: 8.73%;

Found: C: 66.86%; H: 8.08%; N: 8.59%.

Example 53

5-[(2-(2,4-Dichlorophenoxy)benzyloxy)methyl]-4,5,6,7-tetrahydro-1H-benzimidazole

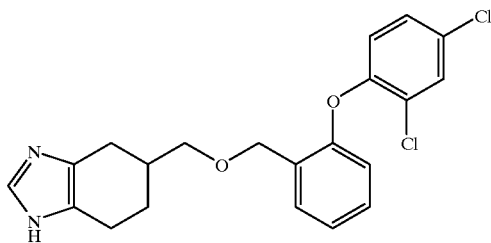

Step 1: 2-(2,4-Dichlorophenoxy)benzaldehyde

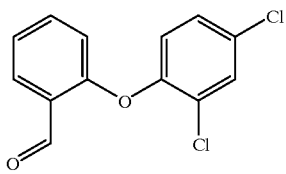

At 0° C., a 1.2 M solution of diisobutylaluminum hydride in toluene (12.3 ml, 14.8 mmol) was added dropwise to a solution of 2-(2,4-dichlorophenoxy)benzonitrile (3.0 g, 11.3 mmol) in THF (30 ml). The reaction mixture was warmed to room temperature and stirred for 16 hours. It was cooled to 0° C. Water (10 ml) was added dropwise. It was warmed to room temperature. The solid was removed by filtration through a plug of celite. The solvent was removed from the filtrate in vacuo. The crude product was purified by flash chromatography on silica (130 g), using ethyl acetate/heptane 1:3 as eluent, to give 800 mg of 2-(2,4-dichlorophenoxy)benzaldehyde.

$^1$H NMR (CDCl$_3$): δ 6.65–7.75 (m, 6 H); 7.95 (d, 1 H); 10.55 (s, 1 H).

Step 2: 1-[2-(2,4-Dichlorophenoxy)phenyl]methanol

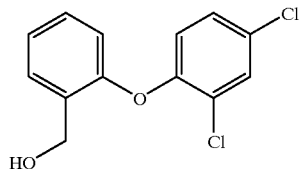

Sodium borohydride (119 mg, 3.15 mmol) was added to a solution of 2-(2,4-dichlorophenoxy)benzaldehyde (600 mg, 2.25 mmol) in isopropanol (10 ml) and DCM (20 ml). The reaction mixture was stirred for 2 hours at room temperature. A 10% aqueous solution of sodium hydrogensulphate (200 ml) was added dropwise. Ethyl acetate (300 ml) was added successively. The phases were separated. The aqueous phase was extracted with ethyl acetate (100 ml). The combined organic layers were washed with a saturated aqueous solution of sodium hydrogencarbonate (200 ml) and dried over magnesium sulphate. The solvent was removed in vacuo. The crude product was purified by flash chromatography on silica (100 g), using ethyl acetate/heptane 1:3 as eluent, to give 440 mg of 1-[2-(2,4-dichlorophenoxy) phenyl]methanol.

$^1$H NMR (CDCl$_3$): δ 2.05 (t, 1 H); 4.80 (d, 2 H); 6.75 (d, 1 H); 6.90 (d, 1 H); 7.20 (m, 3 H); 7.50 (m, 2 H).

Step 3: 2-(2,4-Dichlorophenoxy)benzyl bromide

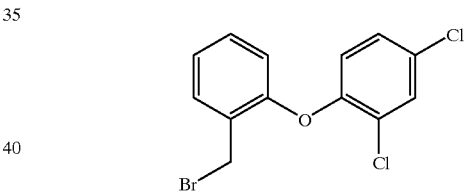

Phosphorus(III) tribromide (0.41 ml, 4.37 mmol) was added to a solution of 1-[2-(2,4-dichlorophenoxy)phenyl] methanol (420 mg, 1.56 mmol) in dioxane (10 ml). The reaction mixture was stirred for 1 hour at room temperature. Another portion of phosphorus(III) tribromide (0.41 ml, 4.37 mmol) was added. The reaction mixture was stirred for 16 hours at room temperature. It was cooled to 0° C. Water (5 ml) was added dropwise. The reaction mixture was warmed to room temperature and diluted with ethyl acetate (400 ml). It was washed with a 10% aqueous solution of sodium hydrogensulphate. The aqueous phase was extracted with ethyl acetate (50 ml). The combined organic layers were washed with a saturated aqueous solution of sodium hydrogencarbonate (200 ml) and dried over magnesium sulphate. The solvent was removed in vacuo. The crude product was purified by flash chromatography on silica (100 g), using ethyl acetate/heptane 1:3 as eluent, to give 297 mg of 2-(2,4-dichlorophenoxy)benzyl bromide.

$^1$H NMR (CDCl$_3$) δ 4.60 (s, 2 H); 6.68 (d, 1 H); 6.95 (d, 1 H); 7.08 (t, 1 H); 7.20 (m, 2 H); 7.45 (m, 2 H).

Step 4: 5-[2-(2,4-Dichlorophenoxy)benzyloxymethyl]-1-triphenylmethyl-4,5,6,7-tetrahydro-1H-benzimidazole and 5-[2-(2,4-dichlorophenoxy)benzyloxymethyl]-3-triphenylmethyl-4,5,6,7-tetrahydro-3H-benzimidazole

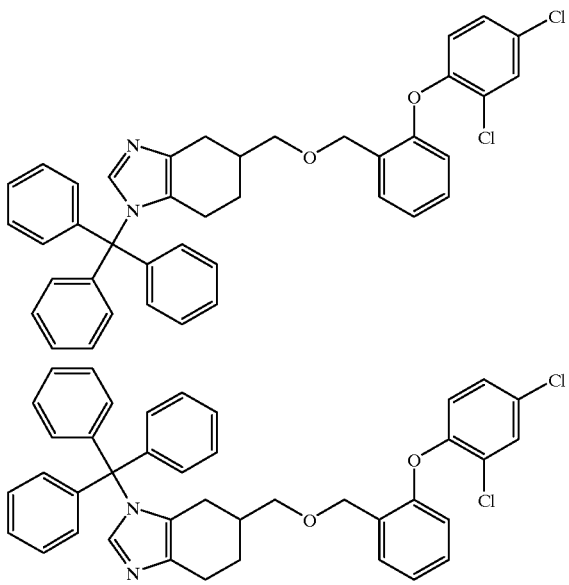

At 0° C., a 60% suspension of sodium hydride in mineral oil (704 mg, 17.6 mmol) was added portionwise to a suspension of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (347 mg, 0.88 mmol) in THF (2 ml). After the gas evolution had ceased, a solution of 2-(2,4-dichlorophenoxy)benzyl bromide (320 mg, 0.97 mmol) in THF (2 ml) and subsequently tetrabutylammonium iodide (16 mg, 0.04 mmol) were added. The reaction mixture was stirred for 16 hours, while it was warming up to room temperature. It was diluted with THF (5 ml) and cooled to 0° C. Water (3 ml) was added dropwise. Tert-butyl methyl ether (50 ml) and a 1 N aqueous solution of sodium hydroxide were added. The phases were separated. The aqueous phase was extracted with tert-butyl methyl ether (50 ml). The combined organic layers were dried over magnesium sulphate. The solvent was removed in vacuo. The crude product was purified by flash chromatography on silica, using ethyl acetate/heptane 1:1 followed by pure ethyl acetate as eluent, to give 319 mg of a mixture of 5-[2-(2,4-dichlorophenoxy)benzyloxymethyl]-1-triphenylmethyl-4,5,6,7-tetrahydro-1H-benzimidazole and 5-[2-(2,4-dichlorophenoxy)benzyloxymethyl]-3-triphenylmethyl-4,5,6,7-tetrahydro-3H-benzimidazole.

$^1$H NMR (CDCl$_3$, 2 sets of signals): δ 1.10–2.00 (m, 5 H); 2.35, 2.65, and 2.75 (dd, m, and dd, together 2 H); 3.15, 3.35, and 3.55 (ABX, dd, and dd, together 2 H); 4.40 and 4.55 (both s, together 2 H); 6.75 (m, 2 H); 7.05–7.55 (m, 22 H).

Step 5

A soution of a mixture of 5-[2-(2,4-dichlorophenoxy) benzyloxymethyl]-1-triphenylmethyl-4,5,6,7-tetrahydro-1H-benzimidazole and 5-[2-(2,4-dichlorophenoxy) benzyloxymethyl]-3-triphenylmethyl-4,5,6,7-tetrahydro-3H-benzimidazole (356 mg, 0.55 mmol) in a mixture of glacial acetic acid (9 ml) and water (1 ml) was heated to 70° C. for 2 hours. The reaction mixture was cooled to room temperature. The solvent was removed in vacuo. The crude product was purified by flash chromatography on silica (80 g), using DCM/methanol/–25% aqueous ammonia as eluent, to give 175 mg of the title compound. HPLC method C: elution at 11.42 min.

$^1$H NMR (CDCl$_3$) δ 1.50 (m, 1 H); 2.00 (m, 1 H); 2.15 (m, 1 H); 2.30 (dd, 1 H); 2.55 (m, 2 H); 2.70 (dd, 1 H); 3.50 (m, 2 H); 4.60 (s,1 H); 6.75 (d, 2 H); 7.15 (m, 2 H); 7.25 (dd, 1 H); 7.45 (m, 2 H); 7.55 (d, 1 H); 7.75 (br, 1 H). MS: Calc for [M+H]$^+$: 403; Found: 403.

For biological testing, the title compound was transferred into its hydrochloride salt by dissolving it in ethyl acetate (20 ml) and addition of a 3.8 M solution of hydrogen chloride in ethyl acetate (5 ml). The solvent was removed in vacuo. The crystals were dried in vacuo.

Microanalysis for C$_{21}$H$_{20}$Cl$_2$N$_2$O$_2$, HCl (403.31, 26.46):
Calc: C: 57.36%; H: 4.81%; N: 6.37%;
Found: C: 57.65%; H: 4.78%; N: 6.23%.

Example 54

5-[2-(4-Fluorobenzyl)benzyloxymethyl]-4,5,6,7-tetrahydro-1H-benzimidazole

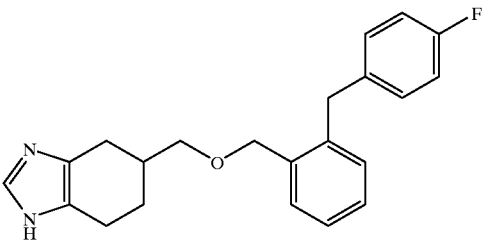

Step 1: 2-(4-Fluorobenzyl)benzoic Acid

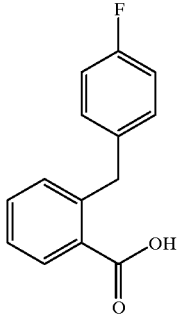

At 0° C., chlorotrimethylsilane (20.0 ml, 0.14 mol) was added dropwise to a solution of 2-(4-fluorobenzoyl)benzoic acid (purchased at Aldrich, 35 g, 0.14 mol) and triethylamine (22.0 ml, 0.15 mol) in THF (500 ml). The reaction mixture was stirred for 15 min. The solvent was removed. The residue was dissolved in DCM (400 ml). Triethylsilane (76.4 ml, 0.44 mol) was added. At 0° C., a 1 N solution of titanium(IV) chloride in DCM (430 ml, 0.43 mol) was added dropwise over a period of 1 h. The reaction mixture was stirred for 16 hours at room temperature. It was added to ice water (2000 ml). The phases were separated. The aqueous phase was extracted with DCM (400 ml). The combined organic layers were extracted with a saturated aqueous solution of sodium hydrogencarbonate (3×400 ml). The aqueous sodium hydrogencarbonate phase was acidified with 1 N hydrochloric acid to pH 2. The precipitation was isolated by filtration and dissolved in ethyl acetate (300 ml). The ethyl acetate solution was dried over magnesium sulphate. The solvent was removed in vacuo to give 19.79 g of a 1:1 mixture of 2-(4-fluorobenzyl)benzoic acid and the starting material 2-(4-fluorobenzoyl)benzoic acid, which was used without further purification for the next step.

¹H NMR (CDCl₃): δ 4.40 (s, 2 H); 7.85–8.20 (m, 8 H).

Step 2: [2-(4-Fluorobenzyl)phenyl]methanol

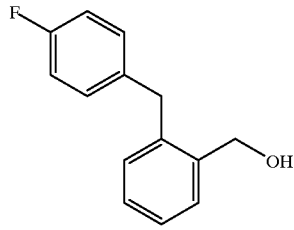

A 1 M solution of lithium aluminum hydride in THF (258 ml, 258 mmol) was added dropwise to a solution of the mixture of 2-(4-fluorobenzyl)benzoic acid and the starting material 2-(4-fluorobenzoyl)benzoic acid, which was isolated in step 1, in THF (200 ml). The reaction mixture was heated to reflux for 2 hours. It was cooled to 0° C. Carefully, methanol (100 ml) and water (50 ml) were added successively. A 10% aqueous solution of sodium hydrogensulphate (500 ml) and a 1 N solution of sodium chloride in water were added. The phases were separated. The aqueous phase was extracted with ethyl acetate (2×300 ml). The combined organic layers were washed with a saturated aqueous solution of sodium hydrogencarbonate (600 ml) and dried over magnesium sulphate. The solvent was removed in vacuo. 5.23 g of [2-(4-fluorobenzyl)phenyl]methanol were isolated by flash chromatography on silica (200 g), using ethyl acetate/heptane 1:1 as eluent.

¹H NMR (CDCl₃): δ 1.75 (br, 1 H); 4.05 (s, 2 H); 4.60 (s, 2 H); 6.95 (m, 2 H); 7.05 (m, 2 H); 7.10 (m, 1 H); 7.25 (m, 2 H); 7.35 (m, 1 H).

Step 3: 2-(4-Fluorobenzyl)benzyl Bromide

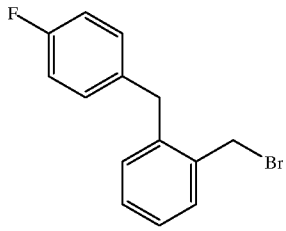

Phosphorus tribromide (6.4 ml, 67.3 mmol) was added dropwise to a solution of [2-(4-fluorobenzyl)phenyl] methanol (5.2 g, 24.05 mmol) in dioxane (125 ml). The reaction mixture was stirred for 1 hour at room temperature. Another portion of phosphorus tribromide (6.4 ml, 67.3 mmol) was added. The reaction mixture was stirred for 16 hours at room temperature. Water (60 ml) was added at 0° C. The reaction mixture was stirred for 30 min. Ethyl acetate (100 ml) was added. The phases were separated. The aqueous phase was washed with 1 N hydrochloric acid (100 ml). The combined aqueous phases were extracted with ethyl acetate (3×60 ml). The combined organic layers were washed with a saturated aqueous solution of sodium hydrogencarbonate (100 ml) and dried over magnesium sulphate. The solvent was removed in vacuo. The crude product was purified by flash chromatography on silica (90 g), using ethyl acetate/heptane 1:3 as eluent, to give 5.96 g of 2-(4-fluorobenzyl)benzyl bromide.

¹H NMR (CDCl₃): δ 4.10 (s, 2 H); 4.45 (s, 2 H); 6.95 (t, 2 H); 7.10 (m, 3 H); 7.25 (m, 2 H); 7.35 (m, 1 H).

Step 4: 5-[2-(4-Fluorobenzyl)benzyloxymethyl]-1-triphenylmethyl-4,5,6,7-tetrahydro-1H-benzimidazole and 5-[2-(4-fluorobenzyl)benzyloxymethyl]-3-triphenylmethyl-4,5,6,7-tetrahydro-3H-benzimidazole

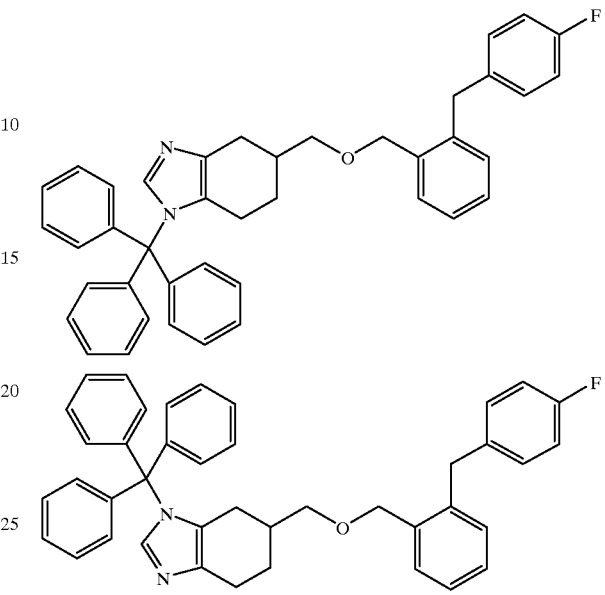

A 60% dispersion of sodium hydride in mineral oil (2.6 g, 65.9 mmol) was added protionwise to a suspension of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (1.3 g, 3.3 mmol) in THF (10 ml). After the gas evolution had ceased, tetrabutylammonium iodide (0.1 g, 0.18 mmol) and a solution of 2-(4-fluorobenzyl)benzyl bromide (1.0 g, 3.6 mmol) were added successively. The reaction mixture was stirred for 16 hours at room temperature. Water (100 ml) was added carefully to the reaction mixture. It was extracted with ethyl acetate (3×60 ml). The combined organic layers were washed with a saturated aqueous solution of sodium hydrogencarbonate (100 ml) and dried over magnesium sulphate. The solvent was removed in vacuo. The crude product was purified by flash chromatography on silica (90 g), using ethyl acetate/heptane (first 1:1, then 1:0) as eluent, to give 0.62 g of a mixture of 5-[2-(4-fluorobenzyl) benzyloxymethyl]1-triphenylmethyl-4,5,6,7-tetrahydro-1H-benzimidazole 5-[2-(4-fluorobenzyl)benzyloxymethyl]-3-triphenylmethyl-4,5,6,7-tetrahydro-3H-benzimidazole.

¹H NMR (CDCl₃, 2 sets of signals): δ 1.15–1.50 (m, 2 H); 1.60–2.00 (m, 4 H); 2.35, 2.65, and 2.75 (dd, m, and dd, together 2 H); 3.05, 3.15, 3.27, and 3.40 (all m, together 2 H); 3.90 and 4.00 (both s, together 2 H); 4.25 and 4.40 (both s, together 2 H); 6.90–7.40 (m, 24 H).

Step 5

A solution of a mixture of 5-[2-(4-fluorobenzyl) benzyloxymethyl]1-triphenylmethyl-4,5,6,7-tetrahydro-1H-benzimidazole and 5-[2-(4-fluorobenzyl)benzyloxymethyl]-3-triphenylmethyl-4,5,6,7-tetrahydro-3H-benzimidazole (0.62 g, 1.0 mmol) in water (0.6 ml) and glacial acetic acid (5 ml) was heated to 90° C. for 2.5 h. The solvent was removed in vacuo. The residue was dissolved in ethyl acetate (50 ml). A 3.5 M solution of hydrogen chloride in ethyl acetate (0.6 ml, 2.1 mmol) was added. The solvent was removed in vauco. The residue was dissolved in ethyl acetate (30 ml). A precipitation appeared, which was isolated to give 235 mg of the hydrochloride salt of the title compound.

HPLC method C: elution at 10.66 min. $^1$H NMR (DMSO-$d_6$): δ 1.50 (m,1 H); 1.95 (m, 1 H); 2.05 (m, 1 H); 2.35 (m, 1 H); 2.60 (m, 2 H); 2.25 (dd, 1 H); 3.45 (d, 2 H); 4.05 (s, 1 H); 4.50 (s, 2 H); 7.05–7.40 (m, 8 H); 8.85 (s, 1 H); 14.15 (br, 2 H). MS: Calc for [M+H]$^+$: 351; Found: 351.

Example 55

5-[2-(3-(Trifluoromethoxy)phenoxy)benzyloxymethyl]-4,5,6,7-tetrahydro-1H-benzimidazole

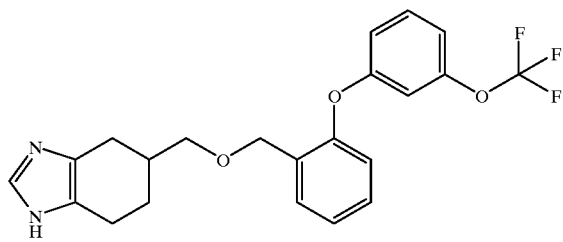

Step 1: 2-(3-(Trifluoromethoxy)phenoxy)benzonitrile

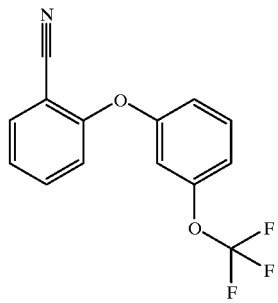

A mixture of potassium fluoride on alumina (40% w/w, Aldrich, 11 g), 2-fluorobenzonitrile (6.0 ml, 56 mmol), 3-trifluoromethoxyphenol (10 g, 56 mmol), and 18-crown-6 (1.48 g, 5.6 mmol) in dimethylsulphoxide (40 ml) was heated to 140° C. for 20 hours. The reaction mixture was cooled to room temperature and diluted with ethyl acetate (300 ml). The solid was filtered off through a plug of celite. The solution was washed with a mixture of water (100 ml) and brine (100 ml). The aqueous phase was extracted with ethyl acetate (2×50 ml). The combined organic layers were washed with water (100 ml) and dried over magnesium sulphate. The solvent was removed in vacuo. The crude product was purified by flash chromatography on silica (200 g), using ethyl acetate/heptane (1:3) as eluent, to give 9.80 g of 2-(3-(difluoromethoxy)phenoxy)benzonitrile.

$^1$H NMR (CDCl$_3$): δ 6.95 (m, 2 H); 7.00 (d, 1 H); 7.10 (d, 1 H); 7.25 (t, 1 H); 7.45 (t, 1 H); 7.55 (t, 1 H); 7.70 (d, 1 H). MS: Calc for [M+H]$^+$: 280; Found: 280.

Step 2: 2-(3-(Trifluoromethoxy)phenoxy)benzaldehyde

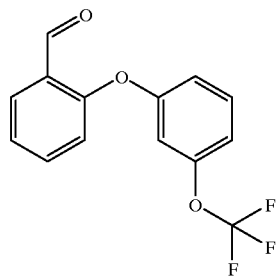

At 0° C., a 1.2 M solution of diisobutylaluminum hydride in toluene (38 ml, 45.6 mmol) was added dropwise to a solution of 2-(3-(difluoromethoxy)phenoxy)benzonitrile (9.80 g, 35.1 mmol) in THF (120 ml). The reaction mixture was stirred for 16 hours at room temperature. It was cooled to 0° C. Water (30 ml) was carefully added. The reaction mixture was warmed to room temperature and stirred for 1.5 hours. The precipitation was removed by filtration through a plug of celite. To the liquid a 10% aqueous solution of sodium hydrogensulphate (140 ml) was added. The mixture was stirred vigorously for 20 min. Ethyl acetate (200 ml) was added. The phases were separated. The aqueous phase was extracted with ethyl acetate (2×50 ml). The combined organic layers were washed with brine (2×200 ml) and dried over magnesium sulphate. The solvent was removed in vacuo. The crude product was purified by flash chromatography on silica (200 g), using ethyl acetate/heptane (1:3) as eluent, to give 6.28 g of 2-(3-(trifluoromethoxy)phenoxy)benzaldehyde.

$^1$H NMR (CDCl$_3$): δ 6.95 (m, 3 H); 7.05 (d, 1 H); 7.25 (t, 1 H); 7.40 (t, 1 H); 7.60 (t, 1 H); 8.00 (d, 1 H); 10.50 (s, 1 H).

Step 3: [2-(3-(Trifluoromethoxy)phenoxy)phenyl]methanol

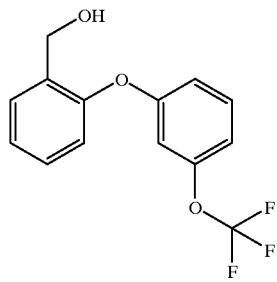

Sodium borohydride (1.17 g, 31.2 mmol) was added to a solution of 2-(3-(trifluoromethoxy)phenoxy)benzaldehyde (6.28 g, 22.3 mmol) in a mixture of DCM (20 ml) and isopropanol (10 ml). The reaction mixture was stirred for 16 hours at room temperature. A 10% aqueous solution of sodium hydrogensulphate was added until the evolution of hydrogen had ceased. The mixture was diluted with ethyl acetate (200 ml). Water (200 ml) was added. The phases were separated. The aqueous phase was extracted with ethyl acetate (2×100 ml). The combined organic layers were washed with a saturated aqueous solution of sodium hydrogencarbonate and dried over magnesium sulphate. The solvent was removed in vacuo. The crude product was purified by flash chromatography on silica (200 g), using ethyl acetate/heptane (1:2) as eluent, to give 5.34 g of [2-(3-(trifluoromethoxy)phenoxy)phenyl]methanol.

¹H NMR (CDCl₃): δ 1.95 (t,1 H); 4.75 (d, 2 H); 6.80–7.00 (m, 4 H); 7.15–7.40 (m, 3 H); 7.50 (d, 1 H).

Step 4: 2-(3-(Trifluoromethoxy)phenoxy)benzyl Bromide

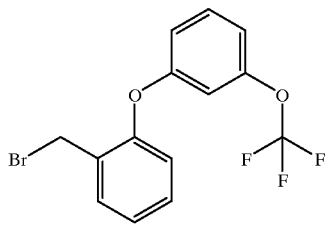

Phosphorus tribromide (5 ml, 53 mmol) was added to a solution of [2-(3-(trifluoromethoxy)phenoxy)phenyl]methanol (5.33 g, 18.9 mmol) in dioxane (100 ml). The reaction mixture was stirred for 1.5 hours. Another portion of phosphorus tribromide (5 ml, 53 mmol) was added. The reaction mixture was stirred for 16 hours at room temperature. It was diluted with ethyl acetate (500 ml) and washed with a 10% aqueous solution of sodium hydrogen sulphate (300 ml). The aqueous phase was extracted with ethyl acetate (2×100 ml). The combined organic layers were washed with a saturated aqueous solution of sodium hydrogencarbonate (200 ml) and dried over magnesium sulphate. The solvent was removed in vacuo. The crude product was purified on silica (200 g), using ethyl acetate/heptane (1:4) as eluent, to give 2.13 g of 2-(3-(trifluoromethoxy)phenoxy)benzyl bromide.

¹H NMR (CDCl₃): δ 4.55 (s, 2 H); 6.85–7.05 (m, 4 H); 7.15 (t, 1 H); 7.25–7.40 (m, 2 H); 7.50 (d,1 H).

Step 5: 5-[2-(3-(Trifluoromethoxy)phenoxy)benzyloxymethyl]-1-triphenylmethyl-4,5,6,7-tetrahydro-1H-benzimidazole and 5-[2-(3-(trifluoromethoxy)phenoxy)benzyloxymethyl]-3-triphenylmethyl4,5,6,7-tetrahydro-3H-benzimidazole

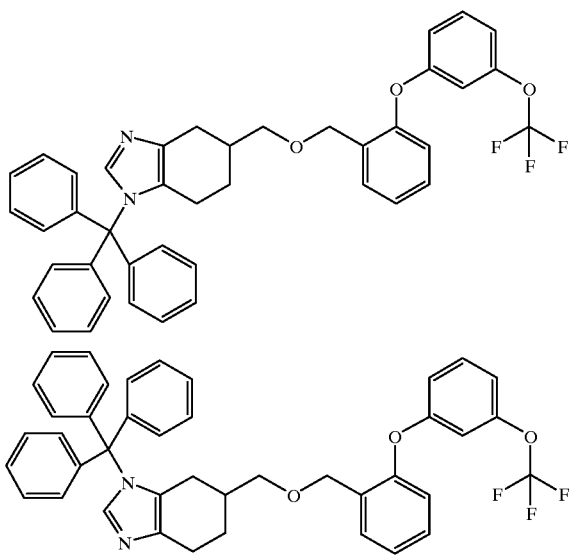

At 0° C., a 60% dispersion of sodium hydride in mineral oil (800 mg, 20 mmol) was added to a suspension of a mixture of (1-(triphenylmethyl)-4,5,6,7-tetrahydro-1H-benzimidazol-5-yl)methanol and (3-(triphenylmethyl)-4,5,6,7-tetrahydro-3H-benzimidazol-5-yl)methanol (394 mg, 1.0 mmol) in THF (4 ml). After the hydrogen evolution had ceased, a solution of 2-(3-(trifluoromethoxy)phenoxy) benzyl bromide (381 mg, 1.1 mmol) in THF (2 ml) was added. Tetrabutylammonium iodide (18 mg, 0.05 mmol) was added. The reaction mixture was stirred for 16 hours, while it was warming to room temperature. The reaction mixture was cooled to 0° C. Water (5 ml) was added carefully dropwise, until the hydrogen evolution had ceased. The mixture was diluted with ethyl acetate (100 ml) and a 10% aqueous solution of sodium hydrogensulphate (100 ml) was added. The phases were separated. The aqueous phase was extracted with ethyl acetate (2×50 ml). The combined organic layers were washed with a saturated aqueous solution of sodium hydrogencarbonate (100 ml) and dried over magnesium sulphate. The solvent was removed in vacuo. The crude product was purified by flash chromatography on silica (100 g), using ethyl acetate as eluent, to give 600 mg of a mixture of 5-[2-(3-(trifluoromethoxy)phenoxy) benzyloxymethyl]-1-triphenylmethyl-4,5,6,7-tetrahydro-1H-benzimidazole and 5-[2-(3-(trifluoromethoxy)phenoxy)benzyloxymethyl]-3-triphenylmethyl-4,5,6,7-tetrahydro-3H-benzimidazole.

¹H NMR (CDCl₃, 2 sets of signals) δ 1.05–1.40 (m, 2 H); 1.55–2.00 (m, 3 H); 2.35, 2.60, and 2.75 (dd, m, and dd, together 2 H); 3.15, 3.30, and 3.45 (m, dd, and dd, together 2 H); 4.35 and 4.50 (both s, together 2 H); 6.75, 6.90, 7.15, 7.30, and 7.50 (all m, together 18 H).

Step 6

A solution of a mixture of 5-[2-(3-(trifluoromethoxy) phenoxy)benzyloxymethyl]-1-triphenylmethyl-4,5,6,7-tetrahydro-1H-benzimidazole and 5-[2-(3-(trifluoromethoxy)phenoxy)benzyloxymethyl]-3-triphenylmethyl-4,5,6,7-tetrahydro-3H-benzimidazole (600 mg, 0.91 mmol) in a mixture of acetic acid (9 ml) and water (1 ml) was heated to 70° C. for 2 hours. The solvent was removed in vacuo. The crude product was purified by flash chromatography on silica (60 g), using DCM/methanol/25% aqueous ammonia as eluent, to give 251 mg of the title compound.

¹H NMR (CDCl₃): δ 1.55 (m, 1 H); 2.00 (m, 1 H); 2.15 (m, 1 H); 2.40 (dd, 1 H); 2.60 (m, 2 H); 2.70 (dd, 1 H); 3.50 (m, 2 H); 4.55 (s, 2 H); 6.75–7.00 (m, 4 H); 7.15–7.35 (m, 3 H); 7.45 (s, 1 H); 7.55 (d, 1 H). HPLC method C: elution at 11.33 min. MS: Calc for [M+H]⁺: 419; Found: 419.

For biological testing, the title compound was transformed into its hydrochloride salt, by dissolving it in ethyl acetate (10 ml) and addition of a 3.5 M solution of hydrogen chloride in ethyl acetate (1.5 ml, 5.25 mmol). The solvent was removed in vacuo.

Example 56

5-((5-Phenylpentyloxy)methyl)-4,5,6,7-tetrahydro-1H-benzimidazole

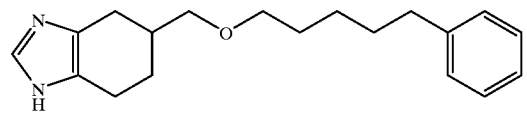

Step 1: 1-Bromo-5-phenylpentane

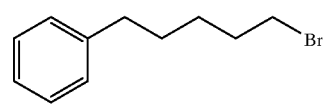

Phosphorus tribromide (4.7 ml, 49.8 mmol) was added dropwise to a solution of 5-phenylpentan-1-ol (3 ml, 17.8 mmol) in dioxane (70 ml). The reaction mixture was stirred for 2 hours at room temperature. Another portion of phosphorus tribromide (4.7 m. 49.8 mmol) was added. The reaction mixture was stirred for 16 h at room temprature. It was cooled to 0° C. Water (60 ml) was added dropwise. The reaction mixture was diluted with ethyl acetate (100 ml). The phases were separated. The aqueous phase was extracted with ethyl acetate (2×100 ml). The combined organic layers were washed with a saturated aqueous solution of sodium hydrogencarbonate (200 ml) and dried over magnesium sulfate. The solvent was removed in vacuo. The crude product was purified by flash chromatography on silica (50 g), using ethyl acetate/heptane (1:10) as eluent, to give 1.35 g of 1-bromo-5-phenylpentane.

$^1$H-NMR (CDCl$_3$): δ 1.50 (m, 2 H); 1.70 (m, 2 H); 1.90 (m, 2 H); 2.60 (m, 2 H); 3.40 (m, 2 H); 7.10 (m, 3 H); 7.30 (m, 2 H).

Step 2: 5-((5-Phenylpentlyoxy)methyl)-1-trityl-4,5,6,7-tetrahydro-1H-benzimidazole and 5-((5-phenylpentlyoxy) methyl)-3-trityl-4,5,6,7-tetrahydro-3H-benzimidazole

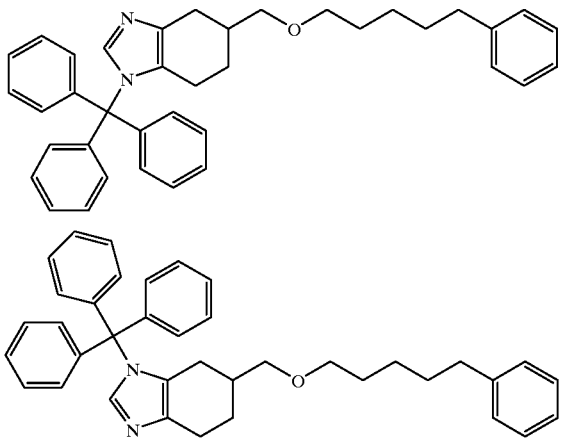

At 0° C., a 60% dispersion of sodium hydride in mineral oil (0.25 g, 6.34 mmol) was added to a solution of a solution of (1-(triphenylmethyl)-4,5,6,7-tetrahydro-1H-benzimidazol-5-yl)methanol and (3-(triphenylmethyl)-4,5, 6,7-tetrahydro-3H-benzimidazol-5-yl)methanol (0.50 g, 1.27 mmol) in N,N-dimethylformamide (10 ml). The reaction mixture was stirred for 20 min at room temperature. Tetrabutylammonium iodide (0.02 g, 0.06 mmol) was added. A solution of 1-bromo-5-phenylpentane (0.86 g, 3.80 mmol) in N,N-dimethylformamide (3 ml) was added. The reaction mixture was heated to 60° C. for 16 h. It was cooled to room temperature. Water (60 ml) was added dropwise. The reaction mixture was extracted with ethyl acetate (3×70 ml). The combined organic layers were washed with a saturated aqueous solution of sodium hydrogencarbonate (100 ml) and dried over magnesium sulfate. The solvent was removed in vacuo. The crude product was purified by flash chromatography on silica (90 g), using a gradient of ethyl acetate/ heptane (from 1:1 to 3:1) as eluent, to give 0.53 g of a mixture of 5-((5-phenylpentlyoxy)methyl)-1-trityl-4,5,6,7-tetrahydro-1H-benzimidazole and 5-((5-phenylpentlyoxy) methyl)-3-trityl-4,5,6,7-tetrahydro-3H-benzimidazole.

$^1$H NMR (CDCl$_3$) δ 1.10–2.20 (m, 13 H); 2.65 and 3.00–3.55 (m, 5 H) 4.15 (m, 1 H); 7.00–7.50 (m,16 H).

Step 3

A solution of a mixture of 5-((5-phenylpentlyoxy) methyl)-1-trityl-4,5,6,7-tetrahydro-1H-benzimidazole and 5-((5-phenylpentlyoxy)methyl)-3-trityl-4,5,6,7-tetrahydro-3H-benzimidazole (0.53 g, 0.98 mmol) in glacial acetic acid (5 ml) and water (0.6 ml) was heated to 90° C. for 2 hours. The solvent was removed in vacuo. The crude product was purified by flash chromatography on silica (40 g), using a mixture of DCM/methanol/25% aqueous ammonia (100:10:1) as eluent, to give 0.25 g of the title compound.

$^1$H NMR (CDCl$_3$): δ 1.40 (m, 2 H); 1.50 (m, 1 H); 1.65 (m, 4 H); 2.05 (m, 1 H); 2.15 (m, 1 H); 2.30 (dd, 1 H); 2.60 (m, 4 H); 2.70 (dd, 1 H); 3.40 (m, 4 H); 5.00 (br, 1 H); 7.15 (m, 3 H); 7.30 (m, 2 H); 7.45 (s, 1 H). HPLC method C: elution at 11.23 min. MS: Calc for [M+H]$^+$: 299; found: 299.

For biological testing, the title compound was transformed into its hydrochloride salt, by dissolving it in ethyl acetate (10 ml) and addition of a 3.5 M solution of hydrogen chloride in ethyl acetate (1.5 ml, 5.25 mmol). The solvent was removed in vacuo. The residue was dissolved in acetone (5 ml). The solvent was removed in vacuo.

Example 57

4-(1,4,5,6,7,8-Hexahydrocycloheptaimidazol-4-ylmethoxy) benzonitrile, Hydrochloride

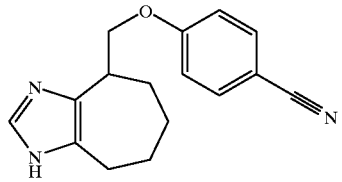

Using the same procedure as described for example 22, from (1-trityl-1,4,5,6,7,8-hexahydrocycloheptaimidazole-4-yl)methanol and 4-cyanophenol was obtained the title compound.

Mp. 232–235° C. $^1$H NMR (DMSO-d$_6$): δ 1.41 (m, 1H), 1.54 (m, 1H), 1.62–1.86 (m, 4H), 2.79 (m, 2H), 3.03 (dd, J=6Hz, 16Hz, 1H), 3.22 (dd, J=4Hz, 16Hz, 1H), 7.12 (d, J=8Hz, 2H), 7.78 (d, J=8Hz, 2H), 8.39 (s, 1H), 14.15 (s, 2H). HPLC-MS: m/z=268 (MH$^+$).

Example 58

4-(4-Trifluoromethoxyphenoxymethyl)-4,5,6,7-tetrahydro-1H-benzimidazole, Hydrochloride

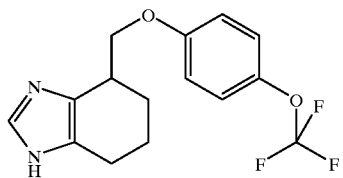

Using the same procedure as described for Example 22, from 4-hydroxymethyl-1-triphenylmethyl-4,5,6,7-tetrahydro-1H-benzimidazole and 4-(trifluoromethoxy) phenol was obtained the title compound.

Mp. 202–209° C. $^1$H NMR (DMSO-d$_6$) δ 1.78 (m, 2H), 1.95 (m, 2H), 2.62 (m, 2H), 3.29 (m, 1H), 4.21 (d, J=5Hz, 2H), 7.10 (d, J=8Hz, 2H), 7.31 (d, J=8Hz, 2H), 8.97 (s, 1H), 14.30 (s, 2H). HPLC-MS: m/z=313 (MH$^+$).

Microanalysis:

Calc: C: 51.66%, H: 4.62%, N: 8.03%;

Found: C: 51.89%, H: 4.74%, N: 8.21%.

Example 59

4-(4-Trifluoromethylphenoxymethyl)-4,5,6,7-tetrahydro-1H-benzimidazole, Hydrochloride

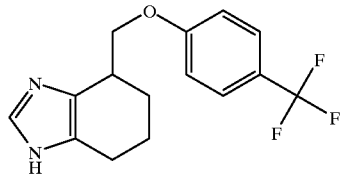

Using the same procedure as described for Example 22, from 4-hydroxymethyl-1-triphenylmethyl-4,5,6,7-tetrahydro-1H-benzimidazole and 4-(trifluoromethyl)phenol was obtained the title compound.

Mp. 242–244° C. $^1$H NMR (DMSO-$d_6$): δ 1.79 (m, 2H), 1.96 (m, 2H), 2.62 (m, 2H), 4.25 (m, 2H), 7.19 (d, J=8Hz, 2H), 7.68 (d, J=8Hz, 2H), 8.94 (s, 1H), 14.15 (s, 2H). HPLC-MS: m/z=297 (MH$^+$).

Microanalysis:

Calc: C: 54.14%, H: 4.85%, N: 8.42%;

Found: C: 53.86%, H: 4.89%, N: 8.29%.

Example 60

3,5-Dimethyl-4-(4,5,6,7-tetrahydro-1H-benzimidazol-4-ylmethoxy)benzonitrile, Hydrochloride

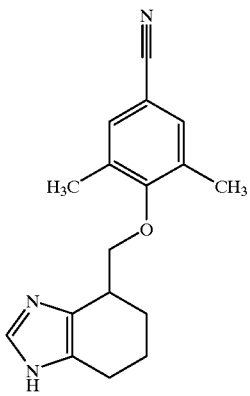

Using the same procedure as described for Example 22, from 4-hydroxymethyl-1-triphenylmethyl-4,5,6,7-tetrahydro-1H-benzimidazole and 4-cyano-2,6-dimethylphenol was obtained the title compound.

Mp. 190–192° C. $^1$H NMR (DMSO-$d_6$) δ 1.79 (m, 1H), 1.91–2.10 (m, 3H), 2.22 (s, 6H), 2.63 (m, 2H), 3.31 (m, 1H), 3.95–4.08 (m, 2H), 7.56 (s, 2H), 8.97 (s, 1H), 14.40 (s, 2H). HPLC-MS: m/z=282 (MH$^+$).

Microanalysis for ($C_{17}H_{19}N_3O$,HCl,$H_2O$):

Calc: C: 60.80%, H: 6.60%, N: 12.51%;

Found: C: 60.70%, H: 6.88%, N: 12.44%.

Example 61

3-Chloro-4-(4,5,6,7-tetrahydro-1H-benzimidazol-4-ylmethoxy)benzonitrile, Hydrochloride

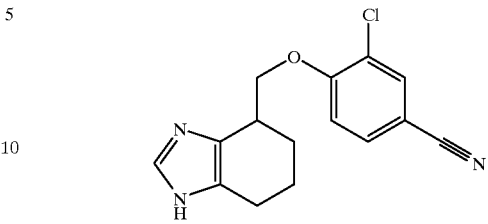

Using the same procedure as described for Example 22, from 4-hydroxymethyl-1-triphenylmethyl-4,5,6,7-tetrahydro-1H-benzimidazole and 4-cyano-2-chlorophenol was obtained the title compound.

Mp. 225–227° C. $^1$H NMR (DMSO-$d_6$): δ 1.75–1.91 (m, 2H), 2.00 (m, 2H), 2.61 (m, 2H), 4.38 (m, 1H), 4.49 (m, 1H), 7.40 (d, J=8Hz, 1H), 7.85 (d, J=8Hz, 1H), 8.04 (d, J=1Hz, 1H), 8.95 (s, 1H), 14.25 (s, 2H). HPLC-MS: m/z=288 (MH$^+$).

Microanalysis for ($C_{15}H_{14}ClN_3O$,HCl, 0.25$H_2O$):

Calc: C: 54.81%, H: 4.75%, N: 12.78%;

Found: C: 55.10%, H: 4.73%; N: 12.73%.

Example 62

3-(4,5,6,7-Tetrahydro-1H-benzimidazol-4-ylmethoxy)benzonitrile, Hydrochloride

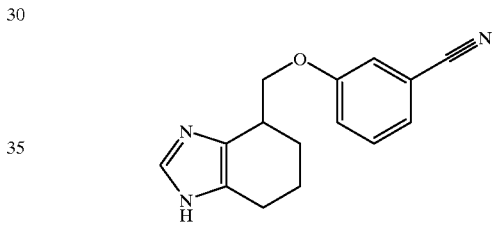

Using the same procedure as described for Example 22, from 4-hydroxymethyl-1-triphenylmethyl-4,5,6,7-tetrahydro-1H-benzimidazole and 3-cyanophenol was obtained the title compound.

$^1$H NMR (DMSO-$d_6$): δ 1.79 (m, 2H), 1.94 (m, 2H), 2.63 (m, 2H), 3.29 (m, 1H), 4.23 (m, 2H), 7.35–7.53 (m, 4H), 8.97 (s, 1H), 14.30 (s, 2H). HPLC-MS: m/z=254 (MH$^+$).

Example 63

Cyclopropyl-[4-(4,5,6,7-tetrahydro-1H-benzimidazol-4-ylmethoxy)phenyl]methanone, hydrochloride

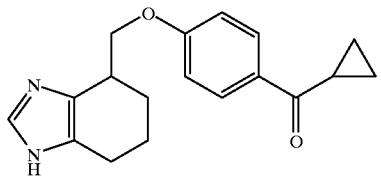

Using the same procedure as described for Example 22, from 4-hydroxymethyl-1-triphenylmethyl-4,5,6,7-tetrahydro-1H-benzimidazole and 4-cyclopropanoylphenol was obtained the title compound.

Mp. 211–213° C. $^1$H NMR (DMSO-$d_6$) δ 0.99 (m, 4H), 1.81 (m, 2H), 1.95 (m, 2H), 2.63 (m, 2H), 2.86 (quint, J=6Hz, 1H), 3.30 (m, 1H), 4.29 (m, 2H), 7.13 (d, J=8Hz, 2H), 8.03 (d, J=8 Hz, 2H), 8.97 (s, 1H), 14.35 (s, 2H).

HPLC-MS: m/z=297 (MH+).

Microanalysis:

Calc: C: 64.96%, H: 6.36%, N: 8.42%;

Found: C: 65.04%, H: 6.41%, N: 8.30%.

Example 64

3-Methoxy-4-(4,5,6,7-tetrahydro-1H-benzimidazol-4-ylmethoxy)benzonitrile, Hydrochloride

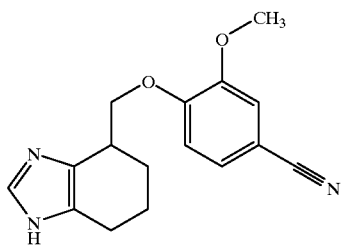

Using the same procedure as described for Example 22, from 4-hydroxymethyl-1-triphenylmethyl-4,5,6,7-tetrahydro-1H-benzimidazole and 4-cyano-2-methoxyphenol was obtained the title compound.

Mp. 193–195° C. $^1$H NMR (DMSO-d$_6$) δ 1.72–2.01 (m, 4H), 2.61 (m, 2H), 3.31 (m, 1H), 3.80 (s, 3H), 4.22 (t, J=8Hz, 1H), 4.39 (dd, J=3Hz, 8Hz, 1H), 7.21 (d, J=8Hz, 1H), 7.41 (m, 2H), 8.96 (s, 1H), 14.35 (s, 2H). HPLC-MS: m/z=284 (MH+).

Microanalysis for $C_{16}H_{17}N_3O_2$, HCl, H$_2$O:

Calc: C: 56.89%, H: 5.97%, N: 12.44%;

Found: C: 56.93%, H: 5.98%, N: 12.24%.

Example 65

5-(4,5,6,7-Tetrahydro-1H-benzimidazol-4-ylmethoxy)-3,4-dihydro-2H-naphthalen-1-one, Hydrochloride

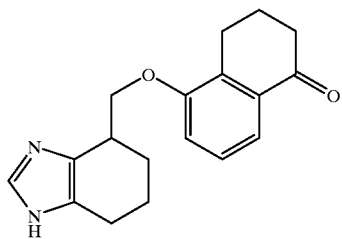

Using the same procedure as described for Example 22, from 4-hydroxymethyl-1-triphenylmethyl-4,5,6,7-tetrahydro-1H-benzimidazole and 5-hydroxy-1-tetralone was obtained the title compound.

Mp. 237–240° C. $^1$H NMR (DMSO-d$_6$): δ 1.73–2.07 (m, 6H), 2.55 (t, J=6Hz, 2H), 2.64 (m, 2H), 2.66–2.84 (m, 2H), 3.31 (m,1H), 4.31 (dd, J=6 Hz, 8 Hz,1H), 4.36 (dd, J=3 Hz, 8 Hz, 1H), 7.26–7.34 (m, 2H), 7.49 (d, J=8 Hz,1H), 8.98 (s, 1H), 14.35 (s, 2H). HPLC-MS: m/z=297 (MH+).

Microanalysis:

Calc: C: 64.96%, H: 6.36%, N: 8.42%;

Found: C: 65.03%, H: 6.46%, N: 8.13%.

Example 66

4-(4-Chlorophenoxymethyl)-4,5,6,7-tetrahydro-1H-benzimidazole, Hydrochloride

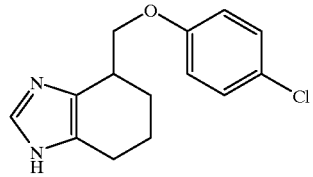

Using the same procedure as described for Example 22, from 4-hydroxymethyl-1-triphenylmethyl-4,5,6,7-tetrahydro-1H-benzimidazole and 4-chlorophenol was obtained the title compound.

Mp. 210–212° C. $^1$H NMR (DMSO-d$_6$): δ 1.79 (m, 2H), 1.93 (m, 2H), 2.61 (m, 2H), 3.28 (m, 1H), 4.15 (d, J=6 Hz, 2H), 7.03 (d, J=8 Hz, 2H), 7.33 (d, J=8 Hz, 2H), 8.93 (s, 1H), 14.20 (s, 2H). HPLC-MS: m/z=263 (MH+).

Microanalysis:

Calc: C: 56.20%, H: 5.39%, N: 9.36%;

Found: C: 56.38%, H: 5.45%, N: 9.23%.

Examle 67

[5-Chloro-2-(4,5,6,7-tetrahydro-1H-benzimidazol-4-ylmethoxy)phenyl]phenylmethanone, Hydrochloride

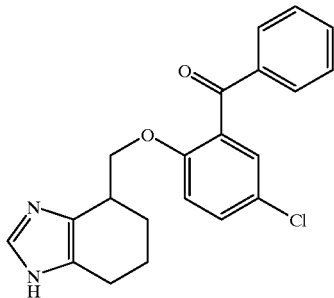

Using the same procedure as described for Example 22, from 4-hydroxymethyl-1-triphenylmethyl-4,5,6,7-tetrahydro-1H-benzimidazole and 2-benzoyl-4-chlorophenol was obtained the title compound.

$^1$H NMR (DMSO-d$_6$): δ 1.10 (m, 1H), 1.40–1.64 (m, 3H), 2.12 (m, 1H), 2.39 (m, 1H), 2.96 (m, 1H), 4.22 (m, 2H), 7.26 (d, J=8 Hz, 1H), 7.42 (m, 3H), 7.56 (d, J=7 Hz, 2H), 7.62 (m, 2H), 8.82 (s, 1H), 14.15 (s, 2H). HPLC-MS: m/z=366 (MH+).

Microanalysis for $C_{21}H_{19}ClN_2O_2$, HCl, 0.5H$_2$O:

Calc: C: 61.17%, H: 5.13%, N: 6.79%;

Found: C: 61.08%, H: 5.03%, N: 6.61%.

Pharmacological Methods

The ability of the compounds to interact with the histamine H3 receptor can be determined by the following in vitro binding assays.

Binding Assay I

Rat cerebral cortex is homogenized in ice cold K-Hepes, 5 mM MgCl$_2$ pH 7.1 buffer. After two differential centrifugations the last pellet is resuspended in fresh Hepes buffer containing 1 mg/ml bacitracin. Aliquots of the membrane suspension (400 μg/ml) are incubated for 60 min at 25° C. with 30 pM [$^{125}$I]-iodoproxifan, a known histamine H3 receptor antagonist, and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analyzed by nonlinear regression analysis.

Binding Assay II

The H3-receptor agonist ligand R-α-methyl[$^3$H]histamine (RAMHA) is incubated with isolated rat cortex cell-membranes at 25° C. for 1 hour, followed by a filtration of the incubate through Whatman GF/B filters. Radioactivity retained on the filters is measured using a beta counter.

Male Wistar rats (150–200 g) are decapitated and cerebral cortex is quickly dissected out and frozen immediately on dry ice. Tissue is kept at –80° C. until membrane preparation. During the membrane preparation the tissue is kept on ice all the time. Rat cerebral cortex is homogenized in 10 volumes (w/w) ice-cold Hepes buffer (20 mM Hepes, 5 mM MgCl$_2$ pH 7.1 (KOH) +1 mg/ml bacitracin) using an Ultra-Turrax homogenizer for 30 seconds. The homogenate is centrifuged at 140 g in 10 min. The supernatant is transferred to a new test tube and centrifuged for 30 min at 23 000 g. Pellet is resuspended in 5–10 ml Hepes buffer, homogenized and centrifuged for 10 min at 23 000 g. This short centrifugation step is repeated twice. After the last centrifugation the pellet is resuspended in 2–4 ml Hepes buffer and the protein concentration is determined. The membranes are diluted to a protein concentration of 5 mg/ml using Hepes buffer, aliquoted and stored at –80° C. until use 50 µl test-compound, 100 µl membrane (200 µg/ml), 300 µl Hepes buffer and 50 µl R-α-methyl[$^3$H]histamine (1 nM) are mixed in a test tube. The compounds to be tested are dissolved in DMSO and further diluted in H$_2$O to the desired concentrations. Radioligand and membranes are diluted in Hepes buffer+1 mg/ml bacitracin. The mixture is incubated for 60 min at 25° C. Incubation is terminated by adding 5 ml ice-cold 0.9% NaCl, followed by rapid filtration through Whatman GF/B filters pre-treated for 1 h with 0.5% polyethyleneimine. The filters are washed with 2×5 ml ice-cold NaCl. To each filter a 3 ml scintillation cocktail is added and the radioactivity retained is measured with a Packard Tri-Carb beta counter.

IC$_{50}$ values are calculated by non-linear regression analysis of binding curves.

(6 points minimum) using the windows program Graph-Pad Prism, GraphPad software, USA.

Binding Assay III

The human H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM (GIBCO-BRL) with glutamax, 10% foetal calf serum, 1% penicillin/streptavidin and 1 mg/ml G 418 at 37° C. and 5% CO$_2$. Before harvesting, the confluent cells are rinsed with PBS and incubated with Versene (proteinase, GIBCO-BRL) for approximately 5 min. The cells are flushed with PBS and DMEM and the cellsuspension collected in a tube and centrifuged for 5–10 min at 1500 rpm in a Heraeus Sepatech Megafuge 1.0. The pellet is resuspended in 10–20 vol. Hepes buffer (20 mM Hepes, 5 mM MgCl$_2$, pH 7.1 (KOH)) and homogenized for 10–20 seconds using an Ultra-Turrax homogenizer. The homogenate is centrifuged for 30 min at 23 000 g. The pellet is resuspended in 5–10 ml Hepes buffer, homogenized 5–10 seconds with the Ultra-Turrax and centrifuged for 10 min at 23 000 g. Following this centrifugation step, the membrane pellet is resuspended in 2–4 ml Hepes buffer, homogenized with a syringe or teflonhomogenizer, and the protein concentration determined. The membranes are diluted to a protein concentration of 1–5 mg/ml in Hepes buffer, aliquoted and kept at –80° C. until use.

Aliquots of the membrane suspension are incubated for 60 min at 25° C. with 30 pM [$^{125}$I]-iodoproxifan, a known compound with high affinity for the H3 receptor, and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analyzed by nonlinear regression analysis.

When tested, the present compounds of the formula (I) generally show a high binding affinity to the histamine H3 receptor.

Preferably, the compounds according to the invention have an IC$_{50}$ value as determined by one or more of the assays of less than 10 µM, more preferred of less than 1 µM, and even more preferred of less than 500 nM, such as of less than 100 nM.

Functional Assay I

The ability of the compounds to interact with the histamine H3 receptor as agonists, inverse agonists and/or antagonists, is determined by an in vitro functional assay utilizing membranes from HEK 293 cell expressing the human H3 receptors.

The H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM with glutamax, 10% foetal calf serum, 1% penicillin/streptavidin and 1 mg/ml G 418 at 37° C. and 5% CO$_2$.

The H3 receptor expressing cells are washed once with phosphate buffered saline (PBS) and harvested using versene (GIBCO-BRL). PBS is added and the cells are centrifuged for 5 min at 188 g. The cell pellet is resuspended in stimulation buffer to a concentration of 1×10$^6$ cells/ml. cAMP accumulation is measured using the Flash Plate® cAMP assay (NEN™ Life Science Products). The assay is generally performed as described by the manufacturer. Briefly, 50 µl cell suspension is added to each well of the Flashplate which also contained 25 µl 40 µM isoprenaline, to stimulate cAMP generation, and 25 µl of test compound (either agonists or inverse agonists alone, or agonist and antagonist in combination). The assay can be run in "agonist-mode" which means that the test compound is added, in increasing concentration, on its own, to the cells, and cAMP is measured. If cAMP goes up, it is an inverse agonist; if cAMP does not change, it is a neutral antagonist, and if cAMP goes down, it is an agonist. The assay can also be run in the "antagonist-mode" which means that a test compound is added, in increasing concentrations, together with increasing concentrations of a known H3 agonist (eg RAMHA). If the compound is an antagonist, increasing concentrations of it cause a right-ward shift in the H3-agonist's dose-response curves. The final volume in each well is 100 µl. Test compounds are dissolved in DMSO and diluted in H$_2$O. The mixture is shaken for 5 min, and allowed to stand for 25 min at room temperature. The reaction is stopped with 100 µl "Detection Mix" per well. The plates are then sealed with plastic, shaken for 30 min, allowed to stand overnight, and finally the radioactivity is counted in the Cobra II auto gamma topcounter. $EC_{50}$ values are calculated by non-linear regression analysis of dose response curves (6 points minimum) using GraphPad Prism. Kb values are calculated by Schild plot analysis.

The ability of the present compounds to reduce weight is determined using the in vivo open cage Schedule-fed rat model.

The Open Cage Schedule-Fed Rat Model

Sprague-Dawley (SD) male rats of an age of about 1½ to 2 months and a weight of about 250 g are habituated to the presence of food (Altromin pelleted rat chow) in their home cage only during three hours in the morning from 9 to 12 a.m. all days a week. Water is present ad libitum. As the consumption of food stabilised after 7 to 9 days, the animals are ready for use.

The animals are tested twice a week. During the test sessions, the test compound is administered intraperitoneally 30 min before the start of the sessions. One group of 9 animals is administered the test compound at a dose of 15 mg/kg and another group of 11 animals is administered the test compound at a dose of 30 mg/kg. A control group of 11 animals is administered the vehicle consisting of NaCl 0.9% and Chremophor 5%. Food and water intake are monitored at 1, 2 and 3 hours post administration.

During the test period the animals are weighed weekly and if necessary extra food is given in order to ensure that the weight gain is 3 to 5 g per week corresponding to the normal weight gain for SD male rats at this age.

Any side effects could rapidly be discovered (barrel-rolling, bushy fur etc.) since the animals are kept in transparent plastic cages to enable continuous monitoring.

What is claimed is:

1. A compound of formula (I):

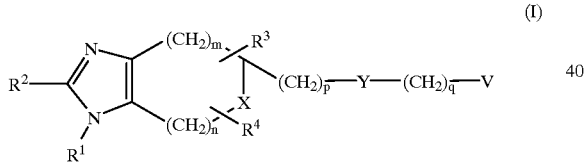

(I)

wherein $R^1$ is hydrogen or a functional group that can be converted to hydrogen in vivo, $R^2$ is hydrogen, $C_{1-6}$-alkyl, $C_{1-6}$-alkoxy, $C_{1-6}$-alkylthio, halogen, cyano, trifluoromethyl, hydroxy, thiol or —$NR^5R^6$, wherein $R^5$ and $R^6$ independently are hydrogen or $C_{1-6}$-alkyl, $R^3$ and $R^4$ independently are hydrogen or $C_{1-6}$-alkyl, which is unsubstituted or substituted with aryl, which are unsubstituted or substituted with one or more substituents selected from nitro, —$NR^7R^8$, —$S(=O)_2$ $NR^7R^8$, —$C(=O)NR^7R^8$, hydroxy, halogen, cyano, trifluoromethyl, —$OCF_3$, —$OCHF_2$, —$OCH_2CHF_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —$C(=O)OR^7$, $C_{1-6}$-alkyl-carbonyl, —$C(=NOR^7)C_{1-6}$-alkyl, $C_{3-10}$-cycloalkyl, $C_{3-10}$-cycloalkylcarbonyl, —$C(=NOR^7)$ $C_{3-10}$-cycloalkyl, aryl-$C_{1-6}$-alkyl, arylamino, aroyl, arylsulfonyl, —$C(=NOR^7)$aryl, arylthio, and aryloxy, wherein $R^7$ and $R^8$ independently are hydrogen or $C_{1-6}$-alkyl, m is 0, n is 1, 2, 3 or 4, X is a valence bond, p is 0, 1, 2 or 3, Y is —O—, q is 0, 1, 2 or 3, V is aryl or $C_{3-10}$-cycloalkyl, which are unsubstituted or substituted with one or more substituents selected from nitro, —$NR^{10}R^{11}$, —$S(=O)_2$ $NR^{10}R^{11}$, —$C(=O)NR^{10}R^{11}$, hydroxy, halogen, cyano, trifluoromethyl, —$OCF_3$, —$OCHF_2$, —$OCH_2CHF_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —$C(=O)OR^{10}$, $C_{1-6}$-alkylcarbonyl, —$C(=NOR^{10})$ $C_{1-6}$-alkyl, oxo, $C_{3-10}$-cycloalkyl, $C_{3-10}$-cycloalkylcarbonyl, —$C(=NOR^{10})C_{3-10}$-cycloalkyl, arylamino, aroyl, arylsulfonyl, —$C(=NOR^{10})$aryl, and arylthio, wherein $R^{10}$ and $R^{11}$ independently are hydrogen or $C_{1-6}$-alkyl, aryl-$C_{1-6}$-alkyl, aryl or aryloxy, which are unsubstituted or substituted with one or more substituents selected from nitro, hydroxy, $C_{1-6}$-alkyl, $C_{1-6}$-alkoxy, cyano, trifluoromethyl, —$OCF_3$, halogen $C_{1-6}$-alkyl, $C_{2-6}$-alkenyl or $C_{2-6}$-alkynyl, which are unsubstituted or substituted with one or more substituents selected from $C_{3-10}$-cycloalkyl, and aryl, which are unsubstituted or substituted with one or more substituents selected from nitro, —$NR^{12}R^{13}$, —$S(=O)_2NR^{12}R^{13}$, —$C(=O)$ $NR^{12}R^{13}$, hydroxy, halogen, cyano, trifluoromethyl, —$OCF_3$, —$OCHF_2$, —$OCH_2CHF_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —$C(=O)OR^{12}$, $C_{1-6}$-alkylcarbonyl, —$C(=NOR^{12})C_{1-6}$-alkyl, $C_{3-10}$-cycloalkyl, $C_{3-10}$-cycloalkylcarbonyl, —$C(=NOR^{12})$ $C_{3-10}$-cycloalkyl, aryl-$C_{1-6}$-alkyl, arylamino, aroyl, arylsulfonyl, —$C(=NOR^{12})$aryl, arylthio, and aryloxy, wherein $R^{12}$ and $R^{13}$ independently are hydrogen or $C_{1-6}$-alkyl, or any stereoisomer or tautomeric form thereof or a mixture thereof or a pharmaceutically acceptable salt thereof.

2. The compound according to claim 1 wherein $R^1$ is hydrogen.

3. The compound according to claim 1 wherein $R^2$ is hydrogen.

4. The compound according to claim 1 wherein $R^3$ and $R^4$ are both hydrogen.

5. The compound according to claim 1 wherein n is 3 or 4.

6. The compound according to claim 1 wherein p is 1.

7. The compound according to claim 1 wherein p is 2.

8. The compound according to claim 1 wherein q is 0.

9. The compound according to claim 1 wherein q is 1.

10. The compound according to claim 1 wherein V is selected from unsubstituted or substituted aryl annulated with aryl.

11. The compound according to claim 10 wherein V is selected from unsubstituted or substituted phenyl, naphthyl, tetrahydronaphthyl and 3,4-methylenedioxyphenyl.

12. The compound according to claim 11 wherein V is unsubstituted or substituted phenyl.

13. The compound according to claim 12 wherein V is unsubstituted or substituted naphthyl.

14. The compound according to claim 10 wherein V is unsubstituted or substituted with one or two substituents independently selected from
halogen, $C_{3-10}$-cycloalkylcarbonyl, cyano, $C_{1-6}$-alkylcarbonyl, —C(=O)OR$^{10}$, $C_{1-6}$-alkyl, $C_{1-6}$-alkoxy, —CF$_3$ and —OCF$_3$,
wherein R$^{10}$ is unsubstituted or substituted aryl-$C_{1-6}$-alkyl, aryl or aryloxy.

15. The compound according to claim 14, wherein V is unsubstituted or substituted with one or two substituents independently selected from
halogen, $C_{3-10}$-cycloalkylcarbonyl, cyano, $C_{1-6}$-alkylcarbonyl, —C(=O)OR$^{10}$, $C_{1-6}$-alkyl, $C_{1-6}$-alkoxy, —CF$_3$ and —OCF$_3$,
wherein R$^{10}$ is unsubstituted or substituted phenyl-$C_{1-6}$-alkyl, phenyl or phenoxy.

16. The compound according to claim 15 wherein V is unsubstituted or substituted with one or two substituents independently selected from phenyl, phenoxy and trifluoromethyl.

17. The compound according to claim 1 wherein V is unsubstituted or substituted $C_{1-6}$-alkyl or $C_{2-6}$-alkenyl.

18. The compound according to claim 17 wherein V is $C_{1-6}$-alkyl or $C_{2-6}$-alkenyl, which is substituted with unsubstituted or substituted aryl.

19. The compound according to claim 18 wherein V is $C_{1-6}$-alkyl or $C_{2-6}$-alkenyl, which is substituted with unsubstituted or substituted phenyl.

20. A method of treating obesity comprising administering the compound of claim 1 to a patient in need thereof.

21. A method of suppressing appetite, comprising administering the compound of claim 1 to a patient in need thereof.

22. A method of treating type 2 diabetes comprising administering the compound of claim 1 to a patient in need thereof.

23. The compound according to claim 1 having formula (Ih):

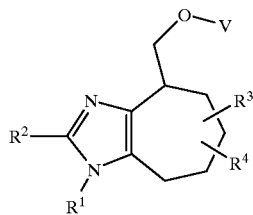

(Ih)

wherein
R$^1$ is hydrogen or a functional group that can be converted to hydrogen in vivo,
R$^2$ is hydrogen, $C_{1-6}$-alkyl, $C_{1-6}$-alkoxy, $C_{1-6}$-alkylthio, halogen, cyano, trifluoromethyl, hydroxy, thiol or —NR$^5$R$^6$, wherein R$^5$ and R$^6$ independently are hydrogen or $C_{1-6}$-alkyl,
R$^3$ and R$^4$ independently are hydrogen or $C_{1-6}$-alkyl, which is unsubstituted or substituted with aryl, which are unsubstituted or substituted with one or more substituents selected from nitro, —NR$^7$R$^8$, —S(=O)$_2$NR$^7$R$^8$, —C(=O)NR$^7$R$^8$, hydroxy, halogen, cyano, trifluoromethyl, —OCF$_3$, —OCHF$_2$, —OCH$_2$CHF$_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —C(=O)OR$^7$, $C_{1-6}$-alkyl-carbonyl, —C(=NOR$^7$)$C_{1-6}$-alkyl, $C_{3-10}$-cycloalkyl, $C_{3-10}$-cycloalkylcarbonyl, —C(=NOR$^7$)$C_{3-10}$-cycloalkyl, aryl-$C_{1-6}$-alkyl, arylamino, aroyl, arylsulfonyl, —C(=NOR$^7$)aryl, arylthio, and aryloxy, wherein R$^7$ and R$^8$ independently are hydrogen or $C_{1-6}$-alkyl, V is
aryl or $C_{3-10}$-cycloalkyl,
which are unsubstituted or substituted with one or more substituents selected from nitro, —NR$^{10}$R$^{11}$, —S(=O)$_2$ NR$^{10}$ R$^{11}$, —C(=O)NR$^{11}$R$^{11}$, hydroxy, halogen, cyano, trifluoromethyl, —OCF$_3$, —OCHF$_2$, —OCH$_2$CHF$_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —C(=O)OR$^{10}$, $C_{1-6}$-alkylcarbonyl, —C(=NOR$^{10}$) $C_{1-6}$-alkyl, oxo, $C_{3-10}$-cycloalkyl, $C_{3-10}$-cycloalkylcarbonyl, —C(=NOR$^{10}$)$C_{3-10}$-cycloalkyl, arylamino, aroyl, arylsulfonyl, —C(=NOR$^{10}$)aryl, and arylthio, wherein R$^{10}$ and R$^{11}$ independently are hydrogen or $C_{1-6}$-alkyl,
aryl-$C_{1-6}$-alkyl, aryl or aryloxy, which are unsubstituted or substituted with one or more substituents selected from
nitro, hydroxy, $C_{1-6}$-alkyl, $C_{1-6}$-alkoxy, cyano, trifluoromethyl, —OCF$_3$, halogen
$C_{1-6}$-alkyl, $C_{2-6}$-alkenyl or $C_{2-6}$-alkynyl,
which are unsubstituted or substituted with one or more substituents selected from $C_{3-10}$-cycloalkyl and aryl, which are unsubstituted or substituted with one or more substituents selected from
nitro, —NR$^{12}$R$^{13}$, —S(=O)$_2$NR$^{12}$R$^{13}$, —C(=O) NR$^{12}$R$^{13}$, hydroxy, halogen, cyano, trifluoromethyl, —OCF$_3$, —OCHF$_2$, —OCH$_2$CHF$_2$, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkylsulfonyl, —C(=O)OR$^{12}$, $C_{1-6}$-alkylcarbonyl, —C(=NOR$^{12}$)$C_{1-6}$-alkyl, $C_{3-10}$-cycloalkyl, $C_{3-10}$-cycloalkylcarbonyl, —C(=NOR$^{12}$) $C_{3-10}$-cycloalkyl, aryl-$C_{1-6}$-alkyl, arylamino, aroyl, arylsulfonyl, —C(=NOR$^{12}$)aryl, arylthio, and aryloxy, wherein R$^{12}$ and R$^{13}$ independently are hydrogen or $C_{1-6}$-alkyl,
or any stereoisomer or tautomeric form thereof or a mixture thereof or a pharmaceutically acceptable salt thereof.

24. The compound according to claim 1 having formula (Ii):

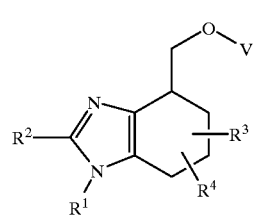

(Ii)

wherein
R$^1$ is hydrogen or a functional group that can be converted to hydrogen in vivo,
R$^2$ is hydrogen, $C_{1-6}$-alkyl, $C_{1-6}$-alkoxy, $C_{1-6}$-alkylthio, halogen, cyano, trifluoromethyl, hydroxy, thiol or —NR$^5$R$^6$, wherein R$^5$ and R$^6$ independently are hydrogen or $C_{1-6}$-alkyl,
R$^3$ and R$^4$ independently are hydrogen or $C_{1-6}$-alkyl, which is unsubstituted or substituted with aryl, which are unsubstituted or substituted with one or more substituents selected from nitro, —NR$^7$R$^8$, —S(=O)$_2$NR$^7$R$^8$, —C(=O)NR$^7$R$^8$, hydroxy, halogen, cyano, trifluoromethyl, —OCF$_3$, —OCHF$_2$, —OCH$_2$CHF$_2$, C$_{1-6}$-alkyl, C$_{2-6}$-alkenyl, C$_{2-6}$-alkynyl, C$_{1-6}$-alkoxy, C$_{1-6}$-alkylthio, C$_{1-6}$-alkylsulfonyl, —C(=O)OR$^7$, C$_{1-6}$-alkyl-carbonyl, —C(=NOR$^7$)C$_{1-6}$-alkyl, C$_{3-10}$-cycloalkyl, C$_{3-10}$-cycloalkylcarbonyl, —C(=NOR$^7$)C$_{3-10}$-cycloalkyl, aryl-C$_{1-6}$-alkyl, arylamino, aroyl, arylsulfonyl, —C(=NOR$^7$)aryl, arylthio, and aryloxy, wherein R$^7$ and R$^8$ independently are hydrogen or C$_{1-6}$-alkyl, V is aryl or C$_{3-10}$-cycloalkyl, which are unsubstituted or substituted with one or more substituents selected from nitro, —NR$^{10}$R$^{11}$, —S(=O)$_2$ NR$^{10}$R$^{11}$, —C(=O)NR$^{10}$R$^{11}$, hydroxy, halogen, cyano, trifluoromethyl, —OCF$_3$, —OCHF$_2$, —OCH$_2$CHF$_2$, C$_{1-6}$-alkyl, C$_{2-6}$-alkenyl, C$_{2-6}$-alkynyl, C$_{1-6}$-alkoxy, C$_{1-6}$-alkylca, C$_{1-6}$-alkylthio, C$_{1-6}$-alkylsulfonyl, —C(=O)OR$^{10}$, C$_{1-6}$-alkylcarbonyl, —C(=NOR$^{10}$)C$_{1-6}$-alkyl, oxo, C$_{3-10}$-cycloalkyl, C$_{3-10}$-cycloalkylcarbonyl, —C(=NOR$^{10}$)C$_{3-10}$-cycloalkyl, arylamino, aroyl, arylsulfonyl, —C(=NOR$^{10}$)aryl, and arylthio, wherein R$^{10}$ and R$^{11}$ independently are hydrogen or C$_{1-6}$-alkyl, aryl-C$_{1-6}$-alkyl, aryl or aryloxy, which are unsubstituted or substituted with one or more substituents selected from nitro, hydroxy, C$_{1-6}$-alkyl, C$_{1-6}$-alkoxy, cyano, trifluoromethyl, —OCF$_3$, halogen C$_{1-6}$-alkyl, C$_{2-6}$-alkenyl or C$_{2-6}$-alkynyl, which are unsubstituted or substituted with one or more substituents selected from C$_{3-10}$-cycloalkyl and aryl, which are unsubstituted or substituted with one or more substituents selected from nitro, —NR$^{12}$R$^{13}$, —S(=O)$_2$NR$^{12}$R$^{13}$, —C(=O)NR$^{12}$R$^{13}$, hydroxy, halogen, cyano, trifluoromethyl, —OCF$_3$, —OCHF$_2$, —OCH$_2$CHF$_2$, C$_{1-6}$-alkyl, C$_{2-6}$-alkenyl, C$_{2-6}$-alkynyl, C$_{1-6}$-alkoxy, C$_{1-6}$-alkylthio, C$_{1-6}$-alkylsulfonyl, —C(=O)OR$^{12}$, C$_{1-6}$-alkylcarbonyl, —C(=NOR$^{12}$)C$_{1-6}$-alkyl, C$_{3-10}$-cycloalkyl, C$_{3-10}$-cycloalkylcarbonyl, —C(=NOR$^{12}$)C$_{3-10}$-cycloalkyl, aryl-C$_{1-6}$-alkyl, arylamino, aroyl, arylsulfonyl, —C(=NOR$^{12}$)aryl, arylthio, and aryloxy, wherein R$^{12}$ and R$^{13}$ independently are hydrogen or C$_{1-6}$-alkyl, or any stereoisomer or tautomeric form thereof or a mixture thereof or a pharmaceutically acceptable salt thereof.

25. The compound according to claim 1, selected from the group of 4-(2-ethylphenoxymethyl)-4,5,6,7-tetrahydro-1H-benzimidazole, 4-(4-cyanophenoxymethyl)-4,5,6,7-tetrahydro-1H-benzimidazole, 4-(1-naphthyloxymethyl)-4,5,6,7-tetrahydro-1H-benzimidazole, 4-(2-chlorophenoxymethyl)-4,5,6,7-tetrahydro-1H-benzimidazole, 4-(2,4-difluorophenoxymethyl)-4,5,6,7-tetrahydro-1H-benzimidazole, 4-(4-trifluoromethoxyphenoxymethyl)-4,5,6,7-tetrahydro-1H-benzimidazole, 4-(4-trifluoromethylphenoxymethyl)-4,5,6,7-tetrahydro-1H-benzimidazole, 3,5-dimethyl-4-(4,5,6,7-tetrahydro-1H-benzimidazol-4-ylmethoxy)benzonitrile, 3-chloro-4-(4,5,6,7-tetrahydro-1H-benzimidazol-4-ylmethoxy)benzonitrile, 3-(4,5,6,7-tetrahydro-1H-benzimidazol-4-ylmethoxy)benzonitrile, cyclopropyl-[4-(4,5,6,7-tetrahydro-1H-benzimidazol-4-ylmethoxy)phenyl]methanone, 3-methoxy-4-(4,5,6,7-tetrahydro-1H-benzimidazol-4-ylmethoxy)benzonitrile, 5-(4,5,6,7-tetrahydro-1H-benzimidazol-4-ylmethoxy)-3,4-dihydro-2H-naphthalen-1-one, 4-(4-chlorophenoxymethyl)-4,5,6,7-tetrahydro-1H-benzimidazole,

[5-chloro-2-(4,5,6,7-tetrahydro-1H-benzimidazol-4-ylmethoxy)phenyl]phenylmethanone, 4-(2-Chlorophenoxymethyl)-1,4,5,6,7,8-hexahydrocycloheptaimidazole, 4-(2,4-Difluorophenoxymethyl)-1,4,5,6,7,8-hexahydrocycloheptaimidazole, 4-(3-Acetylphenoxymethyl)-1,4,5,6,7,8-hexahydrocycloheptaimidazole 4-(1,4,5,6,7,8-hexahydrocycloheptaimidazol-4-yl-methoxy)benzonitrile, or any optical or geometric isomer or tautomeric form thereof or a mixture thereof or a pharmaceutically acceptable salt thereof.

26. The compound according to claim 1, wherein the compound is 4-(4-cyanophenoxymethyl)-4,5,6,7-tetrahydro-1H-benzimidazole, or stereoisomer or tautomeric form thereof or a mixture thereof or a pharmaceutically acceptable salt thereof.

27. The compound according to claim 25 wherein the pharmaceutically acceptable salt is the hydrochloride or oxalic acid salt.

28. A pharmaceutical composition comprising, as an active ingredient, at least one compound according to claim 1 together with one or more pharmaceutically acceptable carriers or excipients.

29. The pharmaceutical composition according to claim 28 in unit dosage form, comprising from about 0.05 mg to about 1000 mg of the compound of formula (I).

* * * * *